US006927027B2

(12) United States Patent
Erikson et al.

(10) Patent No.: US 6,927,027 B2
(45) Date of Patent: Aug. 9, 2005

(54) NUCLEIC ACID MULTIPLEX FORMATION

(75) Inventors: Glen H. Erikson, Providencials (TC); Jasmine I. Daksis, Richmond Hill (CA); Ivana Kandic, Toronto (CA); Pierre Picard, Ottawa (CA)

(73) Assignee: Ingeneus Corporation, Bridgetown (BB)

( * ) Notice: Subject to any disclaimer, the term of this patent is extended or adjusted under 35 U.S.C. 154(b) by 305 days.

(21) Appl. No.: 09/885,731

(22) Filed: Jun. 20, 2001

(65) Prior Publication Data

US 2003/0113716 A1 Jun. 19, 2003

Related U.S. Application Data

(63) Continuation-in-part of application No. 09/664,827, filed on Sep. 19, 2000, which is a continuation-in-part of application No. 09/613,263, filed on Jul. 10, 2000, now Pat. No. 6,420,115, which is a continuation-in-part of application No. 09/468,679, filed on Dec. 21, 1999, now Pat. No. 6,403,313.

(51) Int. Cl.[7] .......................... C12Q 1/68; C07H 21/04
(52) U.S. Cl. ....................................... 435/6; 536/24.32
(58) Field of Search ........................ 435/6; 536/24.32, 536/24.31, 24.33

(56) References Cited

U.S. PATENT DOCUMENTS

| | | | |
|---|---|---|---|
| 4,220,450 A | 9/1980 | Maggio | |
| 4,876,187 A | 10/1989 | Duck et al. | |
| 4,963,477 A | 10/1990 | Tchen | |
| 5,011,769 A | 4/1991 | Duck et al. | |
| 5,176,996 A | 1/1993 | Hogan et al. | |
| 5,332,659 A | 7/1994 | Kidwell | |
| 5,403,711 A | 4/1995 | Walder et al. | |
| 5,451,502 A * | 9/1995 | George, Jr. .................. | 435/6 |
| 5,538,848 A | 7/1996 | Livak et al. | |
| 5,539,082 A | 7/1996 | Nielsen et al. | |
| 5,558,998 A | 9/1996 | Hammond et al. | |
| 5,660,988 A | 8/1997 | Duck et al. | |
| 5,705,346 A | 1/1998 | Okamoto et al. | |
| 5,707,801 A | 1/1998 | Bresser et al. | |
| 5,731,146 A | 3/1998 | Duck et al. | |
| 5,800,984 A | 9/1998 | Vary | |
| 5,800,992 A | 9/1998 | Fodor et al. | |
| 5,814,447 A | 9/1998 | Ishiguro et al. | |
| 5,814,516 A | 9/1998 | Vo-Dinh | |
| 5,824,477 A | 10/1998 | Stanley | |
| 5,824,557 A | 10/1998 | Burke et al. | |
| 5,846,729 A | 12/1998 | Wu et al. | |
| 5,861,124 A | 1/1999 | Hosoi et al. | |
| 5,874,555 A | 2/1999 | Dervan et al. | |
| 5,888,739 A | 3/1999 | Pitner et al. | |
| 5,912,332 A | 6/1999 | Agrawal et al. | |
| 5,928,863 A | 7/1999 | Fresco | |
| 5,948,897 A | 9/1999 | Sen et al. | |
| 6,013,442 A | 1/2000 | Kolesar et al. | |
| 6,017,709 A | 1/2000 | Hardin et al. | |
| 6,027,880 A | 2/2000 | Cronin et al | |
| 6,046,004 A | 4/2000 | Wu et al. . | |
| 6,048,690 A | 4/2000 | Heller et al. | |
| 6,060,242 A | 5/2000 | Nie et al. | |
| 6,107,078 A | 8/2000 | Keese et al. | |
| 6,117,657 A | 9/2000 | Usman et al. | |
| 6,251,591 B1 | 6/2001 | Wu et al. | |
| 6,255,050 B1 | 7/2001 | Nie et al. | |
| 6,255,469 B1 | 7/2001 | Seeman et al. | |
| 6,265,170 B1 | 7/2001 | Picard et al. | |
| 6,287,772 B1 | 9/2001 | Stefano et al. | |
| 6,312,925 B1 | 11/2001 | Meyer, Jr. et al. | |
| 6,420,115 B1 * | 7/2002 | Erikson et al. ................ | 435/6 |
| 6,461,810 B1 * | 10/2002 | Fresco et al. .................. | 435/6 |

FOREIGN PATENT DOCUMENTS

| | | |
|---|---|---|
| GB | 2333359 A | 7/1999 |
| GB | 2338301 A | 12/1999 |
| WO | WO 97/45539 A1 | 12/1997 |
| WO | WO 98/29428 A1 | 7/1998 |
| WO | WO 00/20633 A1 | 4/2000 |
| WO | WO 00/43543 A1 | 7/2000 |

OTHER PUBLICATIONS

McGavin et al. A computer graphics study of multistranded DNA models. J. Mo. Graphics, vol. 7, pp. 218–232, 1989.*
Abstract of JP 5237000, Yoshitami (Sep. 17, 1993).
Baran et al., *Nucleic Acids Research* 25:297–303 (1997).
Bohmann et al., *Science*, 238:1386–1392 (Dec. 1987).
Carlsson et al., 380 *Nature* 207 (Mar. 21, 1996).
Chan et al., *J. Mol. Med.* 75 Issue 4:267–282 (1997).
Dalrymple et al., *Nucleic Acids Research*, vol. 13, No. 21, pp. 7865–7879 (1985).
Durland et al., *Biochemistry*, 30:9246–9255 (1991).
Egholm et al., 365 *Nature* 566 (Oct. 7, 1993).
Floris et al., 260 *Eur. J. Biochem.* 801–809 (1999).
Hill et al., *Methods in Enzymology*, 278:390–416 (1997).
Johansen and Jacobsen, *J Biomol Struct Dyn*, 16(2):205–22 (Oct. 1998) (Abstract).
Kadonaga et al., *Cell*, 51:1079–1090 (Dec. 24, 1987).
Kukreti et al. 25 *Nucleic Acids Research* 4264–4270 (1997).
Marsh et al., *Nucleic Acids Research*, 23:696–700 (1995).
Marsh et al., *Biochemistry* 33 10718–10724 (1994).
Mazumder et al., *Biochemistry* 35:13762–13771 (1996).
Sen et al., *Nature* 334:364–366 (Jul. 28, 1988).
Sen et al., *Biochemistry* 31:65–70 (1992).
Sturm et al., *Genes & Development*, 2:1582–1599 (1988).
U.S. Appl. No. 09/713,177, Erikson et al.
Tomac et al., 118 *J. Am. Chem Soc.* 5544–5552 (1996).
Watson, James, "A Personal Account of the Discovery of the Structure of DNA," (1968).

(Continued)

Primary Examiner—Jeffrey Fredman
Assistant Examiner—Suryaprabha Chunduru
(74) Attorney, Agent, or Firm—Caesar, Rivise, Bernstein, Cohen & Pokotilow, Ltd.

(57) ABSTRACT

Heteropolymeric triplexes and quadruplexes and methods for making them; the use of accelerator agents such as cations to create them; the use of fluorescent intercalators and fluorescent probe-bound non-intercalators to detect them.

27 Claims, 26 Drawing Sheets

OTHER PUBLICATIONS

Williamson et al., *Cell* 59:871–880 (Dec. 1, 1989).
Wilson et al., *Cell*, 74:115–125 (Jul. 16, 1993).
Zhurkin et al., *J. Mol. Biol.*, vol. 239, 181–200 (1994).
Rocher, Christophe et al., *Nucleic Acids Research*, "Initiation of DNA replication by DNA polymerases from primers forming a triple helix," 2001, vol. 29, No. 16, 3320–3326.
Deng et al., "Duplex to quadruplex equilibrium of the self–complementary oligonucleotide", *Biopolymer*, vol. 35, No. 6, pp. 677–681 (1995).
Eckhart et al., *The Journal of Biological Chemistry*, vol. 274, No. 5, pp. 2613–2615 (Jan. 29, 1999).
Lishanski et al., "Branch migration inhibition in PCR–amplified DNA; homogeneous mutation detection", *Nucleic Acids Research*, vol. 28, No. 9, pps. e42i–e42 vii (May 1, 2000).
McGavin, "Models of Specifically Paired Like (Homologous) Nucleic Acid Structures," *J. Mol. Biol.* (1971) 55, 293–298.
McGavin, "Relationships and Transformations Between Some Nucleic Acid Models," *J. Theor. Biol.* (1980) 85, 665–672.
McGavin, "Four Strand Recombination Models," *J. Theor. Biol.* (1989) 136, 135–150.
McGavin, "Four–Strand Structures, Kinks and Cruciforms in DNA," *J. Theor. Biol.* (1989) 138, 117–128.
McGavin et al., "A Computer Graphics Study of Multi-stranded DNA Models," *J. Mol Graphics.* (1989) 7, 218–232.
Salisbury et al., The bi–loop, a new general four–stranded DNA motif, *Prol. Natl. Acad. Sci. USA*, vol. 94, pp. 5515–5518 (May 1997).
Venczel et al. *J. Mol. Biol.*, 257, 219–224 (1996).
Zhang et al., "Dimeric DNA Quadruplex Containing Major Groove–aligned A•T•A•T and G•C•G•C Tetrads Stabilized by Inter–subunit Watson–Crick A•T and G•C Pairs", *J. Mol. Biol.*, 312, 1073–1088 (2001).

* cited by examiner

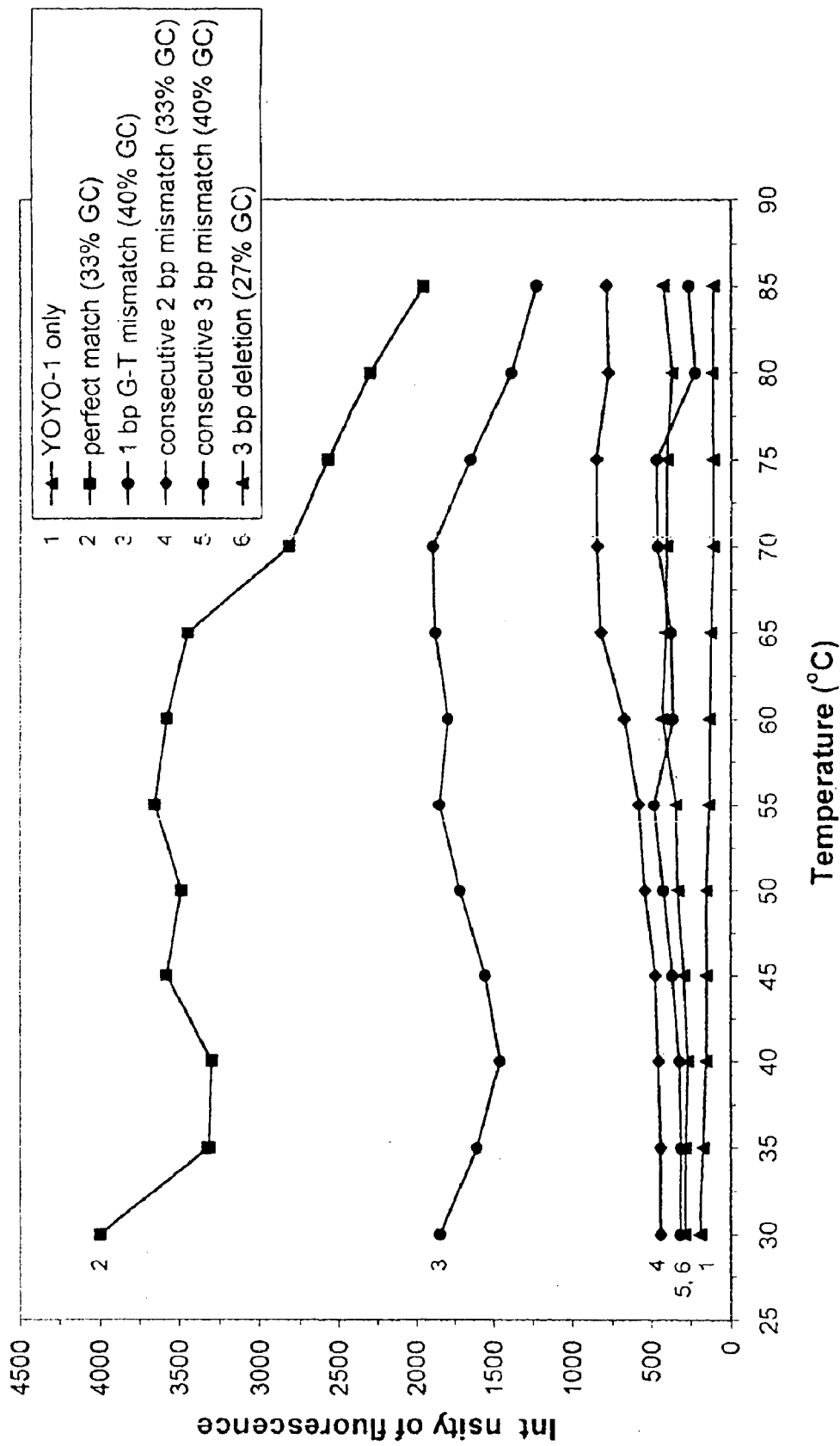

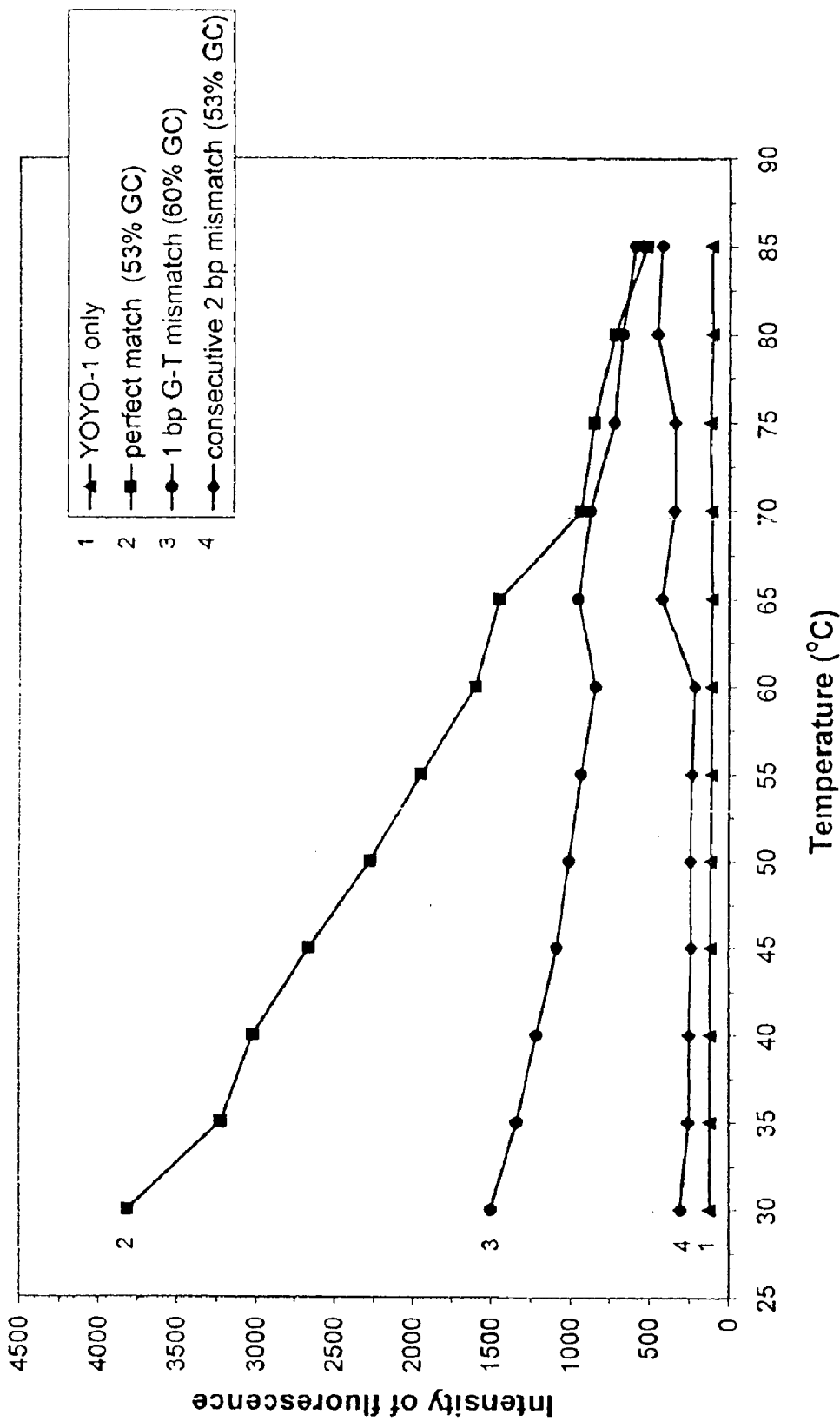

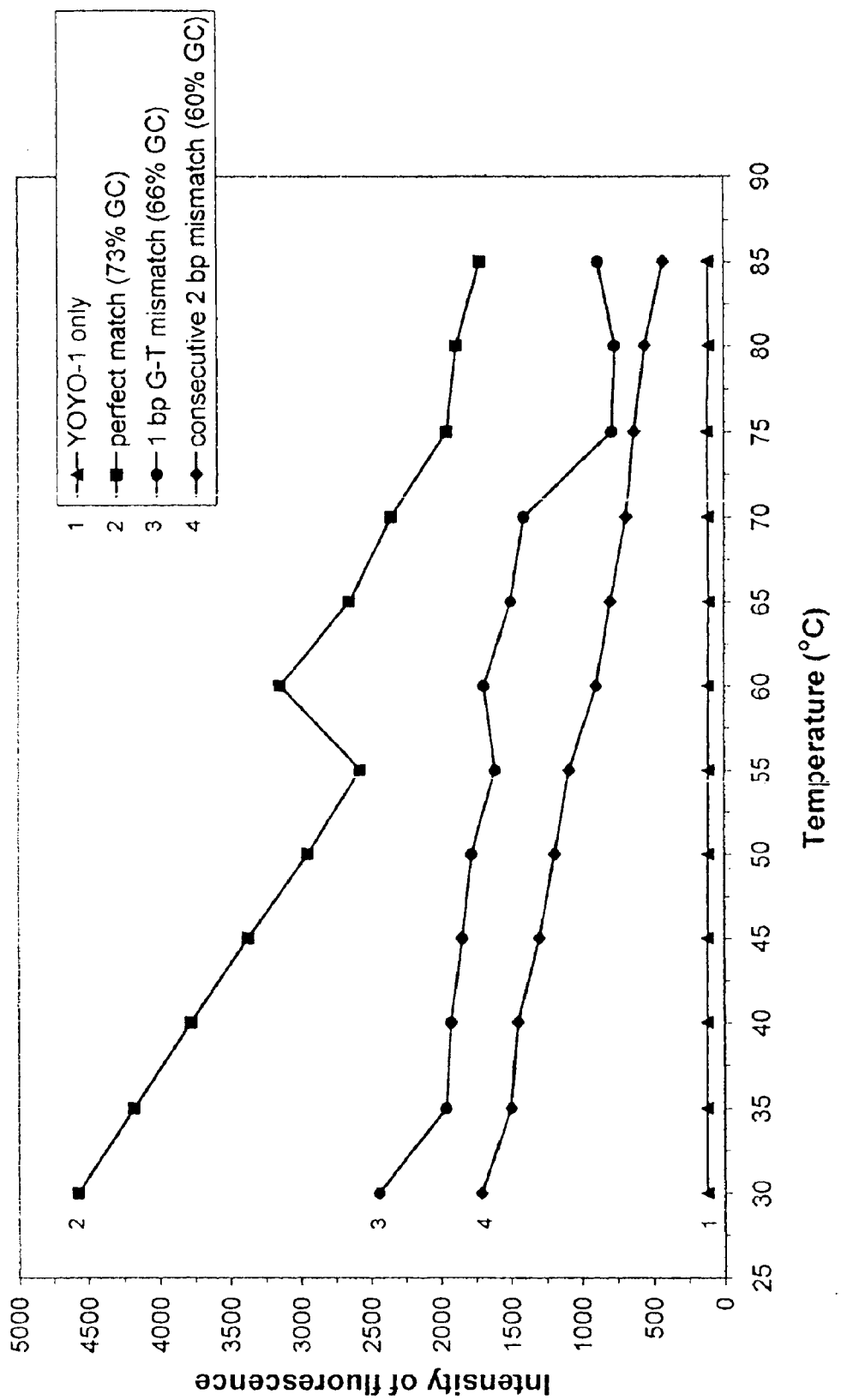
FIG. 2B. Binding of 15-mer antiparallel ssDNA to 50-mer dsDNA with YOYO-1 without prior denaturation of dsDNA

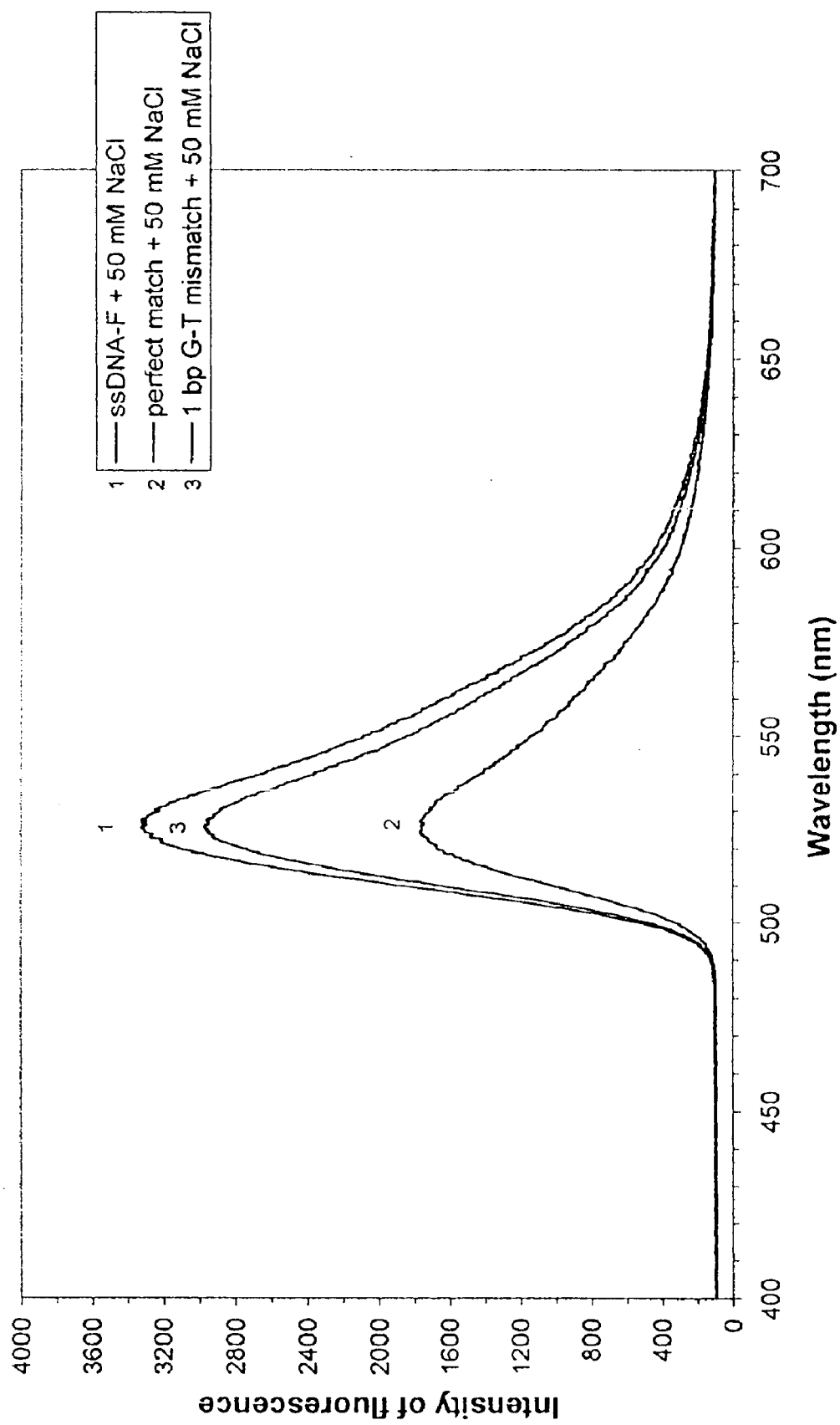
FIG. 3. Binding of 15-mer antiparallel ssDNA-F probe (4 pmole) (33% GC) and 50-mer dsDNA (0.4 pmole) in the presence of 50 mM NaCl (after 1 hr)

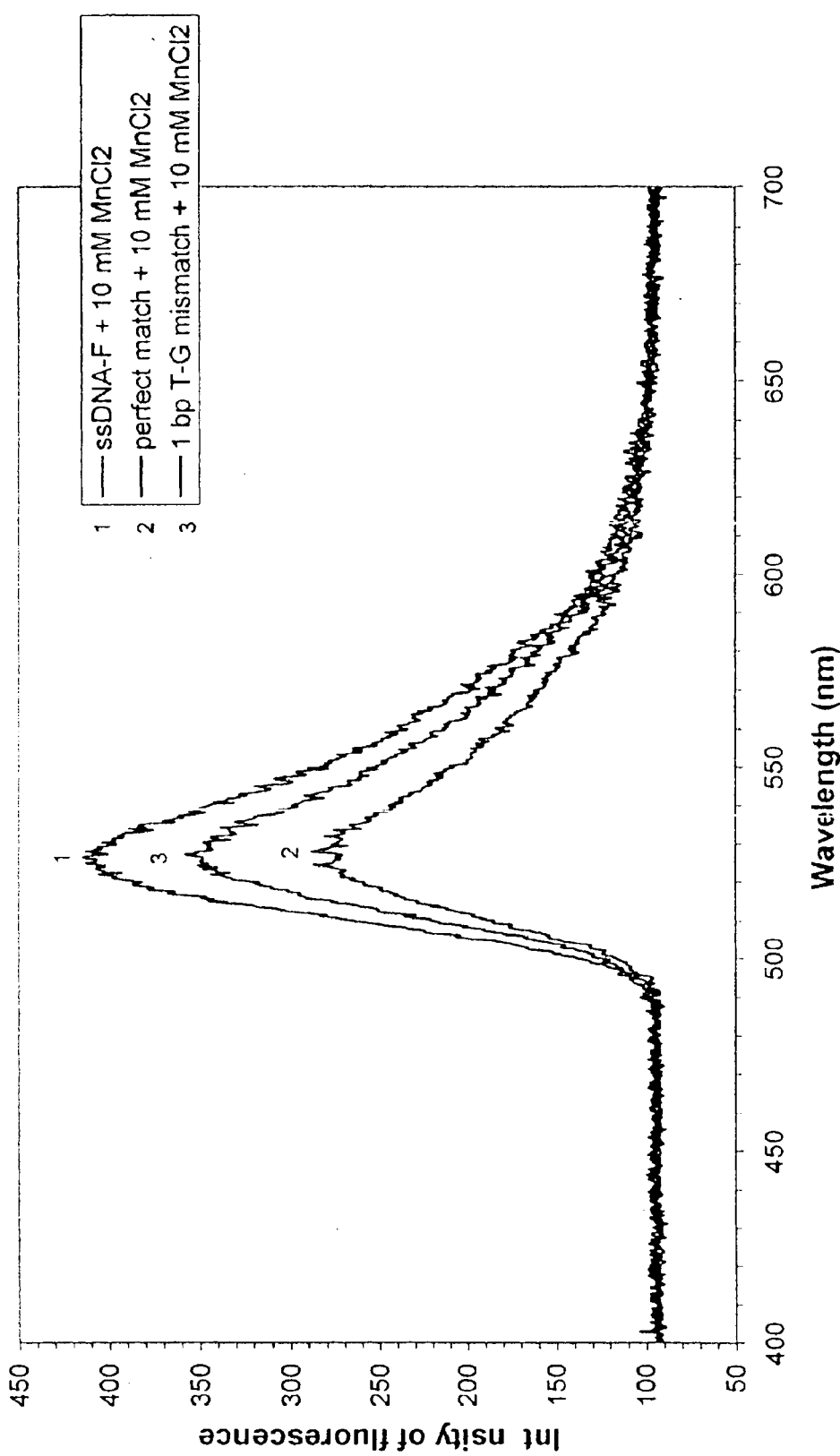
FIG. 4. Binding of 15-mer antiparallel ssDNA-F probe (4 pmole) (53% GC) and 50-mer dsDNA (0.4 pmole) in the presence of divalent cations (after 1 hr)

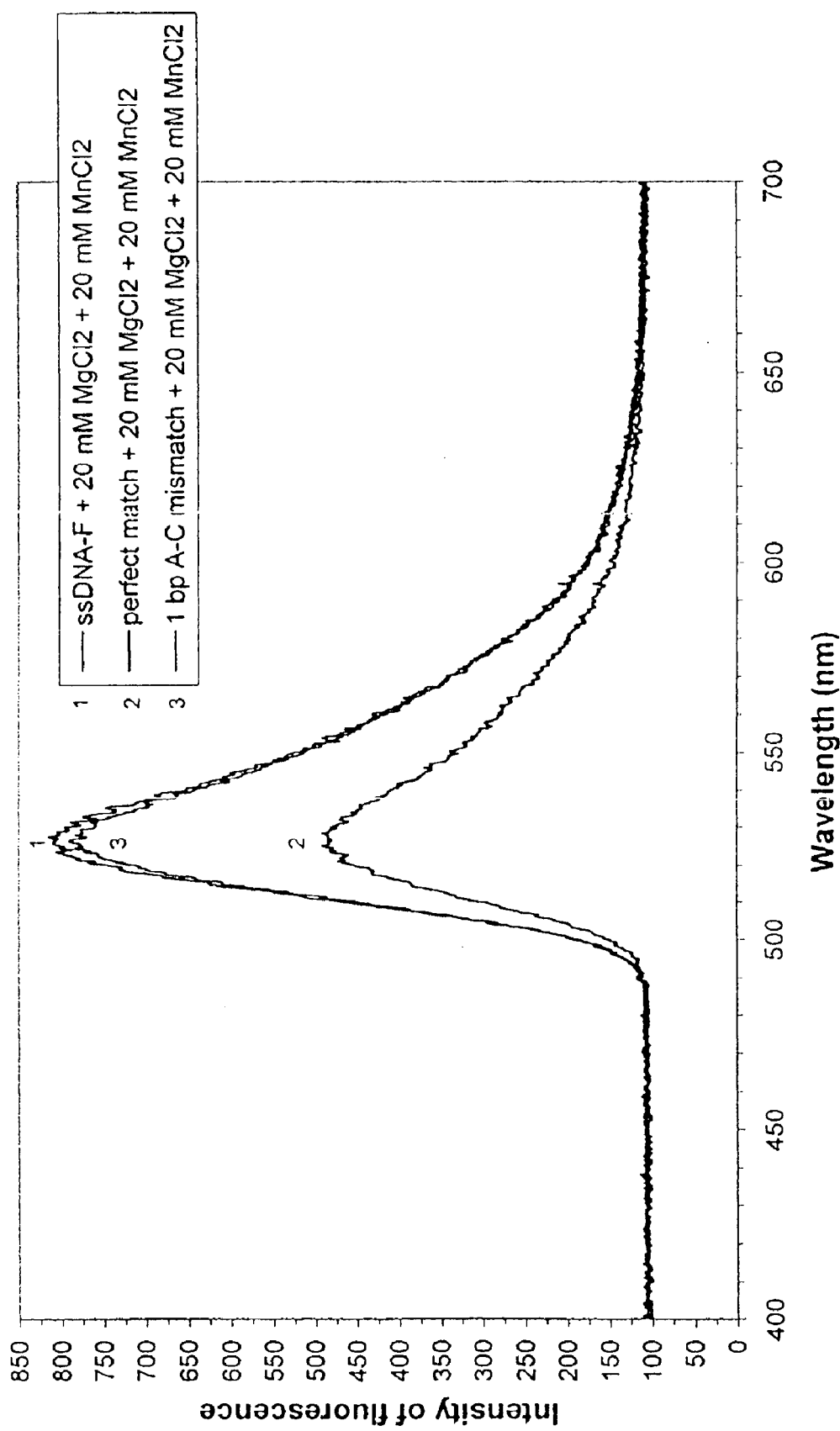
FIG. 5A. Binding of 15-mer antiparallel ssDNA-F probe (4 pmole) (73% GC) and 50-mer dsDNA (0.4 pmole) in the presence of divalent cations (after 1 hr)

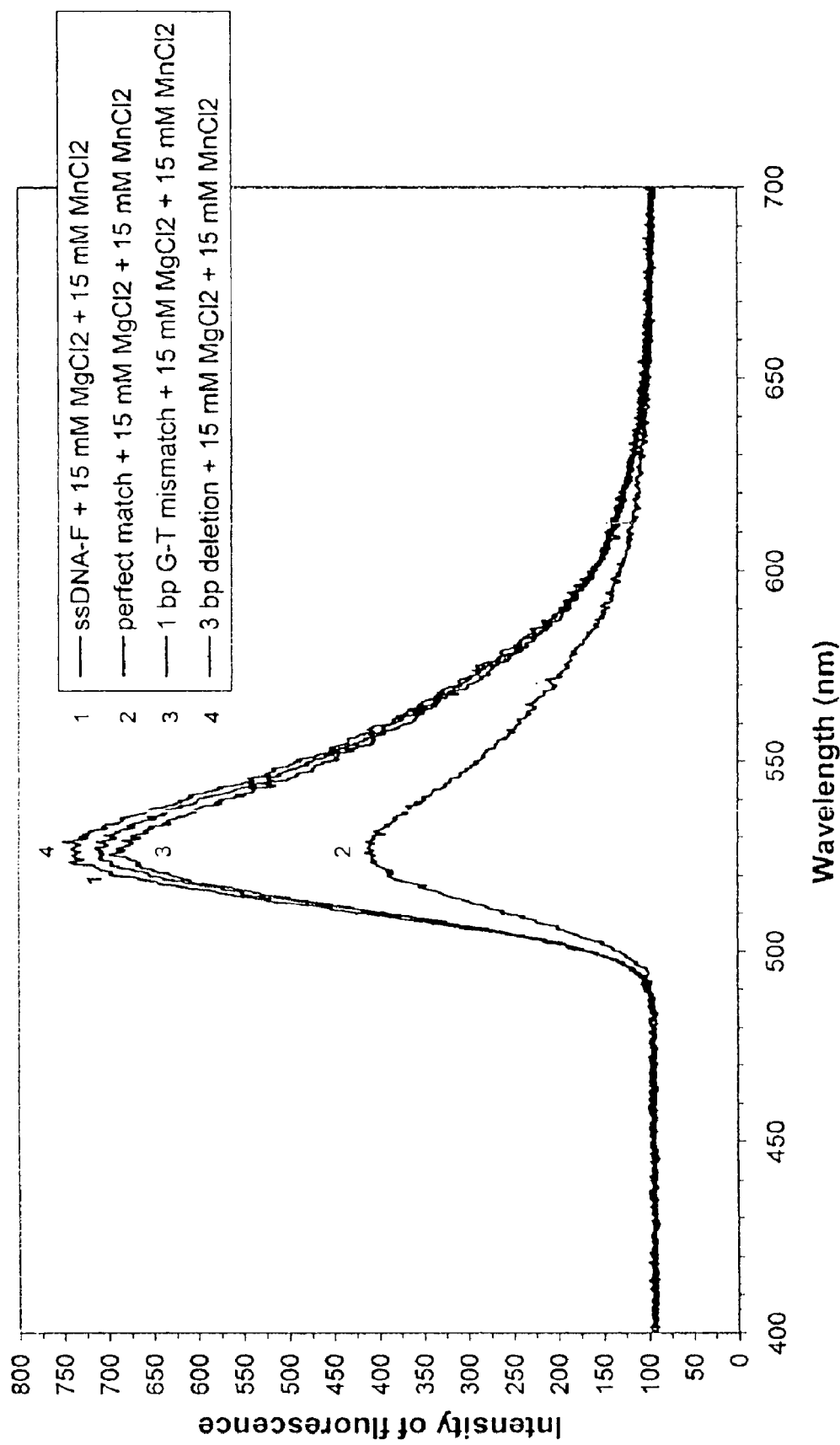
FIG. 5B. Binding of 15-mer antiparallel ssDNA-F probe (4 pmole) (33% GC) and 50-mer dsDNA (0.4 pmole) in the presence of divalent cations (after 1 hr)

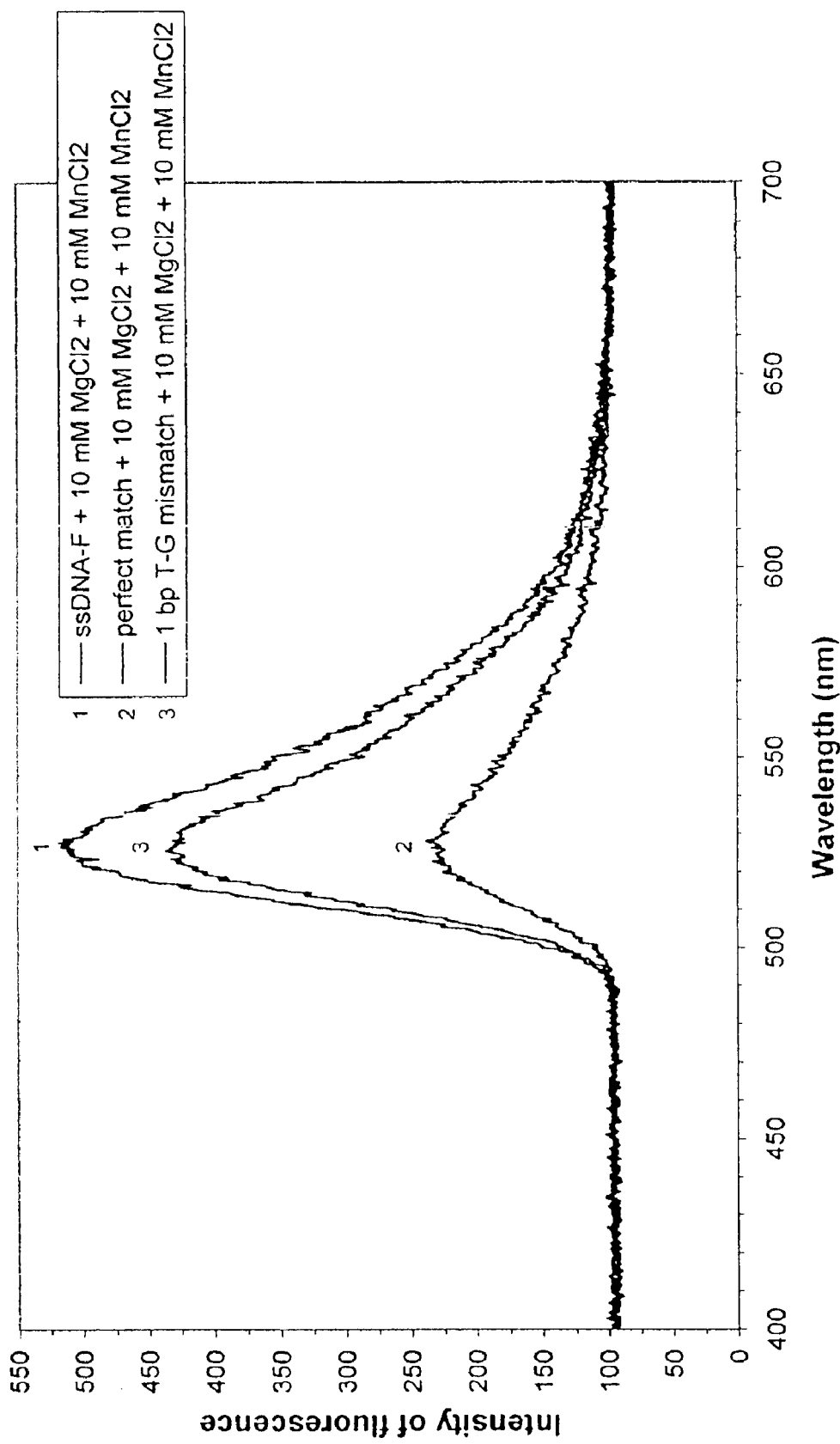
FIG. 5C. Binding of 15-mer antiparallel ssDNA-F probe (4 pmole) (53% GC) and 50-mer dsDNA (0.4 pmole) in the presence of divalent cations (after 1 hr)

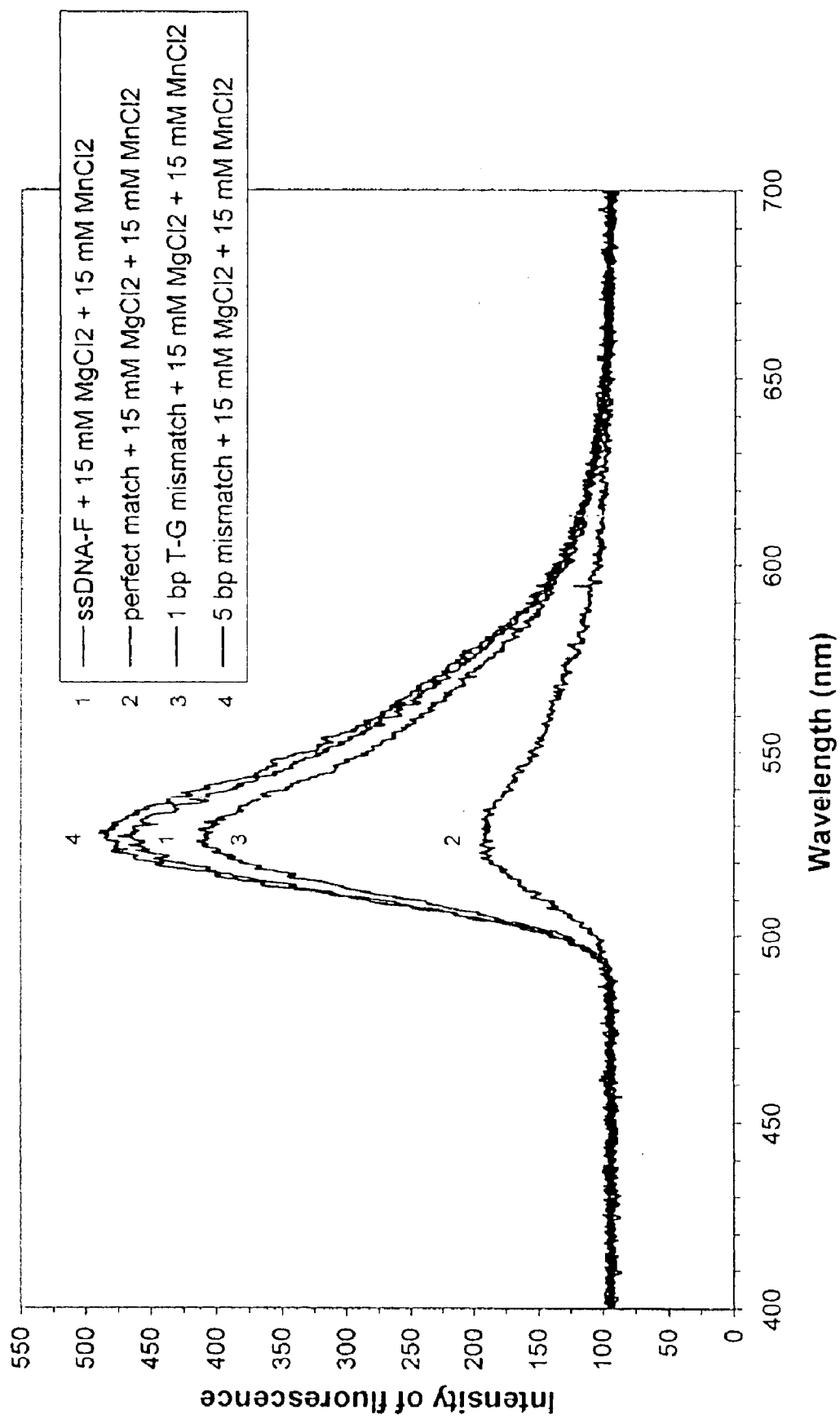
FIG. 5D. Binding of 15-mer antiparallel ssDNA-F probe (4 pmole) (53% GC) and 50-mer dsDNA (0.4 pmole) in the presence of divalent cations (after 1 hr)
1 — ssDNA-F + 15 mM MgCl2 + 15 mM MnCl2
2 — perfect match + 15 mM MgCl2 + 15 mM MnCl2
3 — 1 bp T-G mismatch + 15 mM MgCl2 + 15 mM MnCl2
4 — 5 bp mismatch + 15 mM MgCl2 + 15 mM MnCl2

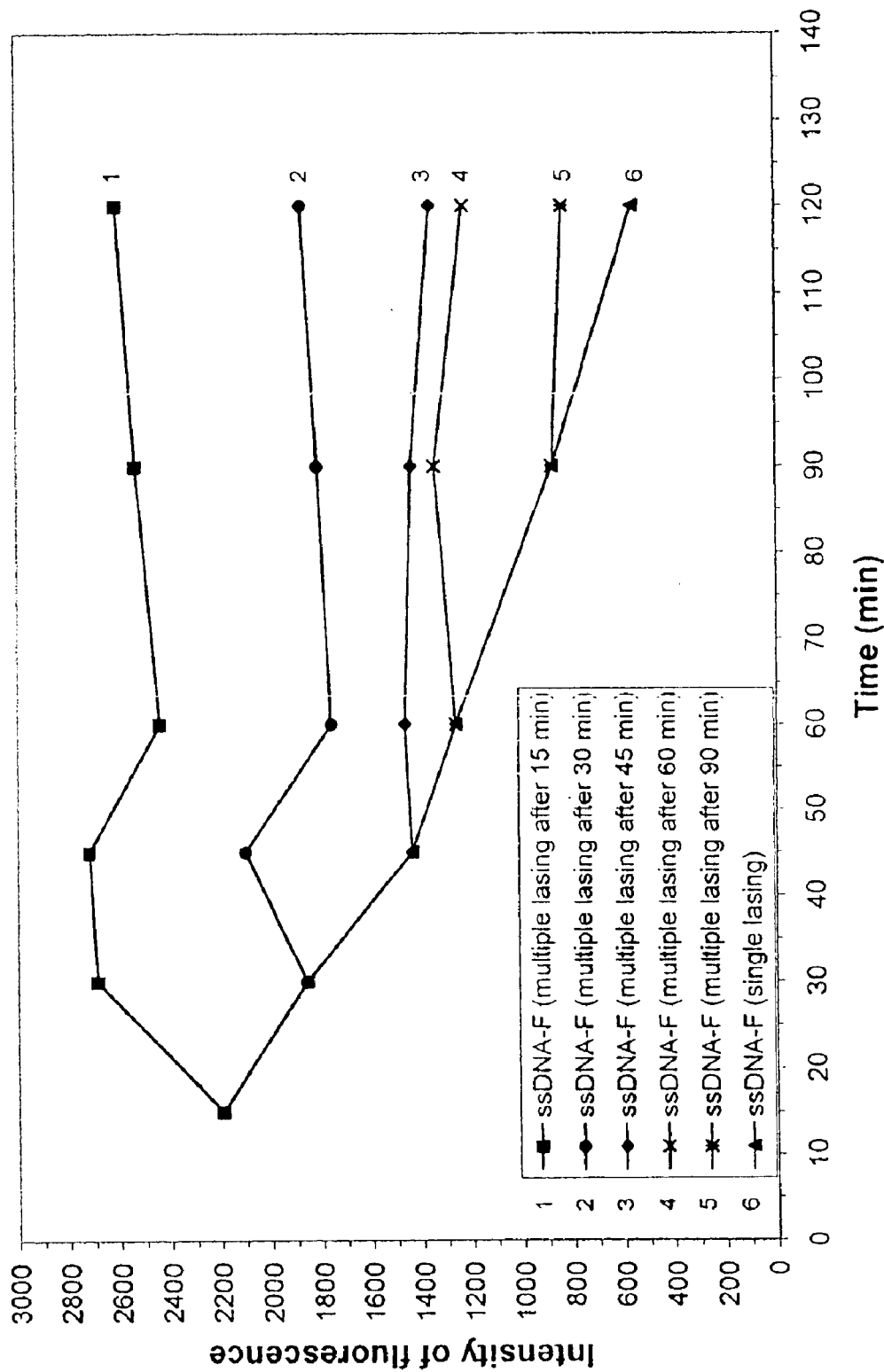
FIG. 6A. Effect of multiple laser treatment on cationic quench of 15-mer antiparallel ssDNA-F (4 pmole) by 10 mM $MgCl_2$ + 10 mM $MnCl_2$

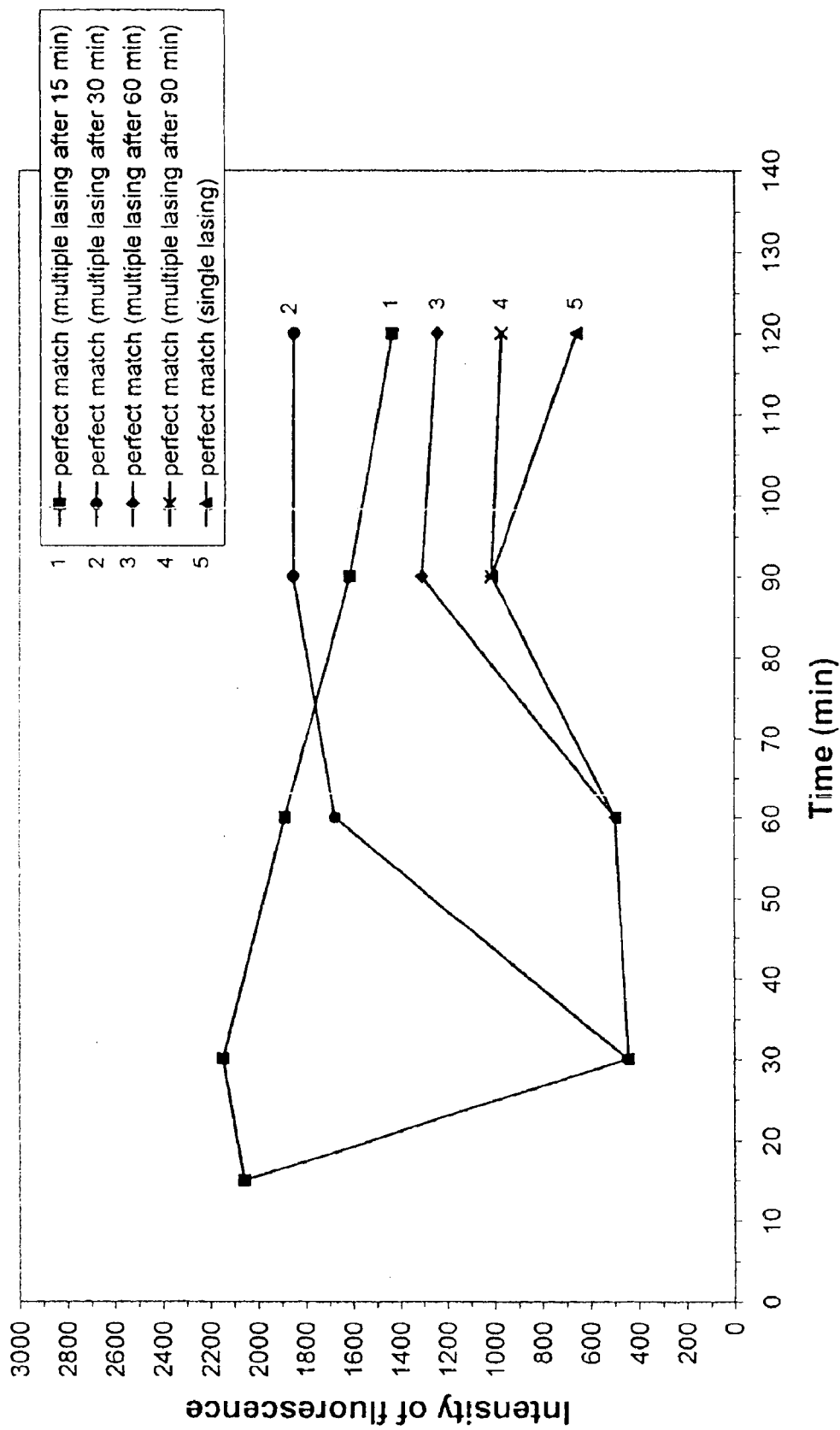
FIG. 6B. Effect of multiple laser treatment on complex formation between perfectly matched antiparallel 15-mer ssDNA-F (4 pmole) + 50-mer dsDNA (0.4 pmole) in the presence of 10 mM $MgCl_2$ + 10 mM $MnCl_2$

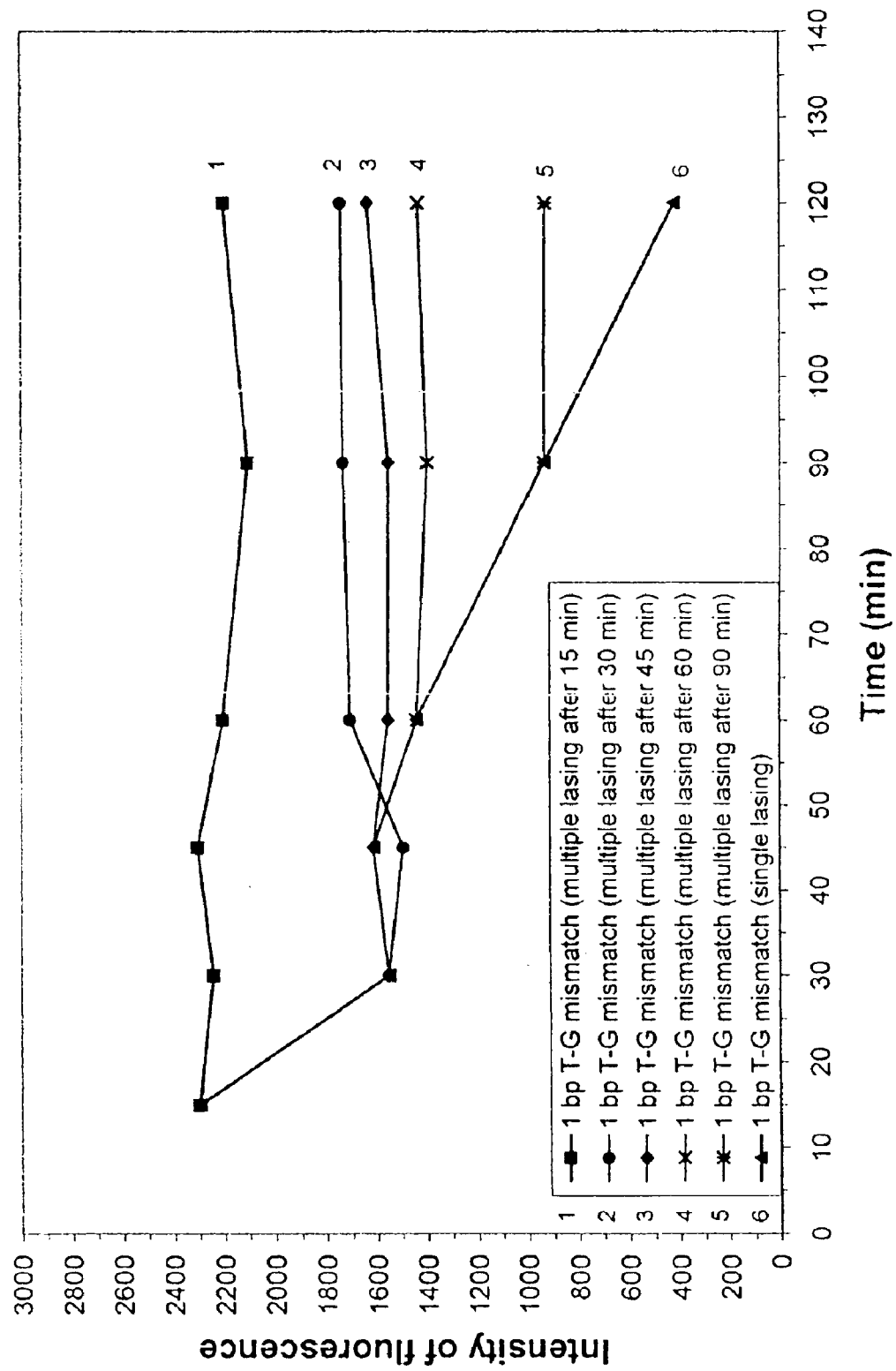
FIG. 6C. Effect of multiple laser treatment on complex formation between antiparallel 15-mer ssDNA-F (4 pmole) + 50-mer dsDNA (0.4 pmole) resulting in a 1 bp T-G mismatch in the presence of 10 mM $MgCl_2$ + 10 mM $MnCl_2$

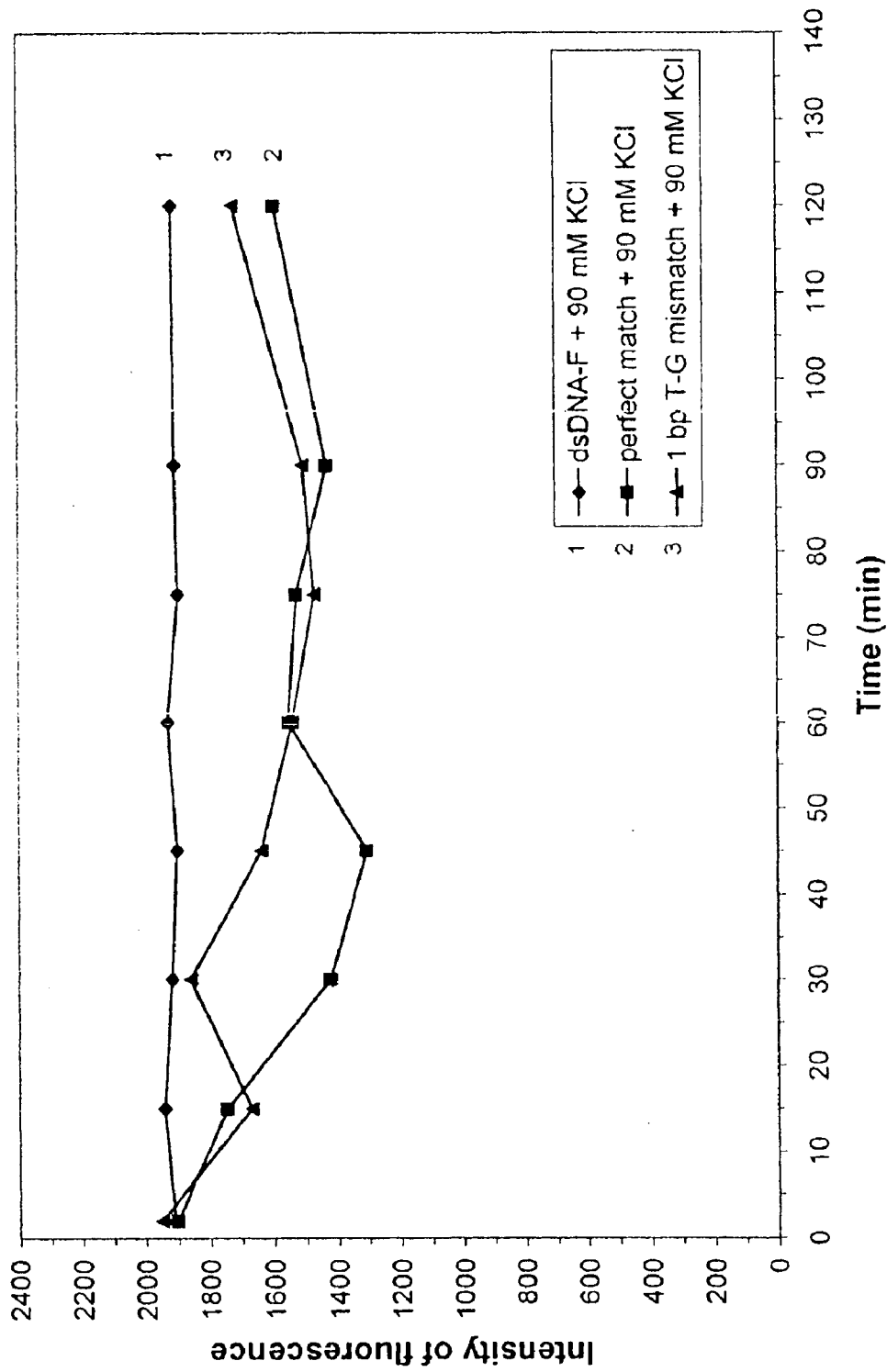
FIG. 7A. Binding of 15-mer dsDNA-F (4 pmole) (53% GC) and 50-mer dsDNA (0.4 pmole) in the presence of 90 mM KCl over time

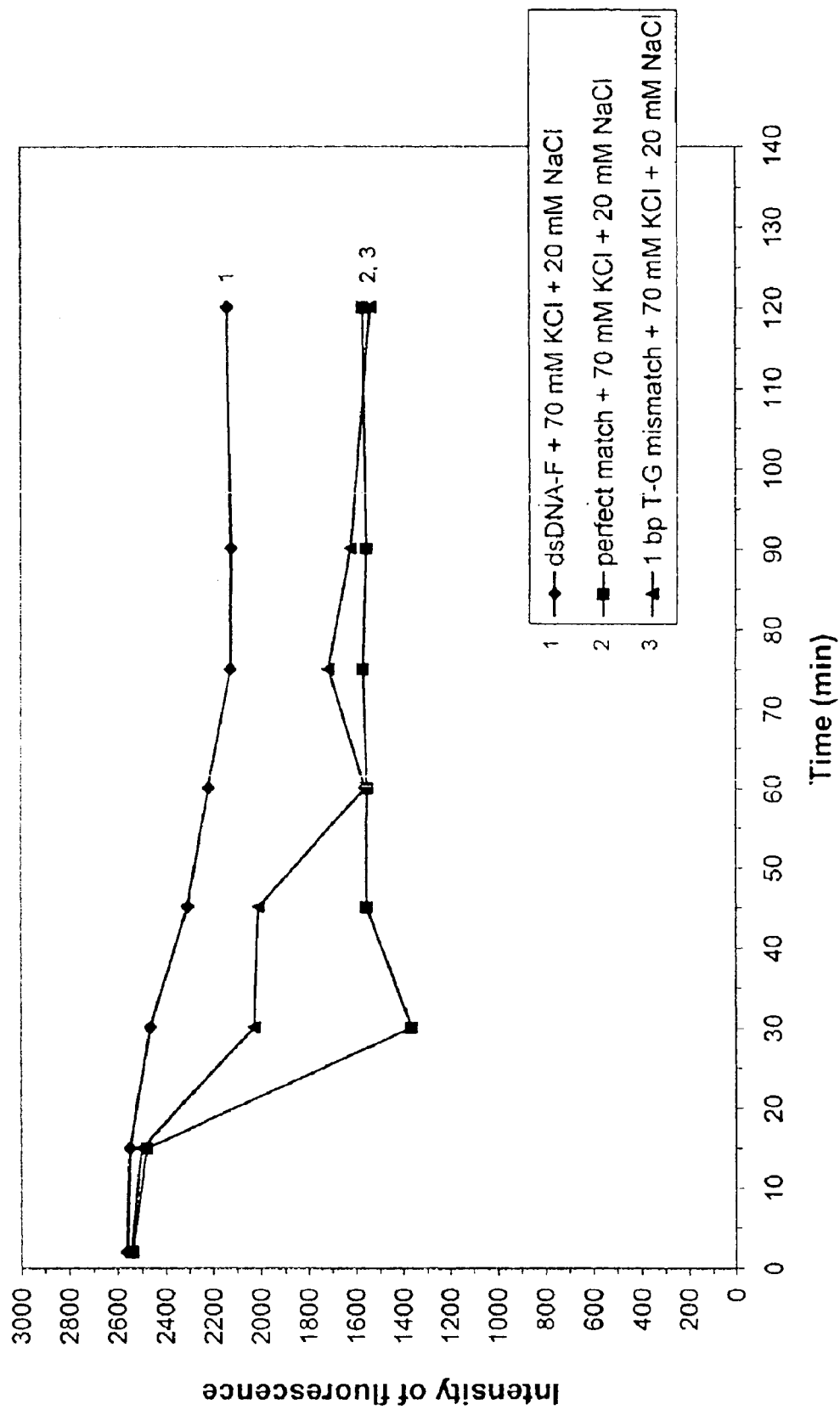
FIG. 7B. Binding of 15-mer dsDNA-F (4 pmole) (53% GC) and 50-mer dsDNA (0.4 pmole) in the presence of 70 mM KCl + 20 mM NaCl over time

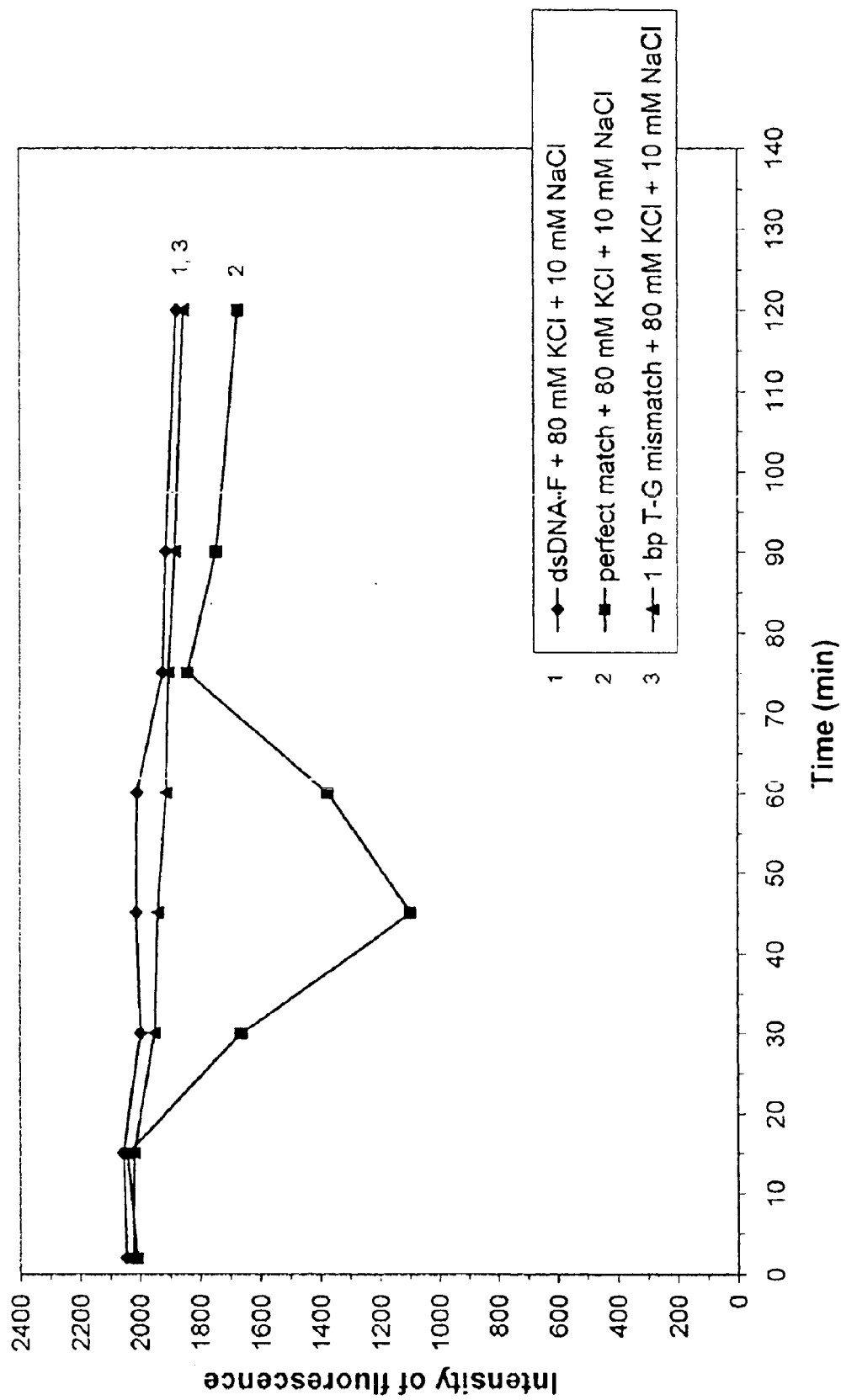

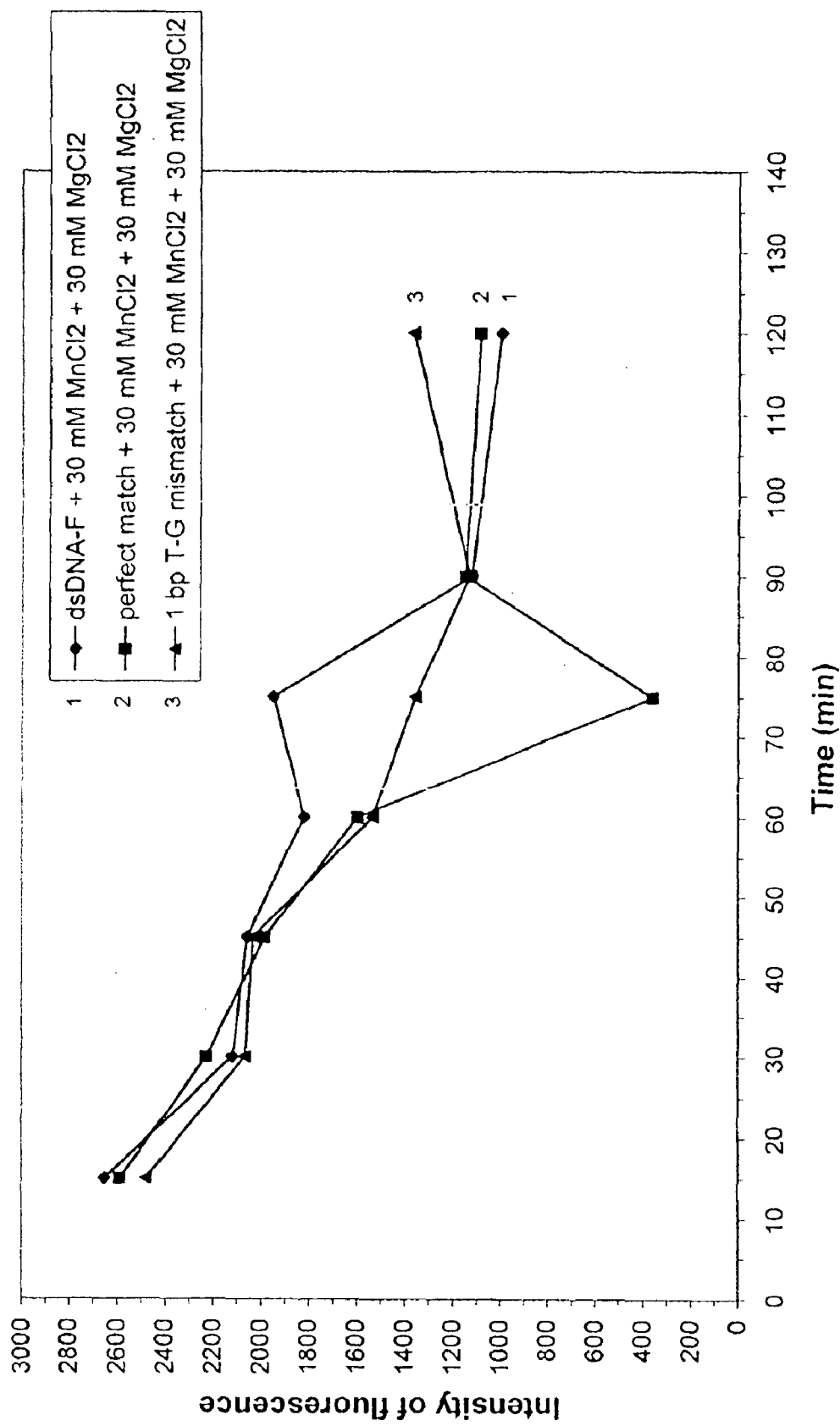
FIG. 8A. Binding of 15-mer dsDNA-F (4 pmole) (53% GC) and 50-mer dsDNA (0.4 pmole) in the presence of 30 mM $MnCl_2$ + 30 mM $MgCl_2$ over time

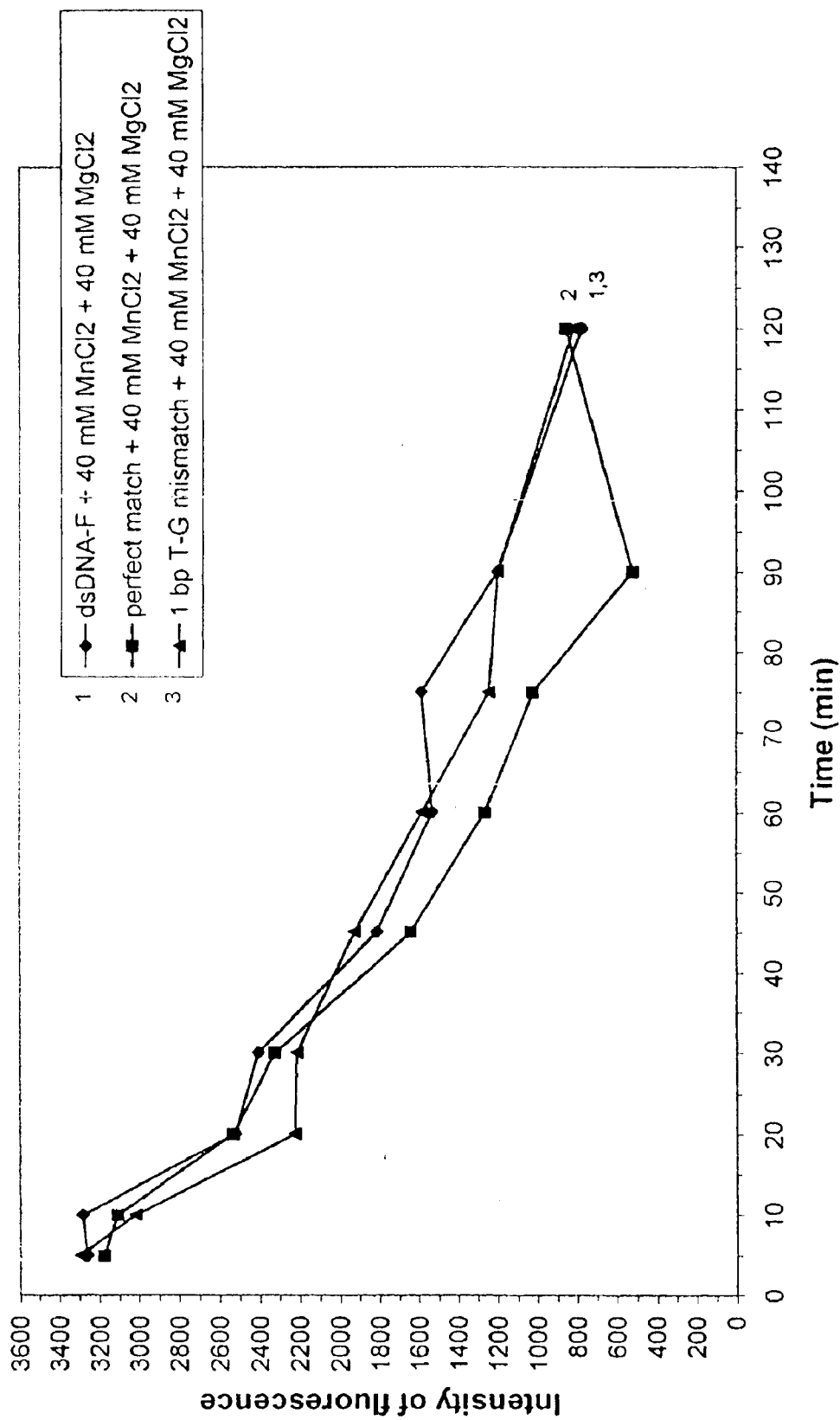
FIG. 8B. Binding of 15-mer dsDNA-F (4 pmole) (53% GC) and 50-mer dsDNA (0.4 pmole) in the presence of 40 mM $MnCl_2$ + 40 mM $MgCl_2$ over time

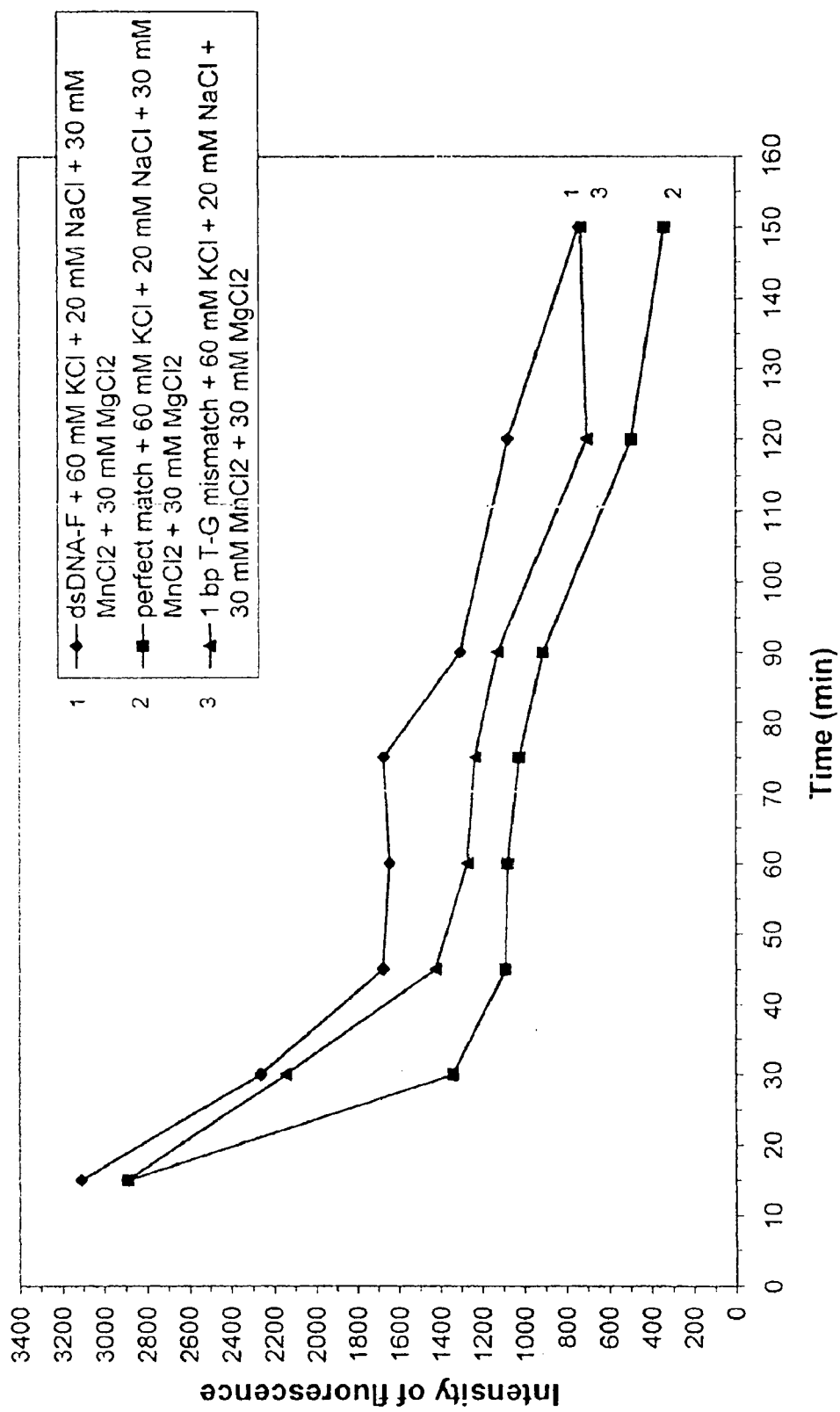
FIG. 9A. Binding of 15-mer dsDNA-F (4 pmole) (53% GC) and 50-mer dsDNA (0.4 pmole) in the presence of monovalent and divalent cations over time

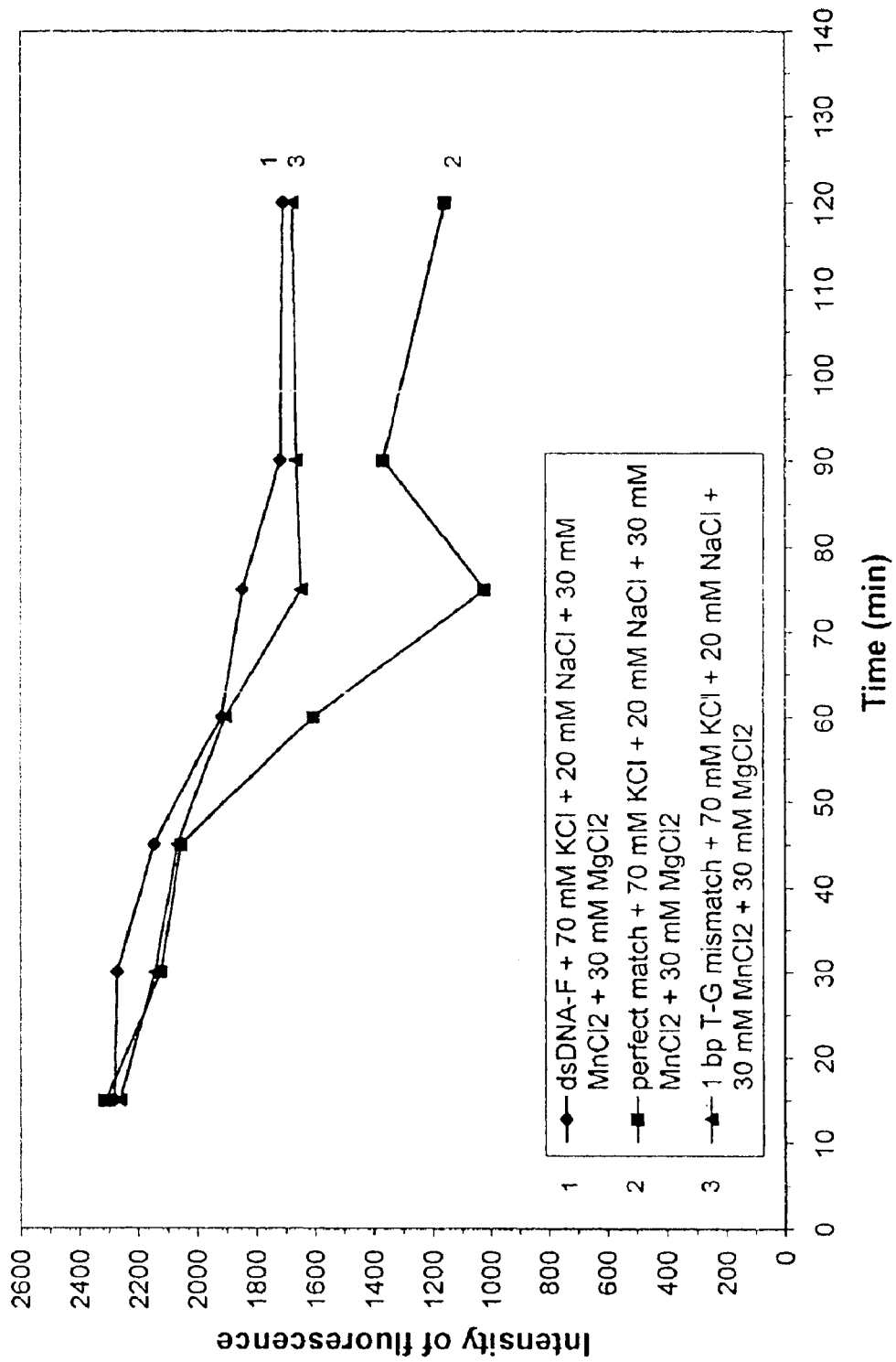

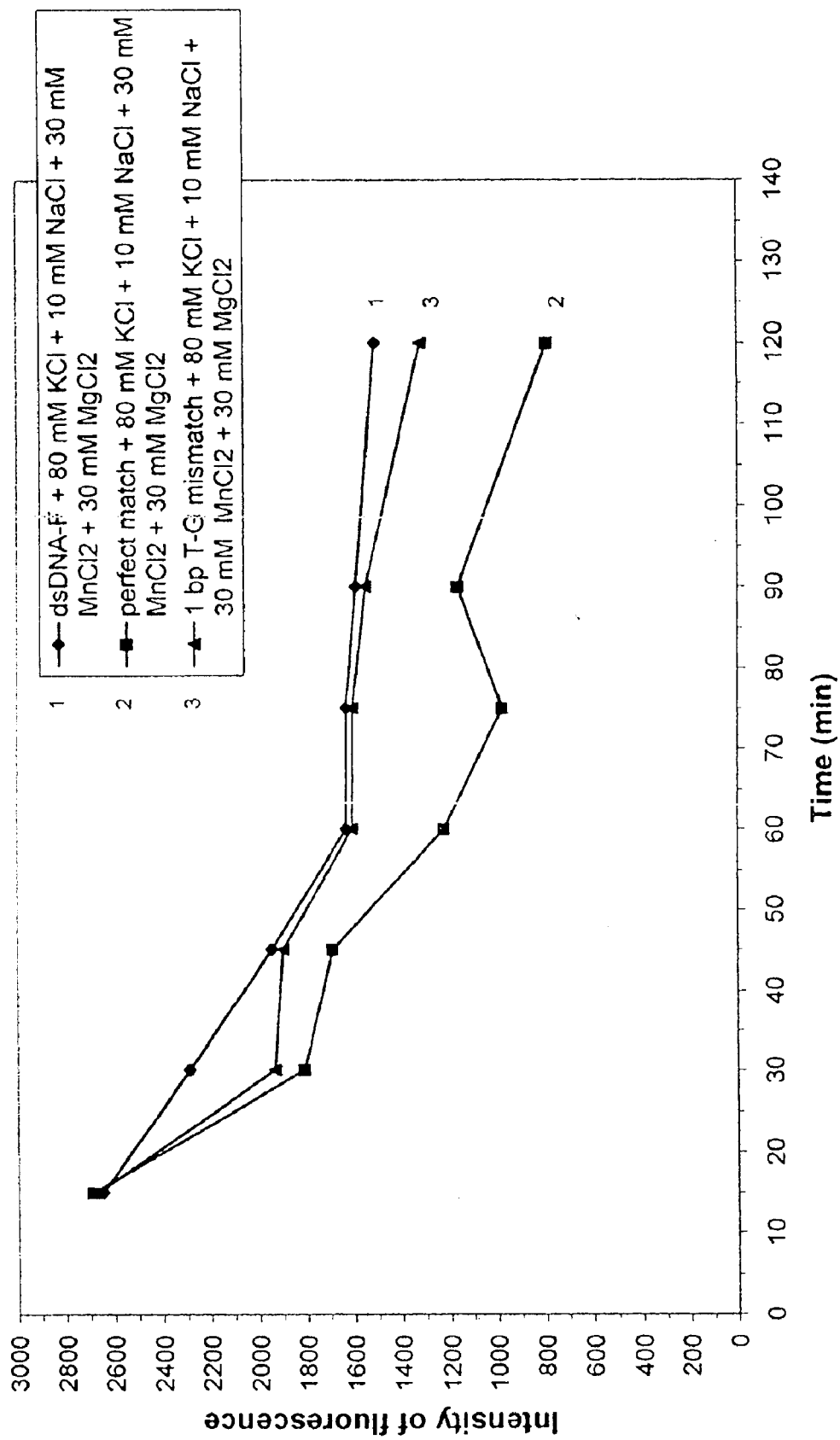
FIG. 9C. Binding of 15-mer dsDNA-F (4 pmole) (53% GC) and 50-mer dsDNA (0.4 pmole) in the presence of monovalent and divalent cations over time

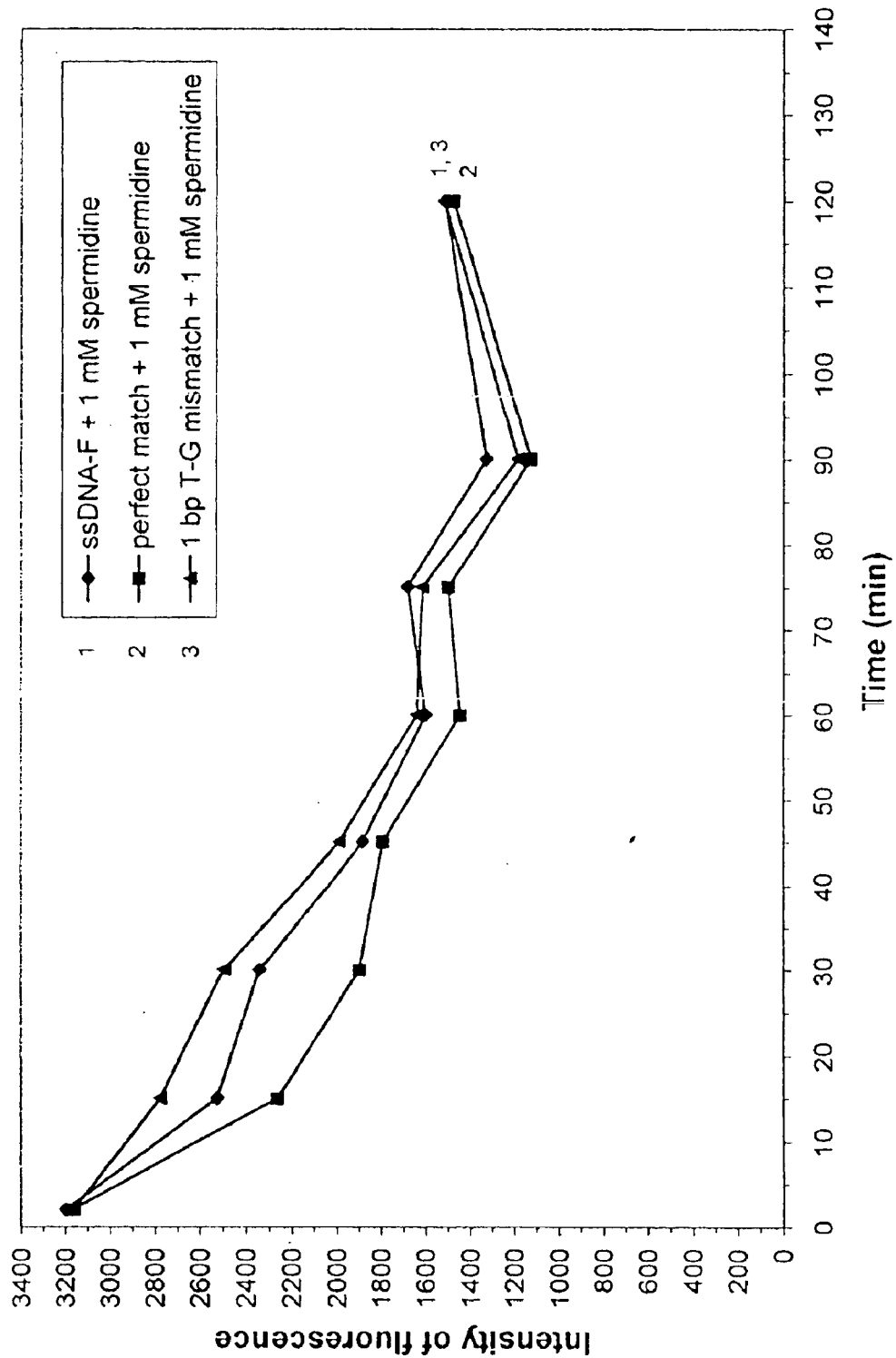
FIG. 10. Binding of 15-mer antiparallel ssDNA-F (2 pmole) (53% GC) and 50-mer dsDNA (0.2 pmole) in the presence of 1 mM spermidine over time

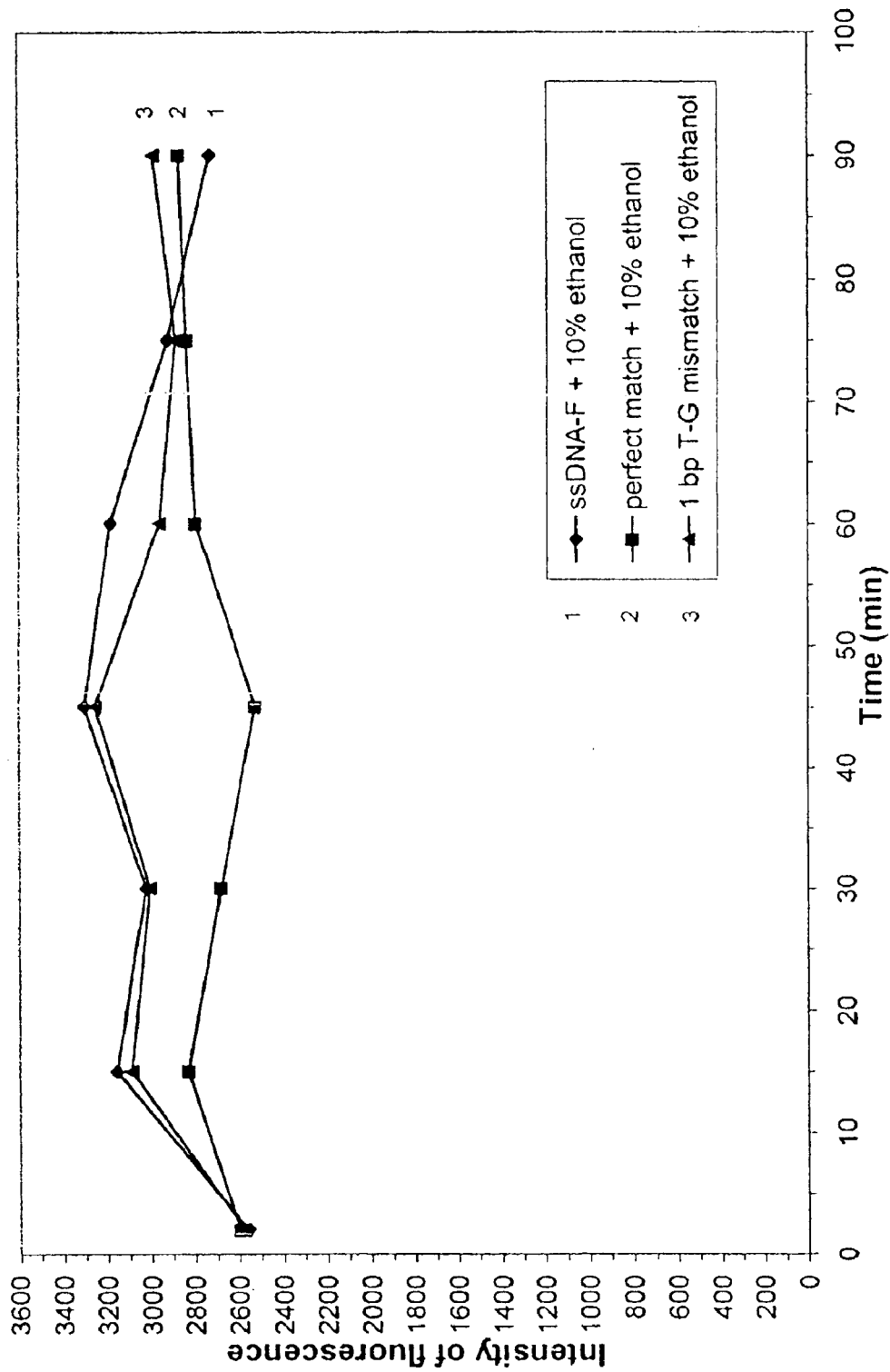
FIG. 11. Binding of 15-mer antiparallel ssDNA-F (2 pmole) (53% GC) and 50-mer dsDNA (0.2 pmole) in the presence of 10% ethanol over time

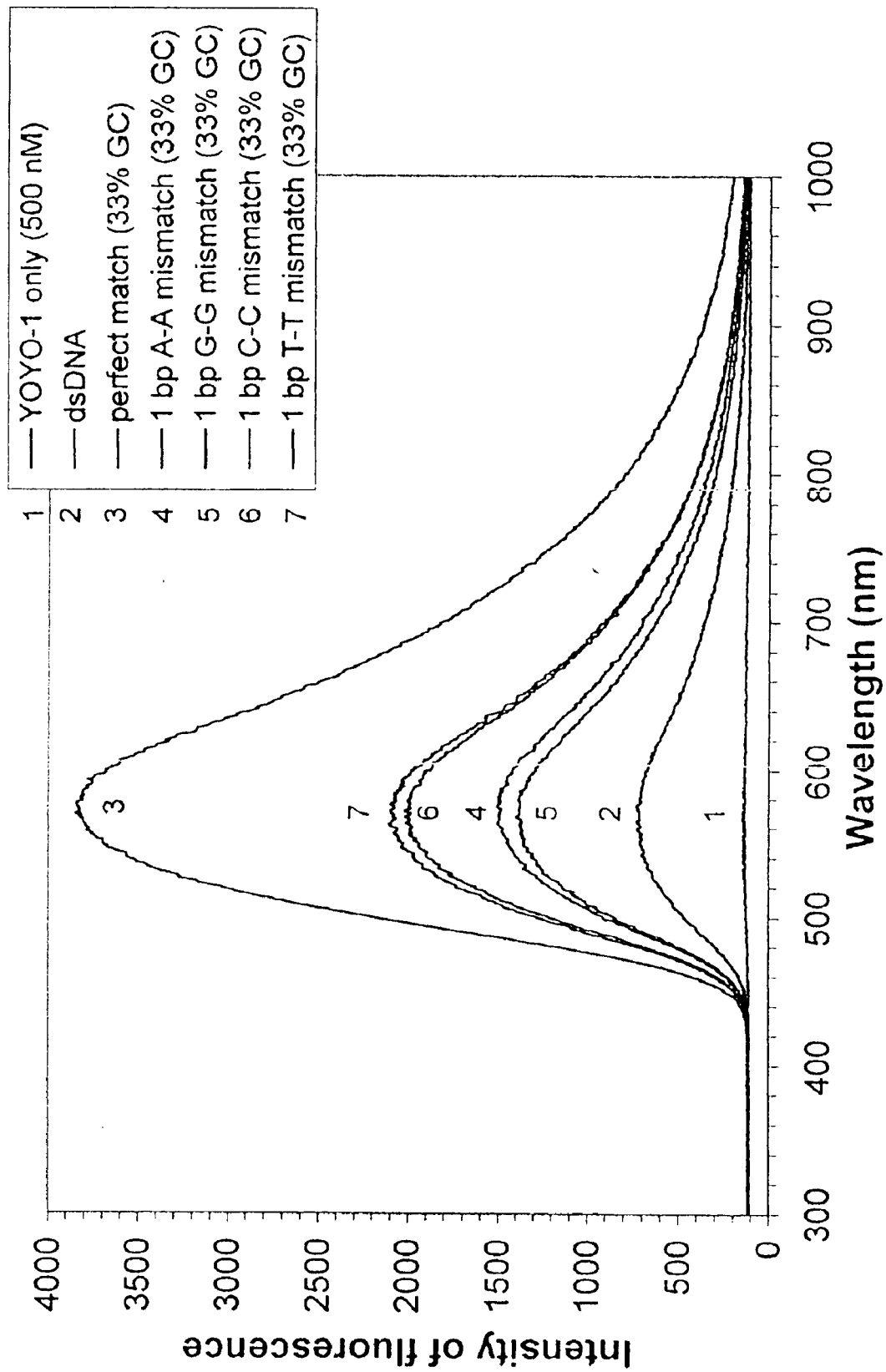

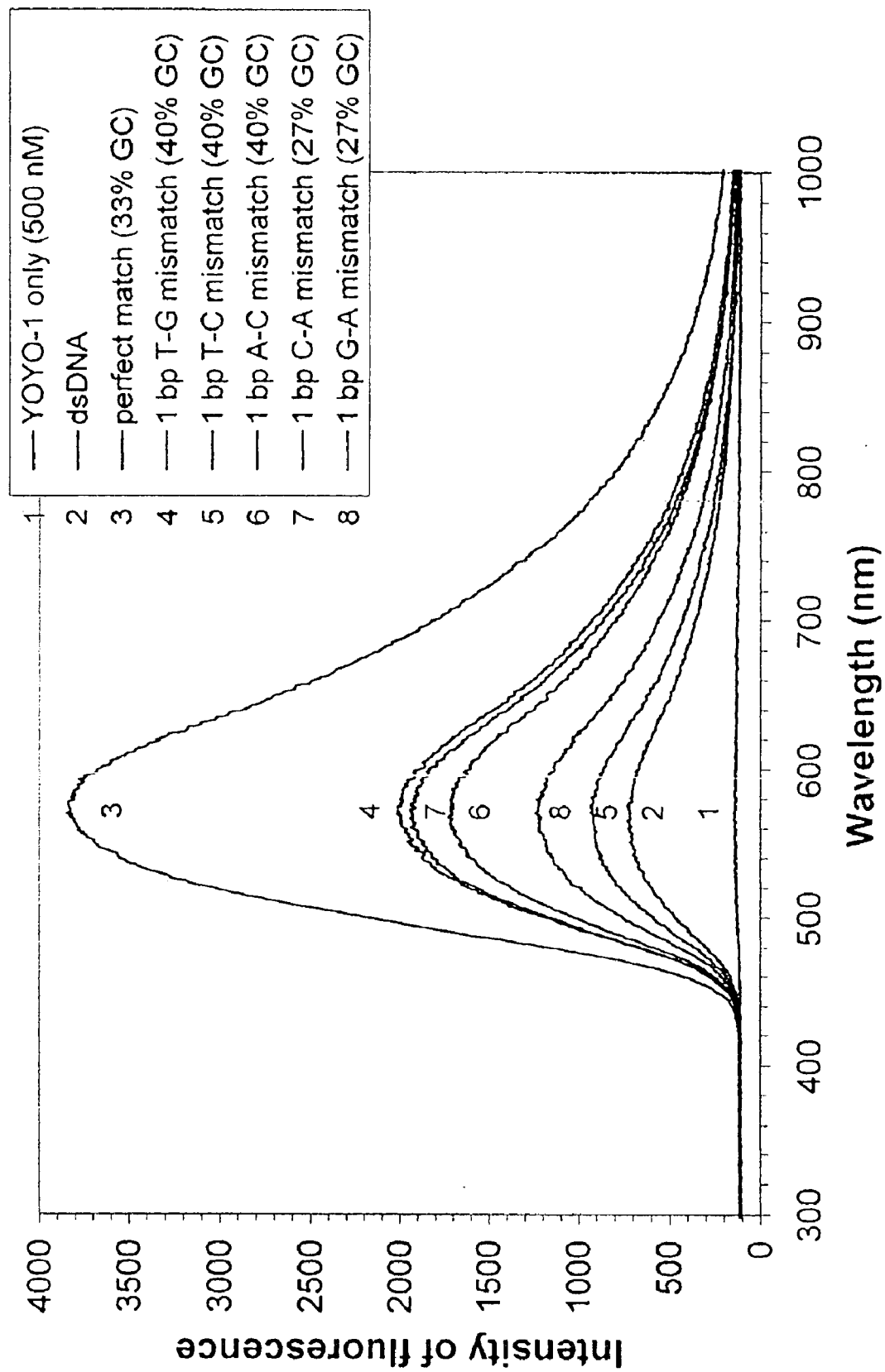
FIG. 12B. Binding of 15-mer antisense ssDNA to 50-mer dsDNA with YOYO-1

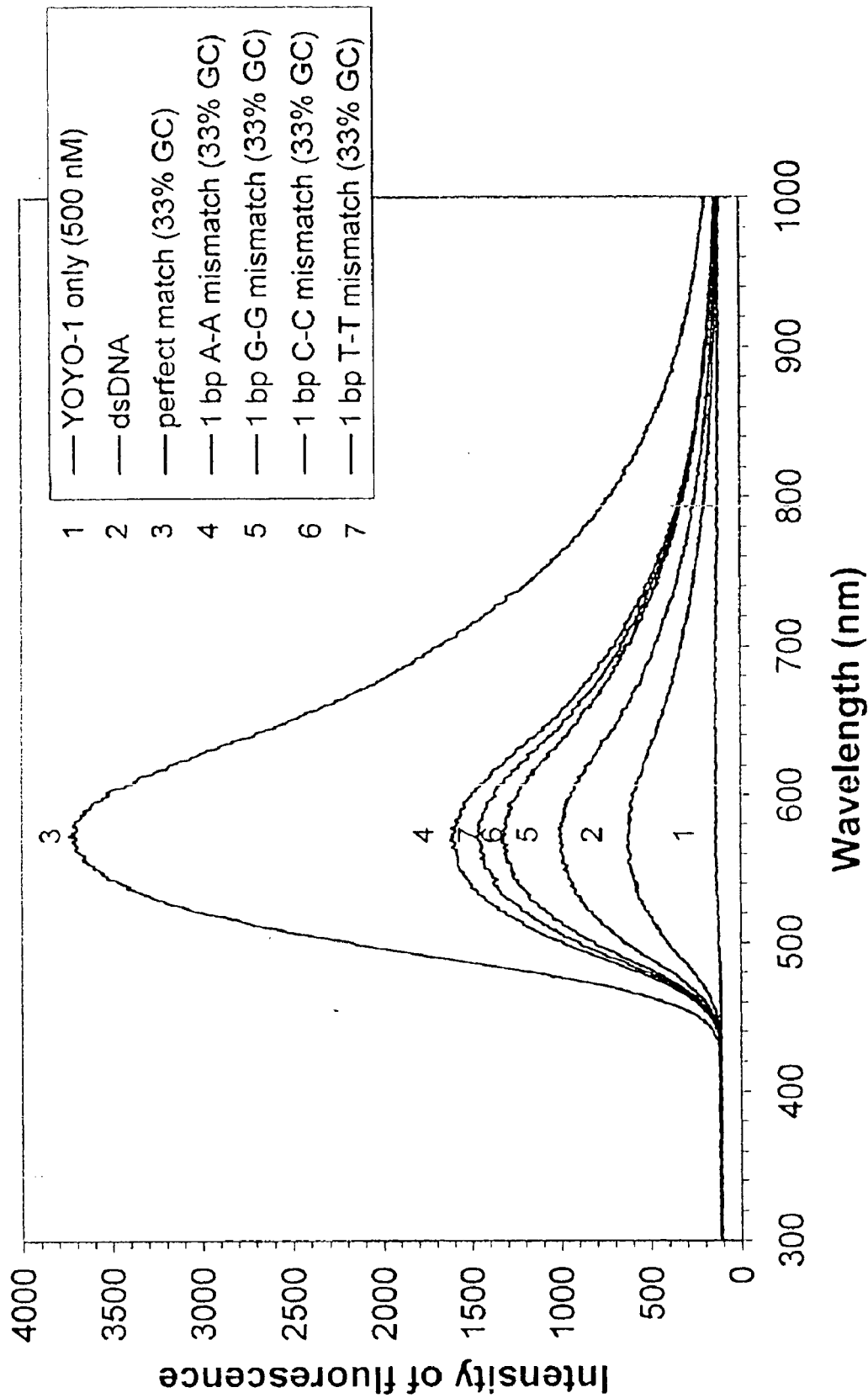
FIG. 12C. Binding of 15-mer sense ssDNA to 50-mer dsDNA with YOYO-1

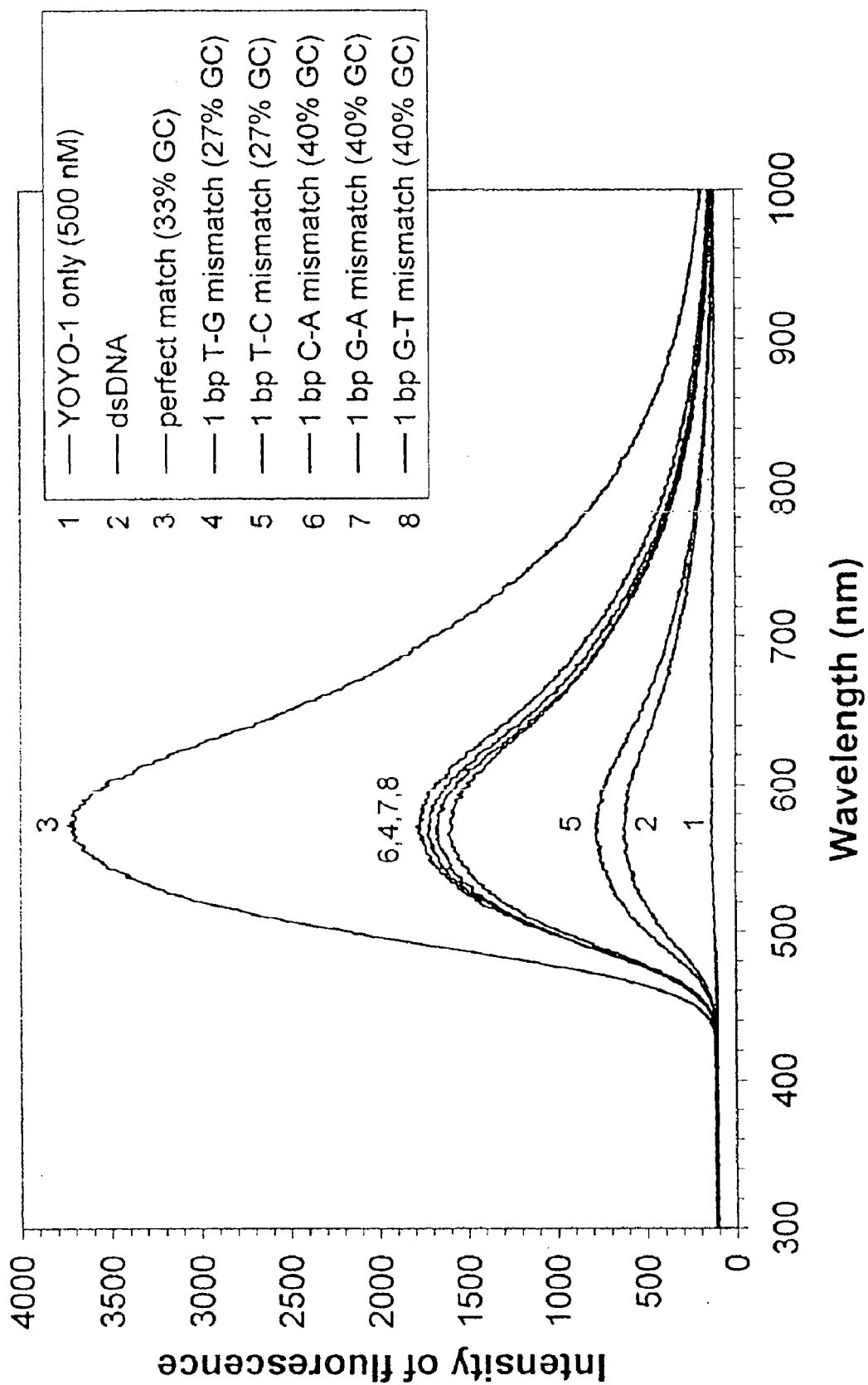

SEQUENCE LISTING

```
<160> NUMBER OF SEQ ID NOS: 15

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 1
tggcaccatt aaagaaaata tcatctttgg tgtttcctat gatgaatata              50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 2
tggcaccatt aaagaaaata tcgtctttgg tgtttcctat gatgaatata              50

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 3
tggcaccatt aaagaaaata tactctttgg tgtttcctat gatgaatata              50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 4
tggcaccatt aaagaaaata tacgctttgg tgtttcctat gatgaatata              50

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene
```

-continued

```
<400> SEQUENCE: 5
tggcaccatt aaagaaaata tcattggtgt ttcctatgat gaatata                    47

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 6
gagcaccatg acagacactg tcatctctgg tgtgtcctac gatgactctg                 50

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 7
gagcaccatg acagacactg tcatctttgg tgtgtcctac gatgactctg                 50

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 8
gagcaccatg acagacactg tcgtctctgg tgtgtcctac gatgactctg                 50

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 9
gagcaccatg acagacactg tcttctctgg tgtgtcctac gatgactctg                 50

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 10
gagcaccatg acagacactg tcatccctgg tgtgtcctac gatgactctg                 50

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 11
```

```
gagcaccatg acagacactg tcatcgctgg tgtgtcctac gatgactctg          50

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 12
gagcaccatg acagacactg tactctctgg tgtgtcctac gatgactctg          50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 13
gagcaccctc ccaggcacgg tcgtccctgg tgcgacctcc gacgagcgtg          50

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 14
gagcaccctc ccaggcacgg tcatccctgg tgcgacctcc gacgagcgtg          50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: variant of
      sequence derived from exon 10 of the human cystic fibrosis gene

<400> SEQUENCE: 15
gagcaccctc ccaggcacgg tattccctgg tgcgacctcc gacgagcgtg          50
```

NUCLEIC ACID MULTIPLEX FORMATION

CROSS-REFERENCE TO RELATED APPLICATIONS

This application is a continuation-in-part of U.S. patent application Ser. No. 09/664,827, filed Sep. 19, 2000 and is also a continuation-in-part of U.S. patent application Ser. No. 09/613,263, filed Jul. 10, 2000 now U.S. Pat. No. 6,420,115 which in turn is a continuation-in-part of U.S. patent application Ser. No. 09/468,679, filed Dec. 21, 1999 now U.S. Pat. No. 6,403,313. All of said patent applications are incorporated by reference herein in their entirety.

SPECIFICATION

BACKGROUND OF THE INVENTION

1. Field of Invention

The invention relates to nucleic acid multiplexes, and more particularly to methods of creating them as triplexes and quadruplexes, and furthermore employing them in assays to detect specific nucleic acids.

2. Description of Related Art

The ability of two single-stranded nucleic acid molecules of complementary base sequence to bind specifically to each other has provided the basis for both powerful research and powerful diagnostic tools. Less fully explored than such "conventional hybridization" has been the ability of single stranded molecules to bind to double-stranded targets and the ability of double-stranded molecules to bind to double-stranded targets. The ability to bind to double-stranded targets potentially has advantages over conventional hybridization. These could stem in part from the fact that the double-stranded target would not be denatured, allowing "milder" hybridization conditions and providing a target less prone to becoming a totally random coil. They could also stem in part from the fact that the base-pairing mechanisms would be at least partially different than in conventional hybridization, allowing the possibility for more favorable kinetics and a reduction in the amount of probe needed in the hybridization reaction mixture.

Prior work on creating multiplexes have included:

1) The formation of triplexes as part of the homologous recombination process, a process mediated by the bacterial protein RecA and proteins of similar function in other organisms;

2) The creation of 3-stranded structures during in situ hybridization (e.g., U.S. Pat. No. 5,707,801 of Bresser et al.); and 3) 3-stranded or 4-stranded complexes that rely on Hoogstein-type bonding.

This prior work does not fully exploit the potential for forming multiplexes. The RecA-mediated process requires a protein. The in situ hybridization processes are based on the principle that the double-stranded intracellular target will locally open its double-stranded structures, providing a single-stranded target that will hybridize according to conventional hybridization principles. Complexes reported to rely on Hoogstein-type polymers are limited to structures that are not true heteropolymers. Rather they require that a given strand be a polypurine or polypyrimidine or very close thereto. See, e.g., Floris et al., "Effect of cations on purine-purine-pyrimidine triple helix formation in mixed-valence salt solutions," 260 Eur. J. Biochem. 801–809 (1999).

As was the case with triplex nucleic acids, the conventional wisdom regarding quadruplex nucleic acids has been that such peculiar structures only exist under relatively extreme conditions for a relatively narrow class of nucleic acids. In particular, Sen et al. (Nature 334:364–366 (1988)) disclosed that guanine-rich oligonucleotides can spontaneously self-assemble into four-stranded helices in vitro. Sen et al. (Biochemistry 31:65–70 (1992)) disclosed that these four-stranded complexes can further associate into superstructures composed of 8, 12, or 16 oligomers.

Marsh et al. (Biochemistry 33:10718–10724 (1994), and Nucleic Acids Research 23:696–700 (1995)) disclosed that some guanine-rich oligonucleotides can also assemble in an offset, parallel alignment, forming long "G-wires". These higher-order structures are stabilized by G-quartets that consist of four guanosine residues arranged in a plane and held together through Hoogsteen base pairings. According to Sen et al. (Biochemistry 31:65–70 (1992)), at least three contiguous guanines within the oligomer are critical for the formation of these higher order structures.

It has been suggested that four-stranded DNAs play a role in a variety of biological processes, such as inhibition of HIV-1 integrase (Mazumder et al., Biochemistry 35:13762–13771 (1996)), formation of synapsis during meiosis (Sen et al., Nature 334:364–366 (1988)), and telomere maintenance (Williamson et al., Cell 59:871–880 (1989)); Baran et al., Nucleic Acids Research 25:297–303 (1997)).

It has been further suggested that controlling the production of guanine-rich quadruplexes might be the key to controlling such biological processes. For example, U.S. Pat. No. 6,017,709 to Hardin et al. suggests that telomerase activity might be controlled through drugs that inhibit the formation of guanine quartets.

U.S. Pat. No. 5,888,739 to Pitner et al. discloses that G-quartet based quadruplexes can be employed in an assay for detecting nucleic acids. Upon hybridization to a complementary oligonucleotide, the G-quartet structure unfolds or linearizes, thereby increasing the distance between a donor and an acceptor on different parts of the G-quartet structure, resulting in a decrease in their interaction and a detectable change in a signal (e.g., fluorescence) emitted from the structure.

U.S. Pat. No. 5,912,332 to Agrawal et al. discloses a method for the purification of synthetic oligonucleotides, wherein the synthetic oligonucleotides hybridize specifically with a desired, full-length oligonucleotide and concomitantly form a multimer aggregate, such as quadruplex DNA. The multimer aggregate containing the oligonucleotide to be purified is then isolated using size-exclusion techniques.

Despite the foregoing developments, the full potential of quadruplex nucleic acid has neither been fully appreciated nor fully exploited.

Related to the problem of performing hybridization-type experiments with double-stranded targets is the means of detecting them. Fluorescent dyes have been used to detect and quantitate nucleic acids for decades. In their most basic form, fluorescent intensity-based assays have typically comprised contacting a target with a fluorophore-containing probe, removing any unbound probe from bound probe, and detecting fluorescence in the washed sample. Homogeneous assays improve upon such basic assays, in that the former do not require a washing step or the provision of a non-liquid phase support.

For example, U.S. Pat. No. 5,538,848 to Livak et al. and U.S. Pat. No. 4,220,450 to Maggio disclose homogeneous fluorescence-based assays of nucleotide sequences using oligonucleotide probes in solution. However, these patents require the use of a quenching agent in combination with a reporting agent, so as to distinguish between the signals generated by hybridized probes and unhybridized probes. Livak et al. also requires the use of enzymes in its disclosed method. Quenching agents and enzymes add complexity and expense to the methods.

U.S. Pat. No. 5,332,659 to Kidwell discloses a method for detecting nucleotide sequences in solution using probes comprising at least two fluorophore moieties. The fluorophores must be selected to electronically interact with each other when close enough to vary the wavelength dependence of their spectra. Unhybridized probes are much more flexible than probes hybridized to the target sequence, and consequently the two fluorophore moieties on each probe are more likely to be close to each other when the probe is unhybridized than when the probe is hybridized. Thus, a change in emission wavelength correlated with free probe can be monitored as an indication of the amount of free probe in the sample.

U.S. Pat. No. 5,846,729 to Wu et al. also discloses homogeneous fluorescence-based assays for detecting nucleic acid.

In addition to the aforementioned developments which detect fluorescent intensity, some have touted the advantages of fluorescent polarization assays. However, there are significant drawbacks to polarization-based assays. The degree of change in polarization as a function of binding can be unpredictable, and interpretation of data to conform inconsistent data to theoretical expectations can require more effort than is desirable in an analytical method, particularly when the method is to be automated. There are as well constraints arising from the molecular weight of the molecules whose motion is being evaluated in a fluorescent polarization assay.

The present inventions will be seen, in various important embodiments to take advantage of the properties of fluorescent molecules for purposes of detecting triplexes and quadruplexes.

All references cited herein are incorporated herein by reference in their entireties.

BRIEF SUMMARY OF THE INVENTION

Methods of Creating Multiplexes

In one general aspect, the invention is a method of creating a nucleic acid multiplex, said method comprising the steps of:

1) creating a mixture comprising water, a Watson-Crick duplex, a sufficient number of single-stranded mixed base sequence molecules to form a multiplex that includes the Watson-Crick duplex, and an accelerator agent that increases a rate or amount of multiplex formation, said multiplex being a triplex or quadruplex, wherein said single-stranded molecule or molecules are selected so that, if in a multiplex, they would each be related to all other strands of the multiplex by adherence to base pairing rules, said rules being either Watson-Crick base-pairing rules or homologous binding base-pairing rules; and 2) incubating said mixture to allow the multiplex to form, each strand of said multiplex related to all other strands of the multiplex by adherence to base-pairing rules;

provided that, within the multiplex, the Watson-Crick duplex added in step (1) is heteropolymeric with a G-C content between 10% and 90%.

In one particular aspect of the method, the multiplex created is a triplex, in step (1) the sufficient number of single-stranded molecules is 1, and in step (2) the triplex is formed. In a particular embodiment of the method, in the triplex, the single-stranded molecule is related to one strand of the duplex by Watson-Crick base-pairing rules and to the second strand of the duplex by homologous binding base-pairing rules. In a further particular embodiment, the duplex substantially retains its double-helical structure and the single-stranded molecule resides in a groove of that double-helical structure. All such triplexes are also aspects of the invention.

In another particular aspect of the method, the multiplex created is a quadruplex, in step (1) the Watson-Crick duplex is a first Watson-Crick duplex, and in step (1) the sufficient number of single-stranded molecules is 2, those single-stranded molecules are in a second Watson-Crick duplex, and in step (2) the quadruplex is formed from said first and second duplexes. Preferably step (1) is done with the two single-stranded molecules already in the second Watson-Crick duplex.

Methods of Detecting a Triplex

The method of creating a triplex can be adapted to be a method for detecting a triplex by adding an additional step (3) in which the triplex is detected.

Methods of Detecting a Quadruplex

The method of creating a quadruplex can be adapted to be a method for detecting a quadruplex by adding an additional step (3) in which the quadruplex is detected.

Triplex

In another general aspect, the invention is a triplex (a triplex complex) comprising a single-stranded probe bound to a double-stranded nucleic acid target, wherein said probe comprises a heteropolymeric nucleic acid or a heteropolymeric nucleic acid analog, and all base triplets of said triplex are members selected from the group consisting of A-T-A, T-A-T, U-A-T, T-A-U, A-U-A, U-A-U, G-C-G and C-G-C.

Quadruplex:

In another aspect, the invention is a multiplex structure that is a quadruplex, the quadruplex comprising:

a first strand containing a first sequence of nucleobases;

a second strand containing a second sequence of nucleobases, wherein said second strand is associated with said first strand by Watson-Crick bonding;

a third strand containing a third sequence of nucleobases; and a fourth strand containing a fourth sequence of nucleobases, wherein said fourth strand is associated with said second strand and said third strand by Watson-Crick bonding.

BRIEF DESCRIPTION OF THE DRAWINGS

The invention will be described in conjunction with the following drawings in which like reference numerals designate like elements and wherein:

FIGS. 1, 2A and 2B show the intensity of fluorescence as a function of temperature, GC content, and extent of base pair matching.

FIGS. 3, 4, 5A, 5B, 5C and 5D show the intensity of fluorescence as a function of wavelength, extent of base pair matching and cation.

FIGS. 6A, 6B, and 6C show intensity of fluorescence as a function of lasing protocol, and cation.

FIGS. 7A, 7B, 7C, 8A, 8B, 9A, 9B, 9C, and 10 show, as regards quadruplexes, the intensity of fluorescence as a function of the extent of base pair matching and cation.

FIG. 11 shows the intensity of fluorescence as a function of the extent of base pair matching in a solution containing ethanol.

FIG. 12 shows the intensity of fluorescence as a function of wavelength for perfect and imperfect base pair matches in dsDNA:ssDNA complexes when the cationic DNA intercalator YOYO-1 is present.

DETAILED DESCRIPTION OF THE INVENTION

Glossary and Definitions

The one-letter codes for the bases that form part of their respective nucleotides are: A: adenine; T: thymine; G: guanine; C: cytosine; U: uracil. These letters are also used to represent their respective nucleotides.

The G-C content of a duplex is the 100 times the number of G-C base pairs divided by the sum of the number of G-C base pairs plus the number of A-T (or A-U) base pairs and is expressed as a percentage (e.g., 20%).

An accelerator agent is understood here as one that "increases a rate or amount of said triplex or quadruplex formation." A rate can be obtained with as few as two measurements, each at different time points. Amounts refer to the number of triplexes or quadruplexes formed.

The term "accelerator agent" is used interchangeably with the terms "promoter" and "promoter agent" except where the promoter specifically refers to a gene promoter.

The terms nucleic acid, triplex, quadruplex, and the like are intended to refer to molecules that comprise DNA, RNA, and analogues thereof capable of forming similar structures such as Watson-Crick duplexes, and the triplexes and quadruplexes formed herein.

"Nucleobase" refers to the bases A, U, G, C, T, and those analogs that can conform to Watson-Crick base-pairing rules.

Analogues of A,U,G,C, and T are those analogues that can conform to Watson-Crick base pairing rules.

A Watson-Crick duplex is a 2-stranded molecule or molecular segment in which the two strands are anti-parallel, their 5'→3' directions being opposite. The overall structure of the duplex is that of a double helix. The strands are held together by hydrogen bonds and hydrophobic interactions. There is base pair complementarity, A is paired with T by two hydrogen bonds (or, in the case of RNA, A is paired with U) and G is paired with C by three hydrogen bonds. As a result, the base-pairing rules are: A is paired with T, A is paired with U, and G is paired with C.

A 3-stranded nucleic acid molecule is not necessarily a triplex and it is not necessary that any segment of a 3-stranded molecule be a triplex. It is possible that, at no region within any strand, is that strand bonded to more than one other strand. A simple example would be a Y-shaped molecule where Strands 1 and 2 form the stem, Strands 1 and 3 form the left upper branch, and Strand 2 forms a single-stranded right upper branch.

An example of a triplex is a 3-stranded nucleic acid molecule or molecular segment in which one strand (arbitrarily named Strand 1) follows the Watson-Crick base-pairing rules (A-T, A-U, and G-C) with both Strand 2 and Strand 3. Strands 1 and 2 form a structure that is, or is close to, that of a Watson-Crick duplex. Strand 3 resides in the major groove of that duplex. An example of such a triplex is the one elaborated by V. B. Zhurkin et al, J. Mol. Biol., (1994) vol. 239, 181–200 (See especially FIG. 2 of that reference), which article is incorporated herein by reference. As part of the stabilization of such a triplex, Strand 3 is bonded to the other two strands by base pairing rules as follows:

An A on Strand 3 is paired with both an A on Strand 1 and a T on Strand 2;

a G on Strand 3 is paired with both a G on Strand 1 and a C on Strand 2;

a C on Strand 3 is paired with both a C on Strand 1 and a G on strand 2; and a T on strand 3 is paired with both a T on Strand 1 and an A on strand 2.

These base pairing rules are satisfied regardless of which variant (C or C+ or C', T or T') of the Zhurkin model is considered;

The term "base-pairing rules" are those that define the specificity between one nucleic acid molecule and another nucleic acid molecule when the two bind to each other with specificity. Examples are Watson-Crick base pairing rules (G-C, and A-T or A-U) and homologous binding base-pairing rules (A-A, T-T, G-G, C-C, U-U).

"Decondensation" of a duplex is defined as an increase in the overall helical repeat length of the duplex. For example, the B conformation of the duplex has an overall helical repeat length of 10 base pairs; a decondensation of 106° results in that repeat length being 13 base pairs.

PNA stands for polyamide analogs of DNA and RNA (see e.g., U.S. Pat. No. 5,539,082 to Nielsen et al.)

Specific Embodiments and Alternative Formulations of the Inventions

The inventions as described in the Summary of The Invention section have specific embodiments and preferred embodiments of interest. These embodiments are described throughout this application. However, for convenience, many of them are summarized in this section. Similarly, the inventions as summarized in the Summary of Invention section can be phrased in alternative fashions expressing some variation of the invention but retaining substantial overlap as to the essential invention. Such alternative formulations of the invention are also included in this section.

(A) Methods of Making the Multiplexes

The methods of forming the triplex or quadruplex, described generally in the Summary of the Invention section, can optionally be performed by incorporating one or more of the following into the method:

within the multiplex, the Watson-Crick duplex added in step (1) is heteropolymeric with a G-C content between 25% and 75%;

within the multiplex, the Watson-Crick duplex added in step (1) is heteropolymeric with a G-C content between 10% and 90%, and furthermore the combined frequencies therein of purine-pyrimidine dimers and pyrimidine-purine dimers exceeds 25% (dimers are identified starting at the 5' end of the sequence and progressing one base at a time until the 3' end is reached; for example, the sequence 5'-AAAGGGT has one purine-pyrimidine dimer (GT) and no pyrimidine-purine dimers—their combined frequencies equal 1/6);

performing steps (1) and/or (2) with the nucleic acid strands and/or duplexes not in a cell (and not in a virus);

performing step (2) without the assistance of a protein (such as recA or protein of similar function);

in step (1), adding the water so that it accounts, on a volume basis, for at least 50 percent of the final volume of the mixture (more preferably for at least 80% of the final volume, most preferably in step (1) water is the only liquid added to the mixture);

in step (1), not adding any protein;

performing step (2) at a temperature or temperatures above the freezing temperature of the aqueous solution and at not more than 85° C. (more preferably between 5° C. and 30° C., most preferably between 15° C. and 25° C.)

in step (1), adding an anion or, more preferably, a cation as the accelerator agent (monovalent, divalent or multivalent; for example, a metallic cation or a cationic peptide); wherein said cation is at least one member selected from the group consisting of alkali metal cations, alkaline earth metal cations, transition metal cations, $Co(NH_3)_6^{+3}$, trivalent spermidine and tetravalent spermine;

wherein said cation is $Na^+$ provided at a concentration of 50 mM to 125 mM;

wherein said cation is selected from the group consisting of $Mn^{+2}$ provided at a concentration of 10 mM to 45 mM, $Mg^{+2}$ provided at a concentration of 10 mM to 45 mM, and $Ni^{+2}$ provided at a concentration of 20 mM;

in step (1) adding an intercalator as an accelerator agent (especially a fluorescent intercalator; preferably a bis-intercalator);

in step (1) said accelerator agent is an intercalating fluorophore selected from the group consisting of YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, cyanine monomers, ethidium bromide, ethidium homodimer-1, ethidium homodimer-2, ethidium derivatives, acridine, acridine orange, acridine derivatives, ethidium-acridine heterodimer, ethidium monoazide, propidium iodide, SYTO dyes, SYBR Green 1, SYBR dyes, Pico Green, SYTOX dyes, and 7-aminoactinomycin D.

in step (1) said accelerator agent is a non-intercalating fluorophore (especially one selected from the group consisting of biotin, rhodamine, Alexa dyes, BODIPY dyes, biotin conjugates, thiol-reactive probes, fluorescein and derivatives (including the "caged" probes), Oregon Green, Rhodamine Green, QSY dyes)) and said intensity is inversely correlated with formation of the triplex or quadruplex;

in step (1) said accelerator agent is tethered to at least one of said first strand, said second strand, said third strand and said fourth strand;

in step (1) adding an accelerator agent that is an intercalator that binds to the minor groove of the Watson-Crick duplex (or at least one of the two Watson-Crick duplexes);

in step (1) adding an accelerator agent (especially an organic liquid soluble in water, such as dimethyl formamide, ethanol, and glycerol) that at 25° C. is a liquid;

in step (1) adding more than one accelerator agent;

in step (1) adding an accelerator agent that is a condensation or decondensation agent as regards the Watson-Crick duplex;

in step (1) adding an accelerator agent that is an analog of A, T, U, C, or G;

in step (1) adding an accelerator agent selected from the group consisting of lectins and polysaccharides;

in steps (1) and (2), buffering the mixture with a pH of about 5 to about 9;

one cytosine in at least one C-G-C or G-C-G base triplet is positively charged;

one cytosine in each C-G-C and G-C-G base triplet is positively charged;

in step (2) the incubation time is not more than about two hours (more preferably not more than 1 hour; and within either time frame, preferably at least 25%, more preferably at least 50%, of the possible multiplexes have been formed);

said at least one accelerator agent is a minor groove nucleic acid binding molecule, which binds in a non-intercalating manner and binds with an association constant of at least $10^3$ $M^{-1}$;

wherein the multiplex is part of an electrical circuit. (Alternatively, the invention is an electrical circuit comprising the multiplex structure.)

It will be apparent to someone of ordinary skill in the art that the foregoing specific conditions also apply to the following method for making a quadruplex.

In an alternatively phrased version, the method of forming the quadruplex comprises:

(1) providing a hybridization medium comprising a first strand, a second strand, a third strand, a fourth strand, water, a buffer and at least one accelerator agent; and (2) incubating said hybridization medium for an incubation time effective to hybridize said second strand to said fourth strand to provide said multiplex structure wherein said multiplex structure comprises:

a first strand containing a first sequence of nucleobases;

a second strand containing a second sequence of nucleobases, wherein said second strand is associated with said first strand by Watson-Crick bonding;

a third strand containing a third sequence of nucleobases; and a fourth strand containing a fourth sequence of nucleobases, wherein said fourth strand is associated with said second strand and said third strand by Watson-Crick bonding.

In particular embodiments of the methods of forming a quadruplex, the following apply alone or in combination (the descriptions that follow utilize the terminology of the method of making a quadruplex that specifies 4 separate strands but they are also applicable to the method that specifies a Watson-Crick duplex as one or two of the starting materials):

at least one of said first strand and said second strand further comprises a pharmaceutical agent, and hybridization of said second strand to said fourth strand places said pharmaceutical agent an effective distance from a target on said third strand, said fourth strand or on another molecule associated with at least one of said third strand and said fourth strand;

said pharmaceutical agent is a member selected from the group consisting of nucleic acids designed to bind gene promoter sequences of clinically relevant genes, nucleic acids designed to bind clinically relevant genes, and nucleic acids designed to bind origin-of-replication sites of pathogens;

said third strand and said fourth strand are provided in said hybridization medium before said first strand and said second strand, and said first strand and said second strand are provided in dehydrated form prior to rehydration by contact with said hybridization medium;

at least one of said first strand and said second strand is covalently labeled with a non-intercalating fluorophore and said intensity is inversely correlated with said binding affinity;

at least one accelerator agent is an intercalating fluorophore, and a fluorescent intensity of a test medium containing said multiplex structure is directly correlated with a binding affinity of said second strand for said fourth strand;

hybridization of said second strand to said fourth strand is detected as a change in a fluorescent, chemiluminescent, electrochemiluminescent or electrical signal;

an intensity of said signal is correlated with a binding affinity between said second strand and said fourth strand;

hybridization of said second strand to said fourth strand inactivates an activity associated with at least one of said third strand and said fourth strand.

(B) Methods Of Detecting Triplexes

The methods of detecting a triplex, described generally in the Summary of the Invention section, can optionally be performed by incorporating one or more of the following into the method:

carrying out the method as a homogenous assay such that, during or prior to step (3), single-stranded molecules that are not part of the triplex are not placed in a vessel or container separate from that containing the triplex;

using the detection method to discriminate between a perfect base-pairing-rules match, a one-base mismatch (or deletion), and a 2-base mismatch (or deletion), between the duplex and the single-stranded molecule in the triplex (the method preferably comprising calibrating the method with molecules comprising known mismatches);

using the extent of binding of an intercalator (e.g., as indicated by increased fluorescence) as an indication of the formation of the triplex;

such that a wavelength at which said intercalating fluorophore fluoresces shifts to a second wavelength upon intercalation, a difference between said wavelength and said second wavelength indicating whether a complex between said probe and said target is a duplex or a triplex and whether said target is DNA or RNA;

the probe is covalently labeled with a non-intercalating fluorophore and said intensity is inversely correlated with said binding affinity (especially wherein said non-intercalating fluorophore is a member selected from the group consisting of biotin, rhodamine and fluorescein);

using a fluorophore-labeled single stranded molecule as the single-stranded molecule;

the method is a homogeneous assay conducted without providing a signal quenching agent on said target sequence (i.e., in the duplex) or on said probe (i.e., the single-stranded molecule) and/or without prior denaturation of said target sequence and/or without PCR amplification of said target sequence;

said method is a homogeneous assay conducted without providing a signal quenching agent on said target sequence or on said probe;

the probe has a partially charged or uncharged backbone;

the probe comprises a PNA sequence and/or is ssPNA prepared by parallel synthesis;

the probe and said target sequence are the same length;

the probe is 5 to 30 nucleotides long;

the fluorescence-exciting radiation is emitted from an argon ion laser at a wavelength from about 200 nm to about 1000 nm;

the test sample has a volume of about 20 microliters containing about 10 femtomoles of target sequence and about 10 femtomoles of probe;

the concentration of the target sequence in said sample is not more than $5 \times 10^{-10}$ M;

the concentration of the probe in the sample is not more than $5 \times 10^{-10}$ M;

the method is conducted on a biochip;

the intercalating fluorophore is added to the medium in a form free of said probe and free of said target sequence;

the intercalating fluorophore is a member selected from the group consisting of YOYO-1, TOTO-1, ethidium bromide, ethidium homodimer-1, ethidium homodimer-2 and acridine.

In an alteratively phrased aspect, the invention is a detection method comprising:

providing a target double-stranded nucleic acid or nucleic acid analogue comprising a target sequence, wherein said target sequence contains at least one purine base and at least one pyrimidine base;

providing a probe comprising a nucleic acid sequence or a nucleic acid analog sequence;

providing an accelerator agent;

adding said probe, said target sequence and said accelerator agent to a medium to provide a test sample containing a triplex complex comprising said probe bound to said target sequence, wherein all base triplets of said complex are members selected from the group consisting of A-T-A, T-A-T, U-A-T, T-A-U, A-U-A, U-A-U, G-C-G and C-G-C;

irradiating said test sample with exciting radiation to cause the test sample to emit fluorescent radiation;

detecting an intensity of said fluorescent radiation, wherein said intensity is correlated with a binding affinity between said probe and said target sequence; and determining from said intensity an extent of matching between said probe and said target sequence.

In another alternatively phrased related aspect, the method comprises:

providing a target nucleic acid or nucleic acid analogue having a target sequence, wherein said target sequence contains at least one purine base and at least one pyrimidine base;

providing a double-stranded probe comprising a nucleic acid sequence or a nucleic acid analog sequence;

providing a hybridization accelerator agent;

adding said probe, said target and said hybridization accelerator agent to a medium to provide a test sample containing a Watson-Crick triplex comprising said probe bound to said target sequence;

irradiating said test sample with exciting radiation to cause test sample to emit fluorescent radiation;

detecting an intensity of said fluorescent radiation, wherein said intensity is correlated with a binding affinity between said probe and said target sequence; and determining from said intensity an extent of matching between said probe and said target sequence wherein said method is a homogeneous assay conducted without providing a signal quenching agent on said target sequence or on said probe;

(C) Methods of Detecting Quadruplexes

The methods of detecting a quadruplex, described generally in the Summary of the Invention section, can optionally be performed by incorporating one or more of the following into the method:

carrying out the method as a homogenous assay, such that during or prior to step (3) nucleic acid molecules that are not part of the quadruplex are not placed in a vessel or container separate from that containing the quadruplex;

the method is a homogeneous assay conducted without providing a signal quenching agent on said target sequence or on said probe (i.e., the second Watson-Crick duplex) and/or without prior denaturation of said target sequence and/or without PCR amplification of said target sequence;

using the detection method to discriminate between a perfect base-pairing-rules match, a one-base mismatch (or deletion), and a 2-base mismatch (or deletion), between the first and second Watson-Crick duplexes (preferably by calibrating the method with molecules comprising known mismatches);

using the extent of binding of an intercalator as an indication of the formation of the quadruplex (especially by using a fluorescent intercalator and using increased fluorescence as an indicator);

the intercalating fluorophore is added to the medium in a form free of said probe and free of said target sequence;

the intercalating fluorophore is a member selected from the group consisting of YOYO-1, TOTO-1, ethidium bromide, ethidium homodimer-1, ethidium homodimer-2 and acridine;

a wavelength at which said intercalating fluorophore fluoresces shifts to a second wavelength upon intercalation, a difference between said wavelength and said second wavelength indicating whether a complex between said probe and said target is a duplex or a triplex and whether said target is DNA or RNA;

the probe is covalently labeled with a non-intercalating fluorophore and said intensity is inversely correlated with said binding affinity (especially wherein said non-intercalating fluorophore is a member selected from the group consisting of biotin, rhodamine and fluorescein);

using a fluorophore-labeled single stranded molecule for part of the second Watson-Crick duplex;

the method further comprises quantifying the binding affinity;

the probe has a partially charged or uncharged backbone;

the probe comprises a PNA sequence and/or is ssPNA prepared by parallel synthesis;

the probe and said target sequence are the same length;

the probe is 5 to 30 nucleotides (or base pairs) long;

the fluorescence-exciting radiation is emitted from an argon ion laser at a wavelength from about 200 nm to about 1000 nm;

the test sample has a volume of about 20 microliters containing about 10 femtomoles of target sequence and about 10 femtomoles of probe;

the concentration of the target sequence in said sample is not more than $5 \times 10^{-10}$ M;

the concentration of the probe in the sample is not more than $5 \times 10^{-10}$ M;

a ratio of said first strand and said second strand to said third strand and said fourth strand is about 10:1;

concentrations of each of said first strand, said second strand, said third strand and said fourth strand are not more than $5 \times 10^{-10}$ M;

the method is conducted on a biochip.

In an alternatively phrased related aspect, the method comprises:

providing a target nucleic acid or nucleic acid analogue having a target sequence, wherein said target sequence contains at least one purine base and at least one pyrimidine base;

providing a double-stranded probe comprising a nucleic acid sequence or a nucleic acid analog sequence;

providing a hybridization accelerator agent;

adding said probe, said target and said hybridization accelerator agent to a medium to provide a test sample containing a Watson-Crick quadruplex comprising said probe bound to said target sequence;

irradiating said test sample with exciting radiation to cause test sample to emit fluorescent radiation;

detecting an intensity of said fluorescent radiation, wherein said intensity is correlated with a binding affinity between said probe and said target sequence; and determining from said intensity an extent of matching between said probe and said target sequence wherein said method is a homogeneous assay conducted without providing a signal quenching agent on said target sequence or on said probe.

(D) The Triplexes

The triplex described generally in the Summary of the Invention section, can optionally have one or more of the following features:

each strand is heteropolymeric with a G-C content between 25% and 75%;

each strand is heteropolymeric with a G-C content between 10% and 90%, and furthermore the combined frequencies therein of purine-pyrimidine dimers and pyrimidine-purine dimers exceeds 25%;

it is not in a cell (and not in a virus);

it is stable at pH greater than 7.6 (but less than pH 9);

it is in a medium at a pH greater than 7.6 (and preferably less than pH 9);

the single-stranded nucleic acid or nucleic acid analog is 5 to 30 bases long and the double-stranded nucleic acid target is 8 to $3.3 \times 10^9$ base pairs long;

the target sequence is heteropolymeric and contains 25% to 75% purine bases and 75% to 25% pyrimidine bases in any order (preferably wherein the frequency of purine-pyrimidine dimers plus the frequency of pyrimidine-purine dimers exceeds 25%);

the probe (i.e, the single-stranded molecule) is covalently bound to a double-stranded nucleic acid cleaving agent;

the probe is covalently bound to a chemotherapeutic agent;

the probe is covalently bound to a label (for example, a multi-molecule signaling complex, a redox pair, a chemiluminescent agent, an electrochemiluminescent agent, or in a preferred embodiment, a fluorophore, especially such that the fluorescent intensity of the complex is correlated with a binding affinity between the probe and the target sequence);

the base pairing rules for the single-stranded nucleic acid molecule are, as regards one strand of the duplex, the Watson-Crick base-pairing rules, G-C and either A-T or A-U, and, as regards the other strand of the duplex are A-A and either T-T or U-U;

the duplex substantially retains its Watson-Crick double helical structure, and the single-stranded molecule resides in a groove of the double helix;

the accelerator agent forms a bond between part of the duplex and part of the single-stranded nucleic acid molecule;

the accelerator agent is covalently linked to the single-stranded nucleic acid molecule;

both strands of the Watson-Crick duplex are DNA (especially where all strands of the triplex are DNA);

the accelerator reagent binds to a base in the Watson-Crick duplex, said base being one to which a base in the single-stranded nucleic acid molecule binds;

the accelerator reagent binds to a base in the Watson-Crick duplex, said base not being one in the triplex;

the accelerator agent binds to the phosphate backbone of the Watson-Crick duplex;

the accelerator agent binds to more than one site on the Watson-Crick duplex, each site either on a base or a place on a phosphate backbone of said duplex;

the accelerator agent binds to one site on the Watson-Crick duplex, said site either on a base or on a phosphate backbone of said duplex;

the accelerator agent binds to a base in the Watson-Crick duplex and to a base in the single-stranded nucleic acid molecule;

the accelerator agent binds to a base in the single-stranded nucleic acid molecule.

(E) The Quadruplexes

The quadruplex described generally in the Summary of the Invention section, can optionally have one or more of the following features:

each of said four strands is heteropolymeric with a G-C content between 10% and 90%;

the second and fourth strands are aligned in a parallel 3' to 5' direction and binding between those 2 strands is according to homologous base-pairing rules;

the first and third strands are aligned in a parallel 5' to 3' direction and binding between those 2 strands is according to homologous base-pairing rules;

the second and fourth strands are aligned in a parallel 3' to 5' direction and binding between said second and fourth strands is according to homologous base-pairing rules and furthermore the first and third strands are aligned in a parallel 5' to 3' direction and binding between said first and third strands is according to homologous base-pairing rules;

the second and fourth strands are aligned in a parallel 3' to 5' direction and binding between those 2 strands is according to Watson-Crick base-pairing rules;

the first and third strands are aligned in a parallel 5' to 3' direction and binding between those 2 strands is according to Watson-Crick base-pairing rules;

the second and fourth strands are aligned in a parallel 3' to 5' direction and binding between said second and fourth strands is according to Watson-Crick base-pairing rules and furthermore the first and third strands are aligned in a parallel 5' to 3' direction and binding between said first and third strands is according to Watson-Crick base-pairing rules;

the first and fourth strands are aligned in anti-parallel 5' to 3' and 3' to 5' directions, respectively, and binding between the 2 strands is according to Watson-Crick base-pairing rules;

the second and third strands are aligned in anti-parallel 3' to 5' and 5' to 3' directions, respectively, and binding between those 2 strands is according to Watson-Crick base-pairing rules;

the first and fourth strands are aligned in anti-parallel 5' to 3' and 3' to 5' directions, respectively, and binding between said first and fourth strands is according to Watson-Crick base-pairing rules and furthermore the second and third strands are aligned in anti-parallel 3' to 5' and 5' to 3' directions, respectively, and binding between said second and third strands is according to Watson-Crick base-pairing rules;

the first and fourth strands are aligned in anti-parallel 5' to 3' and 3' to 5' directions, respectively, and binding between those 2 strands is according to homologous base-pairing rules;

the second and third strands are aligned in anti-parallel 3' to 5' and 5' to 3' directions, respectively, and binding between those 2 strands is according to homologous base-pairing rules;

the first and fourth strands are aligned in anti-parallel 5' to 3' and 3' to 5' directions, respectively, and binding between said first and fourth strands is according to homologous base-pairing rules and furthermore the second and third strands are aligned in anti-parallel 3' to 5' and 5' to 3' directions, respectively, and binding between said second and third strands is according to homologus base-pairing rules;

each interacting base of the said first strand interacts specifically with both the adjacent base on the said third strand and with the base on the said fourth strand, the base to which the said third strand base is bound;

each interacting base of the said second strand interacts specifically with both the adjacent base on the said fourth strand and the base on the said third strand, the base to which the said fourth strand base is bound;

it is an isolated, purified, artificial or synthetic quadruplex;

each strand is heteropolymeric with a G-C content between 25% and 75%;

each strand is heteropolymeric with a G-C content between 10% and 90%, and furthermore the combined frequencies therein of purine-pyrimidine dimers and pyrimidine-purine dimers exceeds 25%;

it is not in a cell (and not in a virus);

each said strand independently comprises a heteropolymeric nucleic acid or a heteropolymeric nucleic acid analogue;

each said strand independently comprises DNA or RNA;

each said strand independently comprises a heteropolymeric nucleic acid analogue containing an uncharged or partially charged backbone;

one of said second strand or said fourth strand comprises DNA and the other of said second strand or said fourth strand comprises RNA, mRNA, hnRNA, rRNA, tRNA or cDNA;

the second strand and said fourth strand are parallel homologous to each other;

a major groove of said first strand and said second strand is placed in a minor groove of said third strand and said fourth strand;

the second strand and said fourth strand are parallel complementary to each other;

a major groove of said first strand and said second strand is placed in a minor groove of said third strand and said fourth strand;

each nucleobase binds to no more than two other nucleobases;

no strand is contiguous with another strand;

the multiplex structure is substantially free of Hoogsteen bonding;

the multiplex structure is substantially free of G-G quartets;

the first strand and said second strand are 5 to 50 base pairs long;

the third strand and said fourth strand are genomic DNA;

the third strand and said fourth strand include a haplotype in genomic DNA;

the third strand and fourth strand are PCR amplified products;

wherein said multiplex structure is free of solid support;

the multiplex structure is bound to a solid support (where the solid support is either electrically conductive or is not electrically conductive);

wherein the multiplex structure further comprises a therapeutic, prophylactic or diagnostic agent bound to at least one of said first strand, said second strand, said third strand and said fourth strand;

wherein the first strand and said second strand are each 5 to 30 bases long and said third strand and said fourth strand are each 8 to $3.3 \times 10^9$ base pairs long;

wherein the fourth sequence contains 25% to 75% purine bases and 75% to 25% pyrimidine bases in any order (preferably wherein the frequency of purine-pyrimidine dimers plus the frequency of pyrimidine-purine dimers exceeds 25%);

the first and second Watson-Crick duplexes (see the method of making a quadruplex in the Summary of the Invention section) each have a G-C content between 30 and 70%;

both strands of the first Watson-Crick duplex are DNA (especially where all strands of the quadruplex are DNA);

the accelerator reagent binds to a base in the first Watson-Crick duplex, said base being one to which a base in the second duplex binds;

the accelerator reagent binds to a base in the first or second Watson-Crick duplexes, said base not being part of the quadruplex;

the accelerator reagent binds to a phosphate backbone of the first or second Watson-Crick duplex;

the accelerator reagent binds to more than one site on one of the first or second Watson-Crick duplexes, each site either on a base or on a phosphate backbone;

the accelerator agent binds to one site on the Watson-Crick duplex, said site either on a base or on a phosphate backbone;

the accelerator agent binds to a base in the first Watson-Crick duplex and to a base on the second Watson-Crick duplex;

the accelerator agent binds to the minor groove of the first and/or second Watson-Crick duplex;

the accelerator agent forms a bond between part of the first Watson-Crick duplex and part of the second Watson-Crick duplex.

Additional Aspects of the Invention

The invention provides triplex complexes comprising a single-stranded probe bound to a double-stranded nucleic acid target, wherein the probe comprises a heteropolymeric nucleic acid or a heteropolymeric nucleic acid analog, and all base triplets of the complex are members selected from the group consisting of A-T-A, T-A-T, U-A-T, T-A-U, A-U-A, U-A-U, G-C-G and C-G-C.

Unlike certain Hoogsteen triplexes disclosed by the prior art, the triplexes of the invention are stable at pH values greater than 7.6. Moreover, the inventive triplexes do not require the presence of homopyrimidine sequences or homopurine sequences, as in certain prior art triplexes. For example, the target sequence can contain 25% to 75% purine bases and 75% to 25% pyrimidine bases in any order.

Preferably the single-stranded nucleic acid or nucleic acid analog of the triplex is 5 to 30 bases long and the double-stranded nucleic acid target is 8 to $3.3 \times 10^9$ base pairs long.

Triplex formation according to the invention is suitable for a variety of uses. For example, probes covalently bound to a double-stranded nucleic acid cleaving agent can be used to specifically cleave target sequences of double-stranded nucleic acids. Probes covalently bound to a chemotherapeutic agent can be used to specifically treat target sequences of double-stranded nucleic acids.

In preferred embodiments, the invention provides a rapid, sensitive, environmentally friendly, and safe method for assaying binding between a double-stranded target and a single-stranded probe, wherein the target comprises a nucleic acid sequence or a nucleic acid analog sequence and the probe comprises a nucleic acid sequence or a nucleic acid analog sequence.

Unlike certain prior art assays, the invention not only detects the presence of specific probe-target binding, but also provides qualitative and quantitative information regarding the nature of interaction between a probe and target. Thus, the invention enables the practitioner to distinguish among a perfect match, a one base pair mismatch, a two base pair mismatch, a three base pair mismatch, a one base pair deletion, a two base pair deletion and a three base pair deletion arising between a base sequence in the probe and in a strand of the double-stranded target.

Embodiments of the invention comprise calibrating the measured signal (e.g., fluorescent intensity) for a first probe-target mixture against the same type of signal exhibited by other probes combined with the same target, wherein each of the other probes differs from the first probe by at least one base.

A calibration curve can be generated, wherein the magnitude of the measured signal (e.g., fluorescent intensity) is a function of the binding affinity between the target and probe. As the binding affinity between the target and a plurality of different probes varies with the number of mismatched bases, the nature of the mismatch(es) (A-G vs. A-C vs. T-G vs. T-C, etc.), the location of the mismatch(es) within the triplex, etc., the assay of the invention can be used to sequence the target.

In embodiments, the signal measured can be the fluorescent intensity of a fluorophore included in the test sample. In such embodiments, the binding affinity between the probe and target can be directly or inversely correlated with the intensity, depending on whether the fluorophore signals hybridization through signal quenching or signal amplification. Under selected conditions, the fluorescent intensity generated by intercalating agents can be directly correlated with probe-target binding affinity, whereas the intensity of preferred embodiments employing a non-intercalating fluorophore covalently bound to the probe can be inversely correlated with probe-target binding affinity. The fluorescent intensity decreases for non-intercalating fluorophores as the extent of matching between the probe and target increases, preferably over a range inclusive of 0–2 mismatches and/or deletions, more preferably over a range inclusive of 0–3 mismatches and/or deletions.

The invention enables quantifying the binding affinity between probe and target. Such information can be valuable for a variety of uses, including designing antisense drugs with optimized binding characteristics.

Unlike prior art methods, the assay of the invention is preferably homogeneous. The assay can be conducted without separating the probe-target complex from the free probe and target prior to detecting the magnitude of the measured signal. The assay does not require a gel separation step, thereby allowing a great increase in testing throughput. Quantitative analyses are simple and accurate. Consequently the binding assay saves a lot of time and expense, and can be easily automated.

Furthermore, it enables binding variables such as buffer, pH, ionic concentration, temperature, incubation time, relative concentrations of probe and target sequences, intercalator concentration, length of target sequences, length of probe sequences, and possible cofactor requirements to be rapidly determined.

The assay can be conducted in, e.g., a solution within a well, on an impermeable surface or on a biochip.

Moreover, the inventive assay is preferably conducted without providing a signal quenching agent on the target or on the probe.

Although the inventors have previously disclosed the advantages of fluorescent intensity assays for hybridization (see, e.g., U.S. patent application Ser. No. 09/224,505, filed Dec. 31, 1998), assays according to the present invention specifically detect triplexes of the probe and the double-stranded target, thus obviating the need to denature the target. While nucleic acid (and nucleic acid analog) probes have been known to form triplexes with certain limited classes of targets (see, e.g., Floris et al., supra, Dervan et al., supra, Egholm et al., 365 Nature 566 (1993), and Tomac et al., 118 J. Am. Chem. Soc. 5544 (1996)), it is surprising that the inventors have been able to specifically assay triplexes formed between single-stranded nucleic acid (e.g., ssDNA and RNA) probes and double-stranded nucleic acid (e.g., dsDNA) targets, wherein the interaction between the probes and targets is based on Watson-Crick base pairing (at least in the sense that A binds to T (or U, in the case of RNA) and G binds to C), rather than the very limited Hoogsteen model of triplex hybridization of, e.g., Dervan et al. The term "Watson-Crick triplex," which is employed herein, is intended to crystallize these differences by limiting the nature of base pairing between the single-stranded probe and the double-stranded target to A-T-A, T-A-T, U-A-T, T-A-U, A-U-A, U-A-U, G-C-G and/or C-G-C (including $C^+$-G-C, and/or any other ionized species of base). These three-member groups are hereinafter denoted Watson-Crick base triplets and the resulting structures denoted Watson-Crick triplexes.

Suitable probes for use in the inventive assay include, e.g., ssDNA, RNA, PNA and other nucleic acid analogs having uncharged or partially-charged backbones. Probe sequences having any length from 8 to 20 bases are preferred since this is the range within which the smallest unique DNA sequences of prokaryotes and eukaryotes are found. Probes of 12 to 18 bases are particularly preferred since this is the length of the smallest unique sequences in the human genome. In embodiments, probes of 5 to 30 bases are most preferred. However, a plurality of shorter probes can be used to detect a nucleotide sequence having a plurality of non-unique target sequences therein, which combine to uniquely identify the nucleotide sequence. The length of the probe can be selected to match the length of the target.

The inventors have discovered the surprising development that they were able to specifically assay a wide-variety of triplexes formed in a Watson-Crick base-pair dependent manner between single-stranded nucleic acid (e.g., ssDNA, RNA, ssPNA and other analogs of DNA or RNA) probes and double-stranded nucleic acid (e.g., dsDNA) targets. The inventors have discovered that triplex formation and/or stabilization is enhanced by the presence of an intercalating agent in the sample being tested.

The inventors have discovered that Watson-Crick triplex formation and/or stabilization is enhanced by the presence of cations in the sample being tested. Suitable cations include, e.g., monovalent cations, such as $Na^+$ (preferably at a concentration of 5 mM to 125 mM), $K^+$, and other alkali metal ions; divalent cations, such as alkaline earth metal ions (e.g., $Mg^{+2}$ and $Ca^{+2}$) and divalent transition metal ions (e.g., $Mn^{+2}$, $Ni^{+2}$, $Cd^{+2}$, $Co^{+2}$ and $Zn^{+2}$); and cations having a positive charge of at least three, such as $Co(NH_3)_6^{+3}$, trivalent spermidine and tetravalent spermine. $Mn^{+2}$ is preferably provided at a concentration of 10 mM to 30 mM. $Mg^{+2}$ is preferably provided at a concentration of 15 mM to 20 mM. $Ni^{+2}$ is preferably provided at a concentration of about 20 mM. In embodiments, $Mg^{+2}$ and $Mn^{+2}$ are provided in combination at a concentration of 10 mM each, 15 mM each or 20 mM each (i.e., 10–20 mM each).

The amount of cation added to the medium in which the triplex forms depends on a number of factors, including the nature of the cation, the concentration of probe, the concentration of target, the presence of additional cations and the base content of the probe and target. The preferred cation concentrations and mixtures can routinely be discovered experimentally.

The instant invention does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

In embodiments, the probe is labeled with a multi-molecule signaling complex or a redox pair, or with a label that elicits chemiluminescent or electrochemiluminescent properties.

It is preferred that the probe or target (preferably the probe) have a fluorescent label covalently bound thereto. The label is preferably a non-intercalating fluorophore. In such embodiments, the fluorophore is preferably bound to the probe at either end. Preferred fluorescent markers include biotin, rhodamine and fluorescein, and other markers that fluoresce when irradiated with exciting energy.

The excitation wavelength is selected (by routine experimentation and/or conventional knowledge) to correspond to this excitation maximum for the fluorophore being used, and is preferably 200 to 1000 nm. Fluorophores are preferably selected to have an emission wavelength of 200 to 1000 nm. In preferred embodiments, an argon ion laser is used to irradiate the fluorophore with light having a wavelength in a range of 400 to 540 nm, and fluorescent emission is detected in a range of 500 to 750 nm.

The assay of the invention can be performed over a wide variety of temperatures, such as, e.g., from 5 to 85° C. Certain prior art assays require elevated temperatures, adding cost and delay to the assay. On the other hand, the invention can be conducted at room temperature or below (e.g., at a temperature below 25° C.).

The reliability of the invention is independent of guanine and cytosine content in said target. Since G-C base pairs form three hydrogen bonds, while A-T base pairs form only two hydrogen bonds, target and probe sequences with a higher G or C content are more stable, possessing higher melting temperatures. Consequently, base pair mismatches that increase the GC content of the hybridized probe and target region above that present in perfectly matched hybrids may offset the binding weakness associated with a mismatched probe. Triplexes containing every possible base pair mismatch between the probe and the target proved to be more unstable than perfectly matched triplexes, always resulting in lower fluorescent intensities than did perfectly complementary hybrids, when an intercalating fluorophore was used.

The inventive assay is extremely sensitive, thereby obviating the need to conduct PCR amplification of the target. For example, it is possible to assay a test sample having a volume of about 20 microliters, which contains about 10 femtomoles of target and about 10 femtomoles of probe. Embodiments of the invention are sensitive enough to assay targets at a concentration of $5 \times 10^{-9}$ M, preferably at a concentration of not more than $5 \times 10^{-10}$ M. Embodiments of the invention are sensitive enough to employ probes at a concentration of $5 \times 10^{-9}$ M, preferably at a concentration of not more than $5 \times 10^{-10}$ M. It should go without saying that the foregoing values are not intended to suggest that the method cannot detect higher concentrations.

The medium in which triplexes form can be any conventional medium known to be suitable for preserving nucleotides. See, e.g., Sambrook et al., "Molecular Cloning: A Lab Manual," Vol. 2 (1989). For example, the liquid medium can comprise nucleotides, water, buffers and standard salt concentrations. When divalent cations are used exclusively to promote triplex formation, chelators such as EDTA or EGTA should not be included in the reaction mixtures.

Specific binding between complementary bases occurs under a wide variety of conditions having variations in temperature, salt concentration, electrostatic strength, and buffer composition. Examples of these conditions and methods for applying them are known in the art.

Unlike many Hoogsteen-type triplexes, which are unstable or non-existent at pH levels above about 7.6, the Watson-Crick triplexes of the invention are stable over a wide range of pH levels, preferably from about pH 5 to about pH 9.

It is preferred that triplexes be formed at a temperature of about 5° C. to about 25° C. for about one hour or less. Longer reaction times are not required, but incubation for up to 24 hours in most cases did not adversely affect the triplexes. The fast binding times of Watson-Crick triplexes of the invention contrast with the much longer binding times for Hoogsteen triplex-based assays.

Although not required, it is possible to facilitate triplex formation in solution by using certain reagents in addition to cations. Preferred examples of these reagents include single stranded binding proteins such as Rec A protein, T4 gene 32 protein, *E. coli* single stranded binding protein, major or minor nucleic acid groove binding proteins, viologen and intercalating substances such as ethidium bromide, actinomycin D, psoralen, and angelicin. Such facilitating reagents may prove useful in extreme operating conditions, for example, under abnormal pH levels or extremely high temperatures.

The inventive assay can be used to, e.g., identify accessible regions in folded nucleotide sequences, to determine the number of mismatched base pairs in a hybridization complex, and to map genomes.

The inventors may sometimes herein suggest that Watson-Crick triplexes result from hybridization of the probe to duplex target. While fluorophores tethered to the probe produced quenched fluorescent emissions upon being exposed to duplex targets containing a strand of Watson-Crick complementary bases, which indicates the occurrence of some kind of binding event, the inventors are not sure that what occurs in the Watson-Crick triplex is best described as hybridization in the sense traditionally associated with Watson-Crick duplex formation. While the formation of a Watson-Crick triplex may sometimes be referred to as a hybridization event herein, that is merely for convenience and is not intended to limit the scope of the invention with respect to how the formation of a Watson-Crick triplex can be best characterized.

Unlike the quadruplexes discussed in the Background Section above, the preferred multiplex structures of the invention contain at least four strands of nucleic acid bonded together according to traditional Watson-Crick bonding rules.

As used herein, the term "Watson-Crick bonding" is intended to define specific association between opposing pairs of nucleic acid (and/or nucleic acid analogue) strands via matched, opposing bases. While the formation of a Watson-Crick quadruplex may sometimes be referred to as a hybridization event herein, that is merely for convenience and is not intended to limit the scope of the invention with respect to how the formation of a Watson-Crick quadruplex can be best characterized.

The multiplex structures of the invention are preferably quadruplexes. Each strand of the multiplex independently comprises a nucleic acid or a nucleic acid analogue. Suitable nucleic acids include, e.g., DNA or RNA. Preferred nucleic acid analogues contain an uncharged or partially charged backbone (i.e., a backbone having a charge that is not as negative as a native DNA backbone).

In certain embodiments, one of the second and fourth strands of the four-stranded quadruplex comprises DNA and the other of the second and fourth strands comprises RNA, mRNA, hnRNA, rRNA, tRNA or cDNA.

In certain embodiments, the second strand and the fourth strand are parallel homologous to each other. In these embodiments, a major groove of the first and second strands is placed in a minor groove of the third and fourth strands.

In other embodiments, the second and fourth strands are parallel complementary to each other. In these embodiments, which possess "nested complementarity," a major groove of the first and second strands is placed in a minor groove of the third and fourth strands.

In certain embodiments, each nucleobase binds to no more than two other nucleobases. In some of these embodiments, the bases of the second strand specifically bond (via Watson-Crick rules) to the matching bases of the first strand and to the matching bases of the fourth strand, and the bases of the fourth strand specifically bond (via Watson-Crick rules) to the matching bases of the third strand and to the matching bases of the second strand, wherein the bases of the first and third strands bind to no more than one other base each. Thus, in addition to the traditional Watson-Crick base pairs, such embodiments include the following Watson-Crick base triplets: A-T-A, T-A-T, U-A-T, T-A-U, A-U-A, U-A-U, G-C-G and/or C-G-C (including $C^+$-G-C, and/or any other ionized species of base).

In certain embodiments, it is believed that opposing bases of the first and third strands also bind to each other, in addition to: (a) the binding between opposing bases of the first and second strands; (b) the binding between opposing bases of the third and fourth strands; and (c) the binding between opposing bases of the second and fourth strands.

In certain embodiments of the multiplex structure of the invention, no strand is contiguous with another strand. That is, there are at least four separate strands. Although folded conformations and the like (e.g., hairpin turns, etc.) are within the scope of the invention, folded portions of a single strand do not make the strand count more than once toward the minimum of four separate strands.

Multiplex structures of the invention preferably do not rely on Hoogsteen bonding or G-G quartets for maintenance of the multiplex structure, although insignificant amounts of Hoogsteen bonding and/or G-G quartets may be present. That is, multiplex structures of the invention are preferably substantially free of Hoogsteen bonding, and substantially free of G-G quartets.

In certain embodiments, the first and second strands of the multiplex are 5 to 50 bases long (more preferably 5 to 30 bases long) and the third and fourth strands are 8 to $3.3 \times 10^9$ base pairs long. For example, the first and second strands can constitute a double-stranded probe and the third and fourth strands can constitute a double-stranded target, such as genomic DNA, which can contain a haplotype.

In embodiments, the third strand and the fourth strand are PCR amplified products.

The multiplexes of the invention can be present in solution, on a solid support, in vitro or in vivo. The solid support can be electrically conductive (e.g., an electrode) or non-conductive.

Quadruplex formation according to the invention is suitable for a variety of uses. For example, double-stranded probes covalently bound to a double-stranded nucleic acid cleaving agent can be used to specifically cleave target sequences of double-stranded nucleic acids. Double-stranded probes covalently bound to a chemotherapeutic agent can be used to specifically treat target sequences of double-stranded nucleic acids. Thus, the invention encompasses multiplex structures further comprising a therapeutic, prophylactic or diagnostic agent bound to at least one of the first, second, third and fourth strands.

In addition, multiplexes of the invention are suitable for use in nanoengineering, such as to provide electrical circuitry on a molecular (i.e., nanoscale) level. Further details regarding nanoengineering with nucleic acids can be found in U.S. Pat. No. 5,948,897 to Sen et al. and the references cited therein.

Multiplex structures of the invention can be provided by a method comprising: providing a hybridization medium comprising the first strand, the second strand, the third strand, the fourth strand, water, a buffer and a promoter; and incubating the hybridization medium for an incubation time effective to hybridize the second strand to the fourth strand.

The hybridization medium can include any conventional medium known to be suitable for preserving nucleotides. See, e.g., Sambrook et al., "Molecular Cloning: A Lab Manual," Vol. 2 (1989). For example, the medium can comprise nucleotides, water, buffers and standard salt concentrations. When divalent cations are used exclusively to promote quadruplex formation, chelators such as EDTA or EGTA should not be included in the reaction mixtures.

Specific binding between complementary bases occurs under a wide variety of conditions having variations in temperature, salt concentration, electrostatic strength, and buffer composition. Examples of these conditions and methods for applying them are known in the art.

Unlike many Hoogsteen-type multiplexes, which are unstable or non-existent at pH levels above about 7.6, the Watson-Crick multiplexes of the invention are stable over a wide range of pH levels, preferably from about pH 5 to about pH 9.

Moreover, the inventive multiplexes do not require the presence of homopyrimidine sequences or homopurine sequences, as in certain prior art quadruplexes. For example, the target sequence can contain 25% to 75% purine bases and 75% to 25% pyrimidine bases in any order.

It is preferred that multiplexes be formed at a temperature of about 5° C. to about 25° C. for about two hours or less. The incubation time is preferably less than five minutes, even at room temperature. Longer reaction times are not required, but incubation for up to 24 hours in most cases did not adversely affect the quadruplexes. The fast binding times of Watson-Crick quadruplexes of the invention contrast with the much longer binding times for Hoogsteen quadruplexes.

The promoter in the hybridization medium is preferably an intercalating agent or a cation. The intercalating agent can be, e.g., a fluorophore, such as a member selected from the group consisting of YOYO-1, TOTO-1, ethidium bromide, ethidium homodimer-1, ethidium homodimer-2 and acridine.

Suitable cations include, e.g., monovalent cations, such as $Na^+$ (preferably at a concentration of 50 mM to 125 mM), $K^+$, and other alkali metal ions; divalent cations, such as alkaline earth metal ions (e.g., $Mg^{+2}$ and $Ca^{+2}$) and divalent transition metal ions (e.g., $Mn^{+2}$, $Ni^{+2}$, $Cd^{+2}$, $Co^{+2}$ and $Zn^{-2}$); and cations having a positive charge of at least three, such as $Co(NH_3)_6^{+3}$, trivalent spermidine and tetravalent spermine. $Mn^{-2}$ is preferably provided at a concentration of 10 mM to 45 mM. $Mg^{+2}$ is preferably provided at a concentration of 10 mM to 45 mM. $Ni^{+2}$ is preferably provided at a concentration of about 20 mM. In embodiments, $Mg^{+2}$ and $Mn^{+2}$ are provided in combination at a concentration of 10 mM each, 15 mM each, 20 mM each, 25 mM each, 30 mM each, 35 mM each, or 40 mM each (i.e., 10–40 mM each).

The amount of cation added to the medium in which the multiplex forms depends on a number of factors, including the nature of the cation, the concentration of probe, the concentration of target, the presence of additional cations and the base content of the probe and target. The preferred cation concentrations and mixtures can routinely be discovered experimentally.

Although not required, other promoters include, e.g., single stranded binding proteins such as Rec A protein, T4 gene 32 protein, E. coli single stranded binding protein, major or minor nucleic acid groove binding proteins, viologen and additional intercalating substances such as actinomycin D, psoralen, and angelicin. Such facilitating reagents may prove useful in extreme operating conditions, for example, under abnormal pH levels or extremely high temperatures.

The invention also enables a method in which hybridization of the second strand to the fourth strand inactivates an activity associated with at least one of the third strand and the fourth strand. Thus, at least one of the first strand and the second strand further comprises a pharmaceutical agent, wherein hybridization of the second strand to the fourth strand places the pharmaceutical agent an effective distance from a target on the third strand, the fourth strand or on another molecule associated with at least one of the third strand and the fourth strand. The pharmaceutical agent is preferably a member selected from the group consisting of nucleic acids designed to bind promoter sequences of clinically relevant genes, nucleic acids designed to bind clinically relevant genes, or nucleic acids designed to bind origin of replication sites of pathogens.

In preferred embodiments, the invention provides a rapid, sensitive, environmentally friendly, and safe method for assaying binding between a single-stranded or double-stranded target and a double-stranded probe, wherein the target comprises a nucleic acid sequence or a nucleic acid analogue sequence and the probe comprises a nucleic acid sequence or a nucleic acid analogue sequence.

The inventive assay can be used to, e.g., identify accessible regions in folded nucleotide sequences, to determine the number of mismatched base pairs in a hybridization complex, and to map genomes.

The invention not only detects the presence of specific probe-target binding, but also provides qualitative and quantitative information regarding the nature of interaction between a probe and target. Thus, the invention enables the practitioner to distinguish among a perfect match, a one base pair mismatch, a two base pair mismatch, a three base pair mismatch, a one base pair deletion, a two base pair deletion and a three base pair deletion arising between a sequence in the double-stranded probe and in a sequence in the double-stranded target.

Embodiments of the invention comprise calibrating the measured signal (e.g., fluorescence, chemiluminescence, electrochemiluminescence or electrical properties) for a first probe-target mixture against the same type of signal exhibited by other probes combined with the same target, wherein each of the other probes differs from the first probe by at least one base.

A calibration curve can be generated, wherein the magnitude of the measured signal (e.g., fluorescent intensity) is a function of the binding affinity between the target and probe. As the binding affinity between the target and a plurality of different probes varies with the number of mismatched bases, the nature of the mismatch(es) (A-G vs. A-C vs. T-G vs. T-C, etc.), the location of the mismatch(es) within the quadruplex, etc., the assay of the invention can be used to sequence the target.

In embodiments, the signal measured can be the fluorescent emission intensity of a fluorophore included in the test sample. In such embodiments, the binding affinity between the probe and target can be directly or inversely correlated with the emission intensity, depending on whether the fluorophore signals hybridization through signal quenching or signal amplification. Under selected conditions, the fluorescent emission intensity generated by intercalating agents can be directly correlated with probe-target binding affinity, whereas the emission intensity of preferred embodiments employing a non-intercalating fluorophore covalently bound to the probe can be inversely correlated with probe-target binding affinity. The fluorescent emission intensity decreases for non-intercalating fluorophores as the extent of matching between the probe and target increases, preferably over a range inclusive of 0–2 mismatches and/or deletions, more preferably over a range inclusive of 0–3 mismatches and/or deletions.

The invention enables quantifying the binding affinity between probe and target. Such information can be valuable for a variety of uses, including designing antisense drugs with optimized binding characteristics.

The assay of the invention is preferably homogeneous. The assay can be conducted without separating the probe-target complex from the free probe and free target prior to detecting the magnitude of the measured signal. The assay does not require a gel separation step, thereby allowing a great increase in testing throughput. Quantitative analyses are simple and accurate. Consequently the binding assay saves a lot of time and expense, and can be easily automated. Furthermore, it enables binding variables such as buffer, pH, ionic concentration, temperature, incubation time, relative concentrations of probe and target sequences, intercalator concentration, length of target sequences, length of probe sequences, and possible cofactor (i.e., promoter) requirements to be rapidly determined.

The assay can be conducted in, e.g., a solution within a well or microchannel, on an impermeable surface or on a biochip. In certain embodiments, the third and fourth strands are provided in the hybridization medium before the first and second strands, and the first and second strands are provided in dehydrated form prior to rehydration by contact with the hybridization medium.

Moreover, the inventive assay is preferably conducted without providing a signal quenching agent on the target or on the probe.

Although the inventors have previously disclosed the advantages of fluorescent intensity assays for hybridization (see, e.g., U.S. patent application Ser. No. 09/224,505, filed Dec. 31, 1998), certain embodiments of the inventive assay specifically detect quadruplexes of the probe and the double-stranded target, thus obviating the need to denature the target. It is surprising that the inventors have been able to specifically assay quadruplexes formed between double-stranded probes and double-stranded targets, wherein the interaction between the probes and targets is based on Watson-Crick base pairing (at least in the sense that A binds to T (or U, in the case of RNA) and G binds to C), rather than the very limited Hoogsteen model of quadruplex hybridization of, e.g., Pitner et al., supra.

Suitable probes for use in the inventive assay include, e.g., dsDNA, dsRNA, DNA:RNA hybrids, dsPNA, PNA:DNA hybrids and other double-stranded nucleic acid analogues having uncharged or partially-charged backbones. Probe sequences having any length from 8 to 20 bases are preferred since this is the range within which the smallest unique DNA sequences of prokaryotes and eukaryotes are found. Probes of 12 to 18 bases are particularly preferred since this is the length of the smallest unique sequences in the human genome. In embodiments, probes of 5 to 30 bases are most preferred. However, a plurality of shorter probes can be used to detect a nucleotide sequence having a plurality of non-unique target sequences therein, which combine to uniquely identify the nucleotide sequence. The length of the probe can be selected to match the length of the target.

The instant invention does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

In embodiments, the probe is labeled with a multi-molecule signaling complex or a redox pair, or with a label that elicits chemiluminescent or electrochemiluminescent properties.

When a fluorescent intercalator is not present in the hybridization medium, it is preferred that the probe or target (preferably the probe) have a fluorescent label covalently bound thereto. The label is preferably a non-intercalating fluorophore or an intercalating fluorophore. In such embodiments, the fluorophore is preferably bound to the probe at either end. Preferred fluorescent markers include biotin, rhodamine, acridine and fluorescein, and other markers that fluoresce when irradiated with exciting energy.

The excitation wavelength is selected (by routine experimentation and/or conventional knowledge) to correspond to this excitation maximum for the fluorophore being used, and is preferably 200 to 1000 nm. Fluorophores are preferably selected to have an emission wavelength of 200 to 1000 nm. In preferred embodiments, an argon ion laser is used to irradiate the fluorophore with light having a wavelength in a range of 400 to 540 nm, and fluorescent emission is detected in a range of 500 to 750 nm.

The assay of the invention can be performed over a wide variety of temperatures, such as, e.g., from 5 to 85° C.

Certain prior art assays require elevated temperatures, adding cost and delay to the assay. On the other hand, the invention can be conducted at room temperature or below (e.g., at a temperature below 25° C.).

The reliability of the invention is independent of guanine and cytosine content in said target. Since G-C base pairs form three hydrogen bonds, while A-T base pairs form only two hydrogen bonds, target and probe sequences with a higher G or C content are more stable, possessing higher melting temperatures. Consequently, base pair mismatches that increase the GC content of the hybridized probe and target region above that present in perfectly matched hybrids may offset the binding weakness associated with a mismatched probe.

The inventive assay is extremely sensitive, thereby obviating the need to conduct PCR amplification of the target. For example, it is possible to assay a test sample having a volume of about 20 microliters, which contains about 10 femtomoles of target and about 10 femtomoles of probe. Embodiments of the invention are sensitive enough to assay targets at a concentration of $5\times10^{-9}$ M, preferably at a concentration of not more than $5\times10^{-10}$ M. Embodiments of the invention are sensitive enough to employ probes at a concentration of $5\times10^{-9}$ M, preferably at a concentration of not more than $5\times10^{-10}$ M. It should go without saying that the foregoing values are not intended to suggest that the method cannot detect higher concentrations.

The ratio of probe (e.g., first and second strands) to target (e.g., third and fourth strands) is 30:1 to 1:1, preferably about 10:1.

The Examples will show that YOYO-1, a known minor groove inhabiting intercalator of duplex DNA, can facilitate and signal triplex association or binding of a DNA oligo with a duplex target, which is indicative of the degree of complementarity, ascertained on the basis of Watson-Crick base pair recognition between the bases on the oligo and the bases of the complementary sequence in the duplex target.

The triplex binding observed can not be a version of the homopyrimidine triplex motif, well characterized in the literature, due to that complexes' requirement for high acid conditions. Similarly, if our typical wild type 33% GC content 15-mer oligo was evaluated as a binding partner to the "purine rich strand" in the duplex target, as is the requirement for the homopurine triplex motif, our oligo would be mismatched by 9 bases in either the oligo sequence or the putative binding site on the purine rich strand of the target duplex.

The YOYO-1 intercalator has been reported by Johansen and Jacobsen (1998) as inhabiting the minor groove of duplex DNA based upon NMR spectroscopic studies. It is also reported that YOYO-1 acted to locally decondense the B conformation of the duplex DNA by 106° resulting in an overall helical repeat of 13 base pairs rather than the 10 base pairs usually found in a B conformation helical repeat.

As a fluorophore, YOYO-1's emission was greatly enhanced by the addition of complementary oligo to the medium bearing the duplex target. The enhanced emission associated with the interaction of the oligo and the duplex can be credited either to the YOYO-1 being present in the duplex minor groove and emitting light more energetically upon the contacting of the oligo with the duplex or to the YOYO-1 finding a second hospitable place to locate itself in the groove created by the oligo and the complementary strand in the duplex when the respective bases thereof contact one another. It is also possible that both events are occurring. Further studies, such as X-ray crystallography and NMR spectroscopy will establish the possible locations and interactions of YOYO-1 with the Natural Triplex.

Johansen and Jacobsen (1998) concluded that the decondensation of the duplex DNA by 106° is caused by the bis-intercalation of the YOYO-1 chromophore while the polypropylene amine linker chain remains in the minor groove of the duplex. This may be part of the mechanism whereby the target is decondensed 106°, a relaxation which will be expressed out from the site of the YOYO-1 interaction in both directions. It may also be possible that the +4 cationic nature of YOYO-1 located in the minor groove between the backbone of the duplex results in relaxation of the repulsion between the phosphate anionic charges in the immediate vicinity of the YOYO-1 binding site, causing the backbone strands to move closer to one another in the vicinity of the YOYO-1. Should a second YOYO-1 locate itself near a YOYO-1 present in the duplex minor groove, by inhabiting the groove created by the oligo and the complementary strand when contacting one another in the minor groove, that YOYO-1 would also act in reducing the anionic repulsion between the oligo backbone and the complementary sequence's region of the backbone.

We also observed that reagents which condense duplex DNA have the ability to facilitate triplex formation. In addition to the well known ability of monovalent, divalent, and multivalent cations to condense duplex DNA, our results suggest that cations form bridges which make possible binding between bases in the oligo and bases in the complementary strand of the duplex. We showed this by first forming triplexes facilitated by cations and then destroying the bridging structures. The result of continued lasing of the medium in which the cations and triplex were present was the rapid disappearance of all triplex structures.

Our experience with triplexes facilitated by YOYO-1 is that they are readily formed at room temperature and persist for many hours when formed. Over time, mismatched oligos continue the same lower level of fluorophore emission indicating the same level of triplex formation. Cations on the other hand appear to result in transitory conditions which are conducive to triplex or quadruplex formations. The cations included intercalators such as YOYO-1, metal center cations such as $MgCl_2$, or cationic peptides such as spermidine, all of which act on the conformation by interacting with anionic charges to result in the modification of the conformation of the duplex DNA target. The results varied with cation species, concentration or the presence of several species at varying concentrations.

We have shown that appropriate concentrations of organic solvents allow modification of the target duplex DNA, which allows triplexes to occur.

The transitory nature of much of triplex and quadruplex formation is congruent with the organism's requirement that many processes involving the accessing of sequence information from duplex DNA be easily reversible, that is activated and terminated. Nevertheless, such formations are sufficiently stable so that diagnostic and other assays can be based upon them.

We have therefore discovered that it is condensation or decondensation of the duplex DNA by whatever means which makes possible recognition between the oligo and the complementary sequence sufficient to achieve a contacting of at least one base on the oligo with a base in the complementary strand of the duplex target. There are probably a number of departures from the position usually enjoyed by adjacent base pairs in a sequence when the size of the helical repeat is modified by condensation or decondensation. This realignment of stacked base pairs in the modified helix most likely allows for a sufficient change in electron orbits from that present within the base stack of an unmodified double helix, to allow binding of the third strand to the complementary strand to commence.

Duplex modification by either condensation or decondensation may occur in a rather homogeneous fashion with all anionic charges in the dsDNA and vicinity affected at generally the same time or the modification may be localized. In the latter case, a series of greatly varying modifications will occur in the DNA base pairs and backbones progressively distant from the locus of modification. In either case conditions can be created to allow a binding event between a base on the oligo and a base in the complementary strand of the duplex to generate triplex pairing. Once such a binding has been initiated it can be understood how the two flanking sequences of bases on the oligo might be swung into position to bind to bases in the flanking sequences of the complementary strand of the duplex.

While our experiments show great stability in the triplexes facilitated by YOYO-1, many other reagents have effects on the conformation of the duplex DNA which result in Natural Triplexes being formed transiently. These triple helix structures continue to progress into conformations which are less favorable to triplex maintenance, resulting in loss of the triplex structure.

Any agent capable of acting to modify the conformation of target dsDNA must be monitored as to its effects over time to establish concentrations and incubation times suitable in the conditions of temperature, pH, etc. selected. This application teaches many methods of evaluating such reagents which can be used or modified by those skilled in the art so as to practice what is herein taught.

The invention will be illustrated in more detail with reference to the Examples that follow, but it should be understood that the present invention is not deemed to be limited thereto.

EXAMPLES

The invention will be illustrated in more detail with reference to the following Examples, but it should be understood that the present invention is not deemed to be limited thereto.

Example 1

Example 1 demonstrates that the assay of the invention can discriminate between perfectly complementary dsDNA:ssDNA complexes and dsDNA:ssDNA complexes containing 1 bp, 2 bp and 3 bp mismatches or deletions when a cationic DNA intercalator, YOYO-1 (Molecular Probes, Eugene, Oreg., USA), is present. NMR spectroscopic analyses of the mechanism of interaction between YOYO-1 and dsDNA have shown that the intercalation of YOYO-1 results in a localized decondensation of the dsDNA helix by 106° generating an overall helical repeat of 13 base pairs as opposed to the normal 10 base pair helical repeat in non-condensed B conformation dsDNA [J. Biomolec. Struct. and Dynamics 16, 205–222 (1998)].

Complementary sense and antisense 50-mer ssDNA target sequences, derived from exon 10 of the human cystic fibrosis gene [Nature 380, 207 (1996)] were synthesized on a DNA synthesizer (Expedite 8909, PerSeptive Biosystems) and purified by HPLC. Equimolar amounts of the complementary oligonucleotides were heated at 95° C. for 10 min and allowed to anneal gradually as the temperature cooled to 21° C. over 1.5 hours. DsDNA oligonucleotides were dissolved in ddH$_2$O at a concentration of 1 pmole/µl.

Sequence for the sense strand of the wild-type target DNA (SEQ ID NO:1) was:

5'-TGG CAC CAT TAA AGA AAA TAT CAT CTT TGG TGT TTC CTA TGA TGA ATA TA-3'

Sequence for the antisense strand of the wild-type target DNA (SEQ ID NO:1) was:

5'-TAT ATT CAT CAT AGG AAA CAC CAA AGA TGA TAT TTT CTT TAA TGG TGC CA-3'

SEQ ID NO:2 was a 50-mer mutant dsDNA target sequence identical to wild-type target DNA (SEQ ID NO:1) except for a one base pair mutation (underlined) at amino acid position 507 at which the wild-type sense strand sequence CAT was changed to CGT.

Sequence for the sense strand of SEQ ID NO:2 was:

5'-TGG CAC CAT TAA AGA AAA TAT C<u>G</u>T CTT TGG TGT TTC CTA TGA TGA ATA TA-3'

Sequence for the antisense strand of SEQ ID NO:2 was:

5'-TAT ATT CAT CAT AGG AAA CAC CAA AGA <u>C</u>GA TAT TTT CTT TAA TGG TGC CA-3'

SEQ ID NO:3 was a 50-mer mutant dsDNA target sequence identical to wild-type target DNA (SEQ ID NO:1) except for a consecutive two base pair mutation (underlined) at amino acid positions 506 and 507 at which the wild-type sense strand sequence CAT was changed to ACT.

Sequence for the sense strand of SEQ ID NO:3 was:

5'-TGG CAC CAT TAA AGA AAA TAT <u>AC</u>T CTT TGG TGT TTC CTA TGA TGA ATA TA-3'

Sequence for the antisense strand of SEQ ID NO:3 was:

5'-TAT ATT CAT CAT AGG AAA CAC CAA AGA <u>GT</u>A TAT TTT CTT TAA TGG TGC CA-3'

SEQ ID NO:4 was a 50-mer mutant dsDNA target sequence identical to wild-type target DNA (SEQ ID NO:1) except for a consecutive three base pair mutation (underlined) at amino acid positions 506 and 507 at which the wild-type sense strand sequence CAT was changed to ACG.

Sequence for the sense strand of SEQ ID NO:4 was:

5'-TGG CAC CAT TAA AGA AAA TAT <u>ACG</u> CTT TGG TGT TTC CTA TGA TGA ATA TA-3'

Sequence for the antisense strand of SEQ ID NO:4 was:

5'-TAT ATT CAT CAT AGG AAA CAC CAA AG<u>C</u> <u>GT</u>A TAT TTT CTT TAA TGG TGC CA-3'

SEQ ID NO:5 was a 47-mer mutant dsDNA target sequence identical to wild-type target DNA (SEQ ID NO:1) except for a consecutive three base pair deletion (indicated by three dots) at amino acid positions 507 and 508 at which the wild-type sense strand sequence CTT is deleted.

Sequence for the sense strand of SEQ ID NO:5 was:

5'-TGG CAC CAT TAA AGA AAA TAT CAT . . . TGG TGT TTC CTA TGA TGA ATA TA-3'

Sequence for the antisense strand of SEQ ID NO:5 was:

5'-TAT ATT CAT CAT AGG AAA CAC CA . . . A TGA TAT TTT CTT TAA TGG TGC CA-3'

Probe No. 1 was a 15-mer ssDNA probe designed to be completely complementary to a 15 nucleotide segment of the sense strand of the 50-mer wild-type target DNA (SEQ ID NO:1), overlapping amino acid positions 505 to 510 [Nature 380, 207 (1996)]. The chirality of the probe was opposite or antiparallel to that of the sense strand in the target. Probe No. 1 was synthesized on a DNA synthesizer, purified by HPLC, and dissolved in ddH$_2$O at a concentration of 1 pmole/µl.

Sequence for Probe No. 1 was:

5'-CAC CAA AGA TGA TAT-3'

The hybridization reaction mixture (120 µl) contained the following: 6 pmoles of target dsDNA, 6 pmoles of ssDNA probe, 0.5×TBE and 500 nM of the DNA intercalator YOYO-1 (Molecular Probes, Eugene, Oreg., USA). The reaction mixtures were incubated at room temperature (21° C.) for 5 minutes, placed into a quartz cuvette, irradiated with an argon ion laser beam having a wavelength of 488 nm and monitored repeatedly for fluorescent emission as the temperature increased with time, in a heated chamber. Concurrent temperature measurements of the samples were achieved by a software-controlled temperature probe placed directly into each sample. Maximum fluorescent intensities were plotted as a function of temperature for each sample analyzed.

FIG. 1 illustrates that the highest fluorescent intensities were achieved when the wild-type 50-mer non-denatured dsDNA target sequence (SEQ ID NO:1) was reacted with the 15-mer ssDNA Probe No. 1 from 30° C. to 85° C. At temperatures below 65° C., the T$_m$ of the 50-mer wild-type dsDNA, dsDNA:ssDNA complexes were formed, enhanced by the DNA intercalator YOYO-1. As the temperature increased above 65° C., the dsDNA:ssDNA complexes converted to ssDNA:ssDNA complexes. Clearly YOYO-1 was able to intercalate and fluoresce efficiently in both types of complexes.

In contrast, incompletely complementary probe and target combinations generating a 1 bp mismatch (SEQ ID NO:2+ Probe No. 1), a consecutive 2 bp mismatch (SEQ ID NO:3+Probe No. 1), a consecutive 3 bp mismatch (SEQ ID NO:4+Probe No. 1) and a 3 bp deletion (SEQ ID NO:5+ Probe No. 1) resulted in fluorescent intensities that were 57%, 94%, 97% and 98% lower at 30° C., and 47%, 79%, 92% and 91% lower at 65° C., respectively, than that observed with the perfectly matched sequences (FIG. 1). Control samples comprising 50-mer dsDNA targets plus 500 nM YOYO-1 exhibited levels of fluorescence which were at or below the level of fluorescence observed with 3 bp mismatched complexes at 30° C. (data not shown). The level of fluorescence emitted by the ssDNA Probe No. 1 plus 500 nM YOYO-1 sample was identical to that emitted by YOYO-1 alone (data not shown). As the temperature increased above 65° C., the degree of discrimination between perfect match and the base pair mismatches decreased, indicative of the gradual breakdown of the dsDNA:ssDNA structure. By 85° C., the fluorescent intensities achieved by a 1 bp mismatch, a 2 bp mismatch, a 3 bp mismatch and a 3 bp deletion were 40%, 63%, 92% and 83% lower than that obtained by the perfect match (FIG. 1). At any given temperature, the characteristic level of fluorescence emitted by each complex was monitored over time and was stable between 5 minutes and 24 hours.

The presence of the DNA decondensing agent, YOYO-1, allowed a ssDNA probe to be used to differentiate between perfectly complementary dsDNA:ssDNA complexes and those containing 1 bp, 2 bp or 3 bp mismatches or deletions, without the requirement for prior denaturation of dsDNA targets.

Example 2

To ensure that the fluorescent intensity assay using a DNA decondensing agent, ssDNA probes and non-denatured dsDNA targets, would apply to probe and target DNAs possessing dramatically different percent GC contents (and potentially different annealing temperatures), new 15-mer ssDNA probes and 50-mer dsDNA target sequences were synthesized, purified and annealed as above. Both ssDNA probes and dsDNA targets were dissolved in ddH$_2$O at a concentration of 1 pmole/µl.

SEQ ID NO:6 was a 50-mer dsDNA target sequence modified from SEQ ID NO:1, wherein the percent GC content was changed from 30% to 52%.

Sequence for the sense strand of the wild-type target DNA (SEQ ID NO:6) was:

5'-GAG CAC CAT GAC AGA CAC TGT CAT CTC TGG TGT GTC CTA CGA TGA CTC TG-3'

Sequence for the antisense strand of the wild-type target DNA (SEQ ID NO:6) was:

5'-CAG AGT CAT CGT AGG ACA CAC CAG AGA TGA CAG TGT CTG TCA TGG TGC TC-3'

SEQ ID NO:7 was a 50-mer mutant dsDNA target sequence identical to SEQ ID NO:6, except for a one base pair mutation (underlined), at which the sense strand sequence CTC was changed to CTT.

Sequence for the sense strand of mutant SEQ ID NO:7 was:

5'-GAG CAC CAT GAC AGA CAC TGT CAT CT<u>T</u> TGG TGT GTC CTA CGA TGA CTC TG-3'

Sequence for the antisense strand of mutant SEQ ID NO:7 was:

5'-CAG AGT CAT CGT AGG ACA CAC CA<u>A</u> AGA TGA CAG TGT CTG TCA TGG TGC TC-3'

SEQ ID NO:8 was a 50-mer mutant dsDNA target sequence identical to SEQ ID NO:6, except for a one base pair mutation (underlined), at which the sense strand sequence CAT was changed to CGT.

Sequence for the sense strand of mutant SEQ ID NO:8 was:

5'-GAG CAC CAT GAC AGA CAC TGT C<u>GT</u> CTC TGG TGT GTC CTA CGA TGA CTC TG-3'

Sequence for the antisense strand of mutant SEQ ID NO:8 was:

5'-CAG AGT CAT CGT AGG ACA CAC CAG AGA <u>C</u>GA CAG TGT CTG TCA TGG TGC TC-3'

SEQ ID NO:9 was a 50-mer mutant dsDNA target sequence identical to SEQ ID NO:6, except for a one base pair mutation (underlined), at which the sense strand sequence CAT was changed to CTT.

Sequence for the sense strand of mutant SEQ ID NO:9 was:

5'-GAG CAC CAT GAC AGA CAC TGT C<u>TT</u> CTC TGG TGT GTC CTA CGA TGA CTC TG-3'

Sequence for the antisense strand of mutant SEQ ID NO:9 was:

5'-CAG AGT CAT CGT AGG ACA CAC CAG AGA <u>A</u>GA CAG TGT CTG TCA TGG TGC TC-3'

SEQ ID NO:10 was a 50-mer mutant dsDNA target sequence identical to SEQ ID NO:6, except for a one base pair mutation (underlined), at which the sense strand sequence CTC was changed to CCC.

Sequence for the sense strand of mutant SEQ ID NO:10 was:

5'-GAG CAC CAT GAC AGA CAC TGT CAT C<u>C</u>C TGG TGT GTC CTA CGA TGA CTC TG-3'

Sequence for the antisense strand of mutant SEQ ID NO:10 was:

5'-CAG AGT CAT CGT AGG ACA CAC CAG <u>G</u>GA TGA CAG TGT CTG TCA TGG TGC TC-3'

SEQ ID NO:11 was a 50-mer mutant dsDNA target sequence identical to SEQ ID NO:6, except for a one base pair mutation (underlined), at which the sense strand sequence CTC was changed to CGC.

Sequence for the sense strand of mutant SEQ ID NO:11 was:

5'-GAG CAC CAT GAC AGA CAC TGT CAT C<u>G</u>C TGG TGT GTC CTA CGA TGA CTC TG-3'

Sequence for the antisense strand of mutant SEQ ID NO:11 was:

5'-CAG AGT CAT CGT AGG ACA CAC CAG <u>C</u>GA TGA CAG TGT CTG TCA TGG TGC TC-3'

SEQ ID NO:12 was a 50-mer mutant dsDNA target sequence identical to SEQ ID NO:6, except for a consecutive two base pair mutation (underlined), at which the sense strand sequence CAT was changed to ACT.

Sequence for the sense strand of mutant SEQ ID NO:12 was:

5'-GAG CAC CAT GAC AGA CAC TGT <u>ACT</u> CTC TGG TGT GTC CTA CGA TGA CTC TG-3'

Sequence for the antisense strand of mutant SEQ ID NO:12 was:

5'-CAG AGT CAT CGT AGG ACA CAC CAG AGA <u>GT</u>A CAG TGT CTG TCA TGG TGC TC-3'

SEQ ID NO:13 was a 50-mer dsDNA target sequence modified from SEQ ID NO:1, wherein the percent GC content was changed from 30% to 72%.

Sequence for the sense strand of the wild-type target DNA (SEQ ID NO:13) was:

5'-GAG CAC CCT CCC AGG CAC GGT CGT CCC TGG TGC GAC CTC CGA CGA GCG TG-3'

Sequence for the antisense strand of the wild-type target DNA (SEQ ID NO:13) was:

5'-CAC GCT CGT CGG AGG TCG CAC CAG GGA CGA CCG TGC CTG GGA GGG TGC TC-3'

SEQ ID NO:14 was a 50-mer mutant dsDNA target sequence identical to SEQ ID NO:13, except for a one base pair mutation (underlined), at which the sense strand sequence CGT was changed to CAT.

Sequence for the sense strand of mutant SEQ ID NO:14 was:

5'-GAG CAC CCT CCC AGG CAC GGT C<u>A</u>T CCC TGG TGC GAC CTC CGA CGA GCG TG-3'

Sequence for the antisense strand of mutant SEQ ID NO:14 was:

5'-CAC GCT CGT CGG AGG TCG CAC CAG GGA <u>T</u>GA CCG TGC CTG GGA GGG TGC TC-3'

SEQ ID NO:15 was a 50-mer mutant dsDNA target sequence identical to SEQ ID NO:13, except for a consecutive two base pair mutation (underlined), at which the sense strand sequence CGT was changed to ATT.

Sequence for the sense strand of mutant SEQ ID NO:15 was:

5'-GAG CAC CCT CCC AGG CAC GGT <u>ATT</u> CCC TGG TGC GAC CTC CGA CGA GCG TG-3'

Sequence for the antisense strand of mutant SEQ ID NO:15 was:

5'-CAC GCT CGT CGG AGG TCG CAC CAG GGA <u>AT</u>A CCG TGC CTG GGA GGG TGC TC-3'

Probe No. 2 was a 15-mer ssDNA probe designed to be completely complementary to a 15 nucleotide segment of the sense strand of the 50-mer wild-type target DNA (SEQ ID NO:6). The chirality of the probe was opposite or antiparallel to that of the sense strand in the target.

Sequence for Probe No. 2 was:

5'-CAC CAG AGA TGA CAG-3'

Probe No. 3 was a 15-mer ssDNA probe designed to be completely complementary to a 15 nucleotide segment of the sense strand of the 50-mer wild-type target DNA (SEQ ID NO:13). The chirality of the probe was opposite or antiparallel to that of the sense strand in the target.

Sequence for Probe No. 3 was:

5'-CAC CAG GGA CGA CCG-3'

The hybridization assay conditions were identical to that described in Example 1.

When the ssDNA Probe No. 2 (with a 53% GC content) was reacted with the 50-mer wild-type dsDNA target (SEQ ID NO:6) and mutant dsDNA targets (SEQ ID NO:8 and SEQ ID NO:12), dsDNA:ssDNA complexes were formed at low temperatures under non-denaturing conditions (FIG. 2A). While perfectly matched DNA complexes achieved the highest fluorescent intensities, incompletely complementary complexes with a 1 bp mismatch (SEQ ID NO:8+Probe No. 2) and a consecutive 2 bp mismatch (SEQ ID NO:12+Probe No. 2) produced fluorescent intensities that were 63% and 95% lower, respectively, than that observed with the perfectly matched sequences at 30° C. (FIG. 2A). As the temperature increased, the gradual breakdown of the dsDNA:ssDNA complex occurred, resulting in diminished fluorescent intensities and less discrimination between perfect match and the base pair mismatches. By 85° C., very little difference in fluorescence was seen between perfectly matched sequences and those containing base pair mismatches (FIG. 2A).

Similarly, in the presence of YOYO-1, dsDNA:ssDNA complexes were formed when the ssDNA Probe No. 3 (possessing a 73% GC content) was reacted with the corresponding 50-mer wild-type dsDNA target (SEQ ID NO:13) and mutant dsDNA targets (SEQ ID NO:14 and SEQ ID NO:15). The fluorescent intensities for a 1 bp mismatched DNA complex (SEQ ID NO:14+Probe No. 3) and a consecutive 2 bp mismatched DNA complex (SEQ ID NO:15+Probe No. 3) were 48% and 64% lower, respectively, than that obtained by the perfectly matched sequences at 30° C. (FIG. 2B). Fluorescence of all samples decreased as the temperature increased from 30° C. to 85° C., indicative of diminished YOYO-1 binding and dsDNA:ssDNA complex breakdown.

Regardless of the percent GC content of the ssDNA probes and dsDNA targets, YOYO-1 was able to facilitate dsDNA:ssDNA complex formation under non-denaturing conditions, to allow accurate discrimination between perfectly complementary sequences and those containing 1 or 2 bp mutations.

Example 3

The next examples will demonstrate the specificity of the assay utilizing different DNA condensing agents to promote and stabilize complex formation with non-denatured dsDNA targets and ssDNA-F probes.

Probe No. 4 was a 15-mer antiparallel ssDNA probe identical to Probe No. 1 except it had an attached fluorescein moiety at the 5' position. Probe No. 4 was synthesized on a DNA synthesizer, purified by HPLC, and dissolved in ddH$_2$O at a concentration of 1 pmole/µl.

Sequence for Probe No. 4 was:

5'-Flu-CAC CAA AGA TGA TAT-3'

The hybridization reaction mixture (40 µl) contained the following: 0.4 pmoles of target dsDNA, 4 pmoles of 5'-fluorescein labeled ssDNA Probe No. 4, 10 mM Tris-HCl, pH 7.5, and 10 mM to 125 mM NaCl. The reaction mixtures were incubated at room temperature (21° C.) for 1 hour, without prior denaturation of dsDNA targets. Samples were placed into a quartz cuvette, irradiated with an argon ion laser beam having a wavelength of 488 nm and monitored for fluorescent emission. The maximum fluorescent intensities occurred at a wavelength of 525 nm, the emission wavelength for fluorescein. The intensity of fluorescent emission was plotted as a function of wavelength for each sample analyzed.

In the absence of NaCl or presence of 10 mM or 25 mM NaCl, no binding between the dsDNA targets and the antiparallel ssDNA-F probe was detected (data not shown).

After a 1 hour incubation in the presence of 50 mM NaCl, dsDNA:ssDNA-F complexes consisting of perfectly complementary sequences (SEQ ID NO:1+Probe No. 4) formed readily, resulting in a 49% decrease in fluorescent emission intensity compared to that emitted by the control Probe No. 4 (labeled ssDNA-F) (FIG. 3). By contrast, incompletely complementary dsDNA:ssDNA-F complexes containing a 1 bp G-T mismatch (SEQ ID NO:2+Probe No. 4) yielded a 11% decrease in fluorescent emission intensity compared to that exhibited by the Probe No. 4 control sample.

The presence of 75 mM, 100 mM and 125 mM NaCl in the reaction mixture also resulted in fluorescent emission quenching consistent with significant amounts of complex formation between the perfectly matched SEQ ID NO:1 target and antiparallel Probe No. 4, and significantly less quenching when the 1 bp G-T mismatched SEQ ID NO:2 target and Probe No. 4 were present, producing similar fluorescent intensities to that observed in the presence of 50 mM NaCl (data not shown).

Use of monovalent cations, which are known DNA condensing agents, facilitated DNA complex formation between non-denatured dsDNA targets and fluorescently labeled antiparallel ssDNA probes, to allow reliable differentiation between perfectly complementary DNA sequences and those containing a single 1 bp mismatch. The reaction occurred at room temperature within 1 hour of incubation at a ratio of probe to target of 10 to 1. The dsDNA targets and ssDNA probe used in this example contained a 33% GC content, and did not contain homopurine or homopyrimidine stretches of DNA. Despite the presence of 6 pyrimidine bases interspersed within the 15 nucleotide ssDNA probe, dsDNA:ssDNA complexes formed readily in a sequence specific manner.

Example 4

To ensure that the fluorescent intensity assay, which used 5'-fluorescein labeled ssDNA probes and non-denatured dsDNA targets in the presence of DNA condensing agents such as cations, would apply to probe and target DNAs possessing dramatically different percent GC contents (and potentially different annealing preferences), 15-mer ssDNA-F probes and 50-mer dsDNA target sequences (with varying percent GC contents) were synthesized, purified and annealed as above. Both ssDNA-F probes and dsDNA targets were dissolved in ddH$_2$O at a concentration of 1 pmole/µl.

Probe No. 5 was a 15-mer antiparallel ssDNA probe identical to Probe No. 2 except it had an attached fluorescein moiety at the 5' position.

Sequence for Probe No. 5 was:

5'-Flu-CAC CAG AGA TGA CAG-3'

Probe No. 6 was a 15-mer antiparallel ssDNA probe identical to Probe No. 3 except it had an attached fluorescein moiety at the 5' position.

Sequence for Probe No. 6 was:

5'-Flu-CAC CAG GGA CGA CCG-3'

The assays performed in Example 3 were facilitated by the addition of monovalent cations in the reaction mixtures. The specificity of the assay was further examined utilizing divalent cations (instead of monovalent cations) to promote complex formation with dsDNA targets and ssDNA-F probes possessing various percent GC contents.

The hybridization reaction mixture (40 µl) contained the following: 0.4 pmoles of target dsDNA, 4 pmoles of 5'-fluorescein labeled ssDNA probe, 10 mM Tris-HCl, pH 7.5, and 5 mM to 30 mM $MnCl_2$ or 5 mM to 30 mM $MgCl_2$ or 5 mM to 30 mM $NiCl_2$. The reaction mixtures were incubated at room temperature (21° C.) for 1 hour, without prior denaturation of dsDNA targets. Samples were placed into a quartz cuvette, irradiated with an argon ion laser beam having a wavelength of 488 nm and monitored for fluorescent emission. The maximum fluorescent intensities occurred at a wavelength of 525 nm, the emission wavelength for fluorescein. The intensity of fluorescent emission was plotted as a function of wavelength for each sample analyzed.

When the ssDNA-F Probe No. 5 (with a 53% GC content) was incubated with the 50-mer wild-type dsDNA target (SEQ ID NO:6) and mutant dsDNA targets (SEQ ID NO:7 to SEQ ID NO:12) in the presence of 10 mM $MnCl_2$, dsDNA:ssDNA-F complexes were formed at room temperature under non-denaturing conditions. While perfectly matched DNA complexes yielded the maximum decrease in fluorescent intensity (a 43% decrease after a 1 hour incubation), the less stable dsDNA:ssDNA-F complexes containing a 1 bp T-G mismatch (SEQ ID NO:7+Probe No. 5) produced a fluorescent intensity that was 20% lower than that observed with Probe No. 5 alone after a 1 hour incubation (FIG. 4). dsDNA:ssDNA-F complexes that resulted in a 1 bp G-T mismatch (SEQ ID NO:8+Probe No. 5), a 1 bp T-T mismatch (SEQ ID NO:9+Probe No. 5), a 1 bp C-A mismatch (SEQ ID NO:10+Probe No. 5) and a consecutive 2 bp A-G and C-T mismatch (SEQ ID NO:12+Probe No. 5) were all less stable than the perfectly matched dsDNA:ssDNA-F complex (SEQ ID NO:6+Probe No. 5) yielding fluorescent intensities in between that observed for Probe No. 5 alone and that observed for the perfectly matched DNA complex (data not shown). Except for the 1 bp T-T mismatched dsDNA:ssDNA-F complex, which was the least stable (resulting in only a 5% decrease in fluorescent intensity after 1 hour), all of the other mismatched DNA complexes generated very similar fluorescent intensities. Only the dsDNA:ssDNA-F complex that contained a 1 bp G-A mismatch (SEQ ID NO:11+Probe No. 5) yielded a fluorescent intensity lower than that produced by the perfectly matched dsDNA:ssDNA-F complex (data not shown).

The inclusion of 20 mM $MgCl_2$ or 20 mM $MnCl_2$ or 20 mM $NiCl_2$ also facilitated dsDNA:ssDNA-F complex formation when the ssDNA-F Probe No. 6 (possessing a 73% GC content) was reacted with the corresponding 50-mer wild-type dsDNA target (SEQ ID NO:13) and mutant dsDNA target (SEQ ID NO:14) for 1 hour (data not shown). As expected, the perfectly matched dsDNA:ssDNA-F complexes generated the maximum decreases in fluorescent intensity, while the less stable 1 bp A-C mismatched dsDNA:ssDNA-F complexes (SEQ ID NO: 14+Probe No. 6) produced intermediate levels of fluorescence (data not shown).

Perfectly matched dsDNA:ssDNA-F complexes (possessing a 33% GC content) (SEQ ID NO:1+Probe No. 4) formed readily within 1 hour in the presence of 10 mM $MnCl_2$, resulting in a 57% decrease in fluorescent intensity compared to that emitted by Probe No. 4 alone (data not shown). These reaction conditions were highly unfavorable for dsDNA:ssDNA-F complexes that contained a 1 bp G-T mismatch (SEQ ID NO:2+Probe No. 4), resulting in an increased fluorescence compared to that observed by Probe No. 4 alone (data not shown).

Regardless of the percent GC content of the dsDNA targets and ssDNA probes, the addition of divalent cations such as $Mn^{+2}$, $Mg^{+2}$ or $Ni^{+2}$ promoted dsDNA:ssDNA complex formation under non-denaturing conditions, to allow accurate discrimination between perfectly complementary sequences and those containing 1 bp mutations.

Example 5

The dsDNA:ssDNA complex formation assays in Examples 3 and 4 were performed in the presence of one type of monovalent or divalent cation. The next Examples will demonstrate the reliability of the assay of the invention to differentiate between perfect matches and 1 bp mismatches in dsDNA:ssDNA complexes when combinations of divalent cations were used as promoting agents for complex formation.

The hybridization reaction mixture (40 µl) contained the following: 0.4 pmoles of target dsDNA, 4 pmoles of 5'-fluorescein labeled ssDNA probe, 10 mM Tris-HCl, pH 7.5, and 5 mM to 20 mM each of $MgCl_2$ and $MnCl_2$. The reaction mixtures were incubated at room temperature (21° C.) for 1 hour, without prior denaturation of dsDNA targets. Samples were placed into a quartz cuvette, irradiated with an argon ion laser beam having a wavelength of 488 nm and monitored for fluorescent emission. The intensity of fluorescence was plotted as a function of wavelength for each sample analyzed.

When the antiparallel ssDNA-F Probe No. 6 (with a 73% GC content) was incubated for 1 hour with the 50-mer wild-type dsDNA target (SEQ ID NO:13) in the presence of 20 mM $MgCl_2$ and 20 mM $MnCl_2$, perfectly complementary dsDNA:ssDNA-F complexes were formed efficiently, generating a 46% decrease in fluorescence compared to that emitted by Probe No. 6 alone (FIG. 5A). These reaction conditions were highly unfavorable for dsDNA:ssDNA-F complexes that contained a 1 bp A-C mismatch (SEQ ID NO:14+Probe No. 6), resulting in a 3% reduction in fluorescence compared to that observed with Probe No. 6 alone (FIG. 5A). Very similar results were obtained when the same samples were incubated for 1 hour in the presence of 10 mM $MgCl_2$ and 10 mM $MnCl_2$, or 15 mM $MgCl_2$ and 15 mM $MnCl_2$ (data not shown). The addition of 5 mM $MgCl_2$ and 5 mM $MnCl_2$ was insufficient to allow complex formation between the antiparallel ssDNA-F Probe No. 6 and all dsDNA targets tested following a 1 hour incubation (data not shown).

When the antiparallel ssDNA-F Probe No. 4 (with a 33% GC content) was incubated with the wild-type dsDNA target (SEQ ID NO:1) or mutant dsDNA targets (SEQ ID NO:2 and SEQ ID NO:3), in the presence of 10 mM $MgCl_2$ and 10 mM $MnCl_2$, minimal DNA complex formation was observed (data not shown). However, incubation in the presence of 15 mM $MgCl_2$ and 15 mM $MnCl_2$ for 1 hour facilitated perfectly matched dsDNA:ssDNA-F (SEQ ID NO:1 +Probe No. 4) complex formation, as evidenced by the 49% decrease in fluorescent intensity observed, compared to that obtained by Probe No. 4 (FIG. 5B). dsDNA:ssDNA-F complexes that resulted in a 1 bp G-T mismatch (SEQ ID NO:2+Probe No. 4) or a 3 bp deletion (SEQ ID NO:3+Probe No. 4) were very unstable in the presence of 15 mM $MgCl_2$ and 15 mM $MnCl_2$, yielding a 2% decrease in fluorescence and a 5% increase in fluorescence, respectively, compared to that emitted by Probe No. 4 alone (FIG. 5B). Treatment with 20 MM $MgCl_2$ and 20 mM $MnCl_2$ for 1 hour, resulted in a 68%, a 48% and a 6% reduction in fluorescence for perfectly matched dsDNA:ssDNA-F complexes, and for dsDNA:ssDNA-F complexes containing a 1 bp G-T mismatch or a 3 bp deletion, respectively, compared to that observed with Probe No. 4 alone (data not shown).

As illustrated in FIG. 5C, in the presence of 10 mM $MgCl_2$ and 10 mM $MnCl_2$, the dsDNA:ssDNA-F complexes possessing a 53% GC content and containing perfectly complementary sequences (SEQ ID NO:6+Probe No. 5) or a 1 bp T-G mismatch (SEQ ID NO:7+Probe No. 5) generated fluorescent intensities after an 1 hour incubation that were 68% and 20% lower, respectively, than that emitted by the antiparallel Probe No. 5 alone.

When the antiparallel ssDNA-F Probe No. 5 (with a 53% GC content) was incubated for 1 hour with the 50-mer wild-type dsDNA target (SEQ ID NO:6) in the presence of 15 mM $MgCl_2$ and 15 mM $MnCl_2$, perfectly complementary dsDNA:ssDNA-F complexes were formed very efficiently, generating a 74% decrease in fluorescence compared to that achieved by Probe No. 5 alone (FIG. 5D). By contrast, dsDNA:ssDNA-F complexes that contained a 1 bp T-G mismatch (SEQ ID NO:7+Probe No. 5) were much less stable in the presence of 15 mM $MgCl_2$ and 15 mM $MnCl_2$, yielding a 15% decrease in fluorescence compared to that emitted by Probe No. 5 alone after a 1 hour incubation (FIG. 5D). Similarly, dsDNA:ssDNA-F complexes that resulted in a 1 bp G-T mismatch (SEQ ID NO:8+Probe No. 5), a 1 bp C-A mismatch (SEQ ID NO:10+Probe No. 5), a 1 bp G-A mismatch (SEQ ID NO:11 +Probe No. 5) and a consecutive 2 bp A-G and C-T mismatch (SEQ ID NO:12+Probe No. 5) were all much less stable than the perfectly matched DNA complex (data not shown). When Probe No. 5 (containing a 53% GC content) was reacted with the dsDNA target SEQ ID NO:3 (containing a 33% GC content), a 3% increase in fluorescence was observed compared to that obtained by Probe No. 5 alone (FIG. 5D), indicative of no DNA complex formation. This result was expected considering this probe and target combination would result in a 5 bp mismatch.

Collectively, Examples 3, 4 and 5 demonstrated that the addition of condensing agents such as monovalent cations or divalent cations (on their own or in combination), promoted DNA complex formation between dsDNA targets and fluorescently-labeled ssDNA probes, possessing dramatically different percent GC contents, to allow accurate and reliable discrimination between perfectly complementary sequences and those containing various 1 bp mutations.

Example 6

DsDNA:ssDNA complexes facilitated by YOYO-1 readily form at room temperature within 5 minutes of incubation and generate fluorescent emissions at the same level of intensity for hours. Complexes containing base pair mismatches similarly emit fluorescent signals which persist, indicating the same level of complex formation over time. To examine the rate of formation, stability and rate of disassociation of dsDNA:ssDNA complexes formed in the presence of condensing agents such as cations, time course experiments were performed.

The hybridization reaction mixture (40 μl) contained the following: 0.4 pmoles of non-denatured target dsDNA, 4 pmoles of 5'-fluorescein labeled ssDNA probe, 10 mM Tris-HCl, pH 7.5, and 10 mM $MgCl_2$ and 10 mM $MnCl_2$. The reaction mixtures were incubated at room temperature (21° C.) for various periods ranging from 1 minute to 2 hours. Following incubation, samples were placed into a quartz cuvette, irradiated once with an argon ion laser beam having a wavelength of 488 nm and monitored for fluorescent emission. Further fluorescent measurements were taken of the same samples after subsequent multiple laser irradiation, at the indicated times (FIG. 6). The intensity of fluorescence was plotted as a function of time for each sample analyzed.

The fluorescence emitted by control samples comprising 4 pmoles of Probe No. 5 plus 10 mM $MgCl_2$ and 10 mM $MnCl_2$, in the absence of target dsDNA, dramatically decreased 3-fold within just 5 minutes of incubation (data not shown), and then steadily declined at a much slower rate within the next few hours (FIG. 6A). This effect we refer to as "Cationic Quench". This inhibition of fluorescence, associated with increased incubation periods of ssDNA-F probes with specific cations, occurred routinely in the presence of divalent cations, but not in the presence of monovalent cations (data not shown). This observation makes evident the importance of incubating the control sample in an experiment under exactly the same conditions that the test samples of an experiment are reacted. Multiple lasing of each ssDNA-F control sample after varying periods of incubation inhibited further quenching of the fluorophore, resulting in a steady level of fluorescence thereafter (FIG. 6A). This result was entirely unanticipated.

When the antiparallel ssDNA-F Probe No. 5 was incubated with the 50-mer wild-type dsDNA target (SEQ ID NO:6) in the presence of 10 mM $MgCl_2$ and 10 mM $MnCl_2$, dsDNA:ssDNA-F complex formation was evident after 15 minutes of incubation resulting in a decrease in fluorescence, which was 6% greater than the progressive cationic quench of the control Probe No. 5 (FIG. 6B). Complex formation was greatly indicated after 30 and 60 minutes of incubation of SEQ ID NO:6 with Probe No. 5 in the presence of 10 mM $MgCl_2$ and 10 mM $MnCl_2$, generating a 76% and 61% decrease in fluorescence, respectively, compared to that achieved by the cationically quenched Probe No. 5 alone (FIG. 6B). After 90 and 120 minutes of incubation in the presence of 10 mM $MgCl_2$ and 10 mM $MnCl_2$, no complex formation was being signaled (FIG. 6B). The level of fluorescent emission seen at 90 and 120 minutes was wholly attributable to the cationic quench effect (compare FIGS. 6A and 6B).

By contrast, dsDNA:ssDNA-F complexes that contained a 1 bp T-G mismatch (SEQ ID NO:7+Probe No. 5) formed at a slower rate and were much less stable once formed in the presence of 10 mM $MgCl_2$ and 10 mM $MnCl_2$. The 1 bp T-G mismatched complex was first observed after 30 minutes of incubation, and appeared to have been eliminated after 60 minutes of incubation (FIG. 6C). Once again, the probe was antiparallel to the complementary strand in the duplex (FIG. 6C).

Multiple laser irradiation of perfectly complementary dsDNA:ssDNA-F complexes (SEQ ID NO:6+Probe No. 5) formed after 30 minutes or 60 minutes of incubation in the presence of 10 mM MgCl$_2$ and 10 mM MnCl$_2$ resulted in fluorescent emissions consistent with the destruction of these complexes at a rate characteristic for DNA complexes containing an antiparallel ssDNA probe (FIG. 6B). When a subsequent measurement was made at 45 minutes after lasing of the perfectly complementary complex at 30 minutes, the emission intensity level was 1869, testimony to the rapidity with which the complex was destroyed (data not shown). The level of fluorescent emission, after multiple lasing, returned to the cationically quenched values observed by the uncomplexed Probe No. 5 alone control (compare FIGS. 6A and 6B). The only exception was the perfectly matched complexes formed after 15 minutes of incubation and repeated irradiated thereafter (FIG. 6B). In this case the fluorescent emission was not consistent with the destruction of the complexes (FIG. 6B), even though further cationic quench of Probe No. 5, when multiply irradiated after a 15 minute incubation, was totally inhibited (FIG. 6A). DsDNA:ssDNA-F complexes containing a 1 bp T-G mismatch (SEQ ID NO:7+Probe No. 5) were similarly apparently destroyed by multiple lasing (FIG. 6C).

An experiment was performed to determine the basis for the effect of multiple lasing on the complexes. It was found that when fresh cations were added to the reaction mixture which had been lased twice, the inhibition of cationic quench in fluorescence emitted by the ssDNA-F probe could not be reversed and further cationic quench did not occur upon further incubation, strongly suggesting that the ssDNA-F probe was inactivated by multiple irradiation, by a yet unknown mechanism (data not shown). Similarly, when fresh ssDNA-F probes were added to the reaction mixture which had been lased twice, after normalizing for the increased fluorescent emission of the fresh probe, no subsequent progressive cationic quenching was observed upon further incubation of the reaction mixture, strongly suggesting that the lased cations were somehow disabled (data not shown).

Example 7

Examples 1–6 demonstrated dsDNA:ssDNA complex formation in a sequence specific manner between dsDNA targets and ssDNA probes facilitated by either DNA decondensing agents such as YOYO-1 or by DNA condensing agents such as monovalent or divalent cations. The next examples will examine the rate of formation, stability and rate of disassociation of dsDNA:dsDNA complexes formed in the presence of various cations. These examples will show how the species of cation, the concentration of each cation, and the combination of different cations at different concentrations influence the rate of formation, stability and rate of disassociation of dsDNA:dsDNA complexes formed.

Complementary sense and antisense 15-mer ssDNA probe sequences were synthesized on a DNA synthesizer and purified by HPLC. Equimolar amounts of the complementary oligonucleotides were heated at 95° C. for 10 min and allowed to anneal gradually as the temperature cooled to 21° C. over 1.5 hours. DsDNA oligonucleotides were dissolved in ddH$_2$O at a concentration of 1 pmole/μl.

Probe No. 7 was a 15 bp dsDNA probe with an attached fluorescein moiety at each 5' position, designed to be completely homologous to a 15 bp segment of the 50-mer wild-type target DNA (SEQ ID NO:6). The antisense strand of Probe No. 7 was identical to Probe No. 5.

Sequence for the sense strand of Probe No. 7 was:

5'-Flu-CTG TCA TCT CTG GTG-3'

Sequence for the antisense strand of Probe No. 7 was:

5'-Flu-CAC CAG AGA TGA CAG-3'

The hybridization reaction mixture (40 μl) contained the following: 0.4 pmoles of non-denatured target dsDNA, 4 pmoles of 5'-fluorescein labeled dsDNA probe, 10 mM Tris-HCl, pH 7.5, 70 mM to 90 mM KCl and 0 mM to 20 mM NaCl. The reaction mixtures were incubated at room temperature (21° C.) for various periods ranging from 1 minute to 2 hours. Following incubation, samples were placed into a quartz cuvette, irradiated once with an argon ion laser beam having a wavelength of 488 nm and monitored for fluorescent emission. The intensity of fluorescence was plotted as a function of time for each sample analyzed.

The fluorescence emitted by control samples, comprising 4 pmoles of Probe No. 7 plus 90 mM KCl in the absence of target dsDNA, remained relatively constant throughout the 120 minute incubation, indicating that no cationic quenching of the dsDNA-F probe was occurring in the presence of the monovalent KCl (FIG. 7A). When the dsDNA-F Probe No. 7 was incubated with the 50-mer wild-type dsDNA target (SEQ ID NO:6) and mutant dsDNA target (SEQ ID NO:7) in the presence of 90 mM KCl, dsDNA:dsDNA-F complexes were formed at room temperature under non-denaturing conditions within just 15 minutes of incubation and persisted for at least 120 minutes (FIG. 7A). Maximum discrimination between perfectly matched and 1 bp mismatched dsDNA:dsDNA-F complexes was observed after 30 and 45 minutes of incubation in the presence of 90 mM KCl, generating fluorescent intensities that were 27% and 3% lower, respectively after 30 minutes, and 34% and 15% lower, respectively after 45 minutes, than that emitted by Probe No. 7 alone (FIG. 7A).

In the presence of 70 mM KCl and 20 mM NaCl, the dsDNA:dsDNA-F complexes containing perfectly matched sequences (SEQ ID NO:6+Probe No. 7) or a 1 bp mismatch (SEQ ID NO:7+Probe No. 7) produced fluorescent intensities that were 47% and 19% lower, respectively after 30 minutes, and 35% and 14% lower, respectively after 45 minutes, than that achieved by Probe No. 7 alone (FIG. 7B). A small amount of cationic quench of the dsDNA-F Probe No. 7 control sample was observed over the 120 minute incubation in the presence of 70 mM KCl and 20 mM NaCl (FIG. 7B). This minimal cationic quench was caused by the inclusion of NaCl, which when present alone causes a similar progressive fluorescence quench of Probe No. 7 (data not shown).

The presence of 80 mM KCl and 10 mM NaCl, preferentially promoted perfectly matched dsDNA:dsDNA-F complex formation between the wild-type dsDNA target (SEQ ID NO:6) and dsDNA-F Probe No. 7, resulting in a decrease in fluorescent emission of 18%, 48% and 34% after a 30 minute, 45 minute and 60 minute incubation, respectively, compared to the fluorescence emitted by the control Probe No. 7 sample at these times (FIG. 7C). By contrast, formation of the 1 bp mismatched dsDNA:dsDNA-F complexes (SEQ ID NO:7+Probe No. 7) was very inefficient throughout the entire 120 minute incubation in the presence of 80 mM KCl and 10 mM NaCl, as evidenced by the low 1% to 5% reduction in fluorescence observed with these mismatched complexes compared to that exhibited by Probe No. 7 (FIG. 7C).

Therefore the inclusion of monovalent cations such as KCl and NaCl at close to physiological concentrations promoted DNA complex formation between non-denatured dsDNA targets and fluorescently-labeled dsDNA probes. Complex formation occurred on the basis of homologous base pair recognition, with a measurable and significantly greater amount of complex formation between fully matched homologous duplex strands. The reaction occurred at room temperature within relatively short incubation periods of 15 minutes to 60 minutes at a ratio of probe to target of 10 to 1. The dsDNA targets and dsDNA probe used in this example were homologous, contained 53% GC content, and did not contain homopurine or homopyrimidine stretches on any DNA strand. The assay of the invention was able to identify perfectly matched dsDNA sequences and those containing a pair of mismatched bases, using dsDNA probes.

Example 8

The assays performed in Example 7 were facilitated by the addition of monovalent cations in the reaction mixtures. This example will demonstrate the rate of formation, stability and rate of dissassociation of dsDNA:dsDNA complexes formed in the presence of divalent cations. The reaction conditions were identical to that described in Example 7, except that KCl and NaCl was replaced with 30 mM to 40 mM each of $MgCl_2$ and $MnCl_2$.

The control dsDNA-F Probe No. 7 sample exhibited a progressive reduction in fluorescence with increased time of incubation in the presence of 30 mM $MgCl_2$ and 30 mM $MnCl_2$ (FIG. 8A) or 40 mM $MgCl_2$ and 40 mM $MnCl_2$ (FIG. 8B). This cationic quench was similar to that observed with ssDNA-F Probe No. 5 in the presence of 10 mM $MgCl_2$ and 10 mM $MnCl_2$ (FIG. 6A).

When the dsDNA-F Probe No. 7 was incubated with the 50-mer wild-type dsDNA target (SEQ ID NO:6) in the presence of 30 mM $MgCl_2$ and 30 mM $MnCl_2$, dsDNA:dsDNA-F complex formation was evident after 60 minutes of incubation resulting in a decrease in fluorescence, which was 13% greater than the progressive cationic quench of the control Probe No. 7 (FIG. 8A). Complex formation was greatly indicated after 75 minutes of incubation of SEQ ID NO:6 with Probe No. 7 in the presence of 30 mM $MgCl_2$ and 30 mM $MnCl_2$, generating an 81% decrease in fluorescence, compared to that achieved by the cationically quenched Probe No. 7 alone (FIG. 8A). DsDNA:dsDNA-F complexes that contained a 1 bp mismatch (SEQ ID NO:7+Probe No. 7) also formed after 60 minutes and 75 minutes of incubation in the presence of 30 mM $MgCl_2$ and 30 mM $MnCl_2$, generating a 16% and 30% decrease in fluorescence, respectively, compared to that achieved by the cationically quenched Probe No. 7 alone (FIG. 8A). After 90 and 120 minutes of incubation in the presence of 30 mM $MgCl_2$ and 30 mM $MnCl_2$, no complex formation was being signaled (FIG. 8A). After 90 minutes, the level of fluorescence observed was wholly attributable to the cationic quench effect (FIG. 8A).

In the presence of 40 mM $MgCl_2$ and 40 mM $MnCl_2$, the dsDNA:dsDNA-F complexes containing perfectly matched sequences (SEQ ID NO:6+Probe No. 7) or a 1 bp mismatch (SEQ ID NO:7+Probe No. 7) produced fluorescent intensities that were 17% lower and 4% higher, respectively after 60 minutes, 36% and 22% lower, respectively after 75 minutes, and 57% lower and 0.2% higher, respectively after 90 minutes, than that emitted by the cationically quenched Probe No. 7 alone (FIG. 8B). After 120 minutes of incubation in the presence of 40 mM $MgCl_2$ and 40 mM $MnCl_2$, no complex formation was being signaled (FIG. 8B).

The addition of divalent cations, such as $MgCl_2$ and $MnCl_2$, facilitated DNA complex formation between non-denatured dsDNA targets and fluorescently-labeled dsDNA probes, to allow accurate discrimination between perfectly matched homologous sequences and those containing 1 bp mutations. Approximately double the concentration of both $MgCl_2$ and $MnCl_2$ was required for the formation of dsDNA:dsDNA complexes compared to that required for the formation of dsDNA:ssDNA complexes. The rate of formation of the dsDNA:dsDNA complexes was slower in the presence of divalent cations than in the presence of monovalent cations. Once formed the divalent cation induced dsDNA:dsDNA complexes seemed to be stable over a shorter time period.

Example 9

The rate of formation, stability and rate of dissassociation of dsDNA:dsDNA complexes formed in the presence of monovalent and divalent cations was examined next. The hybridization reaction mixture (40 µl) contained the following: 0.4 pmoles of non-denatured target dsDNA, 4 pmoles of 5'-fluorescein labeled dsDNA probe, 10 mM Tris-HCl, pH 7.5, 60 mM to 80 mM KCl, 10 mM to 20 mM NaCl, 30 mM $MgCl_2$ and 30 mM $MnCl_2$. The reaction mixtures were incubated at room temperature (21° C.) for various periods ranging from 1 minute to 150 minutes. Following incubation, samples were placed into a quartz cuvette, irradiated once with an argon ion laser beam having a wavelength of 488 nm and monitored for fluorescent emission. The intensity of fluorescence was plotted as a function of time for each sample analyzed.

The presence of various KCl and NaCl concentrations together with 30 mM $MgCl_2$ and 30 mM $MnCl_2$ resulted in a cationic quench in fluorescence of control dsDNA-F Probe No. 7 (FIG. 9) that was very similar to that observed in the presence of only the divalent cations (FIG. 8). It seems that the inclusion of the monovalent cations did not affect the cationic quench of the dsDNA-F probe by the divalent cations.

When the dsDNA-F Probe No. 7 was incubated with the 50-mer wild-type dsDNA target (SEQ ID NO:6) and mutant dsDNA target (SEQ ID NO:7) in the presence of 60 mM KCl, 20 mM NaCl, 30 mM $MgCl_2$ and 30 mM $MnCl_2$, dsDNA:dsDNA-F complexes were formed at room temperature under non-denaturing conditions within just 15 minutes of incubation and persisted for at least 150 minutes (FIG. 9A). Maximum discrimination between perfectly matched and 1 bp mismatched dsDNA:dsDNA-F complexes was observed after 30, 45 and 150 minutes of incubation, generating fluorescent intensities that were 43% and 16% lower, respectively after 30 minutes, 38% and 16% lower, respectively after 45 minutes, and 65% and 1% lower, respectively after 150 minutes, than that emitted by the cationically quenched Probe No. 7 alone (FIG. 9A).

In the presence of 70 mM KCl, 20 mM NaCl, 30 mM $MgCl_2$ and 30 mM $MnCl_2$, the dsDNA:dsDNA-F complexes containing perfectly matched sequences (SEQ ID NO:6+Probe No. 7) or a 1 bp mismatch (SEQ ID NO:7+Probe No. 7) produced fluorescent intensities that were 17% and 1% lower, respectively after 60 minutes, 48% and 11% lower, respectively after 75 minutes, 22% and 3% lower, respectively after 90 minutes, and 34% and 2% lower, respectively after 120 minutes, than that achieved by the cationically quenched Probe No. 7 alone (FIG. 9B).

The presence of 80 mM KCl, 10 mM NaCl, 30 mM $MgCl_2$ and 30 mM $MnCl_2$, preferentially promoted perfectly matched dsDNA:dsDNA-F complex formation between the wild-type dsDNA target (SEQ ID NO:6) and dsDNA-F Probe No. 7, after 30 minutes to 120 minutes of incubation. The perfectly matched dsDNA:dsDNA-F complexes generated a decrease in fluorescent emission of 27%, 43%, 29% and 52% after a 60 minute, 75 minute, 90 minute and 120 minute incubation, respectively, compared to the fluorescence emitted by the cationically quenched Probe No. 7 sample at these times (FIG. 9C). By contrast, formation of the 1 bp mismatched dsDNA:dsDNA-F complexes (SEQ ID NO:7+Probe No. 7) was very inefficient following a 45 minute to 90 minute incubation in the presence of 80 mM KCl, 10 mM NaCl, 30 mM $MgCl_2$ and 30 mM $MnCl_2$, as evidenced by the low 2% to 3% reduction in fluorescence observed with these mismatched complexes compared to that exhibited by the cationically quenched Probe No. 7 (FIG. 9C). Minimal 1 bp mismatched dsDNA:dsDNA-F complex formation occurred after 120 minutes of incubation, resulting in a 14% decrease in fluorescence compared to that emitted by the cationically quenched Probe No. 7.

The presence of both monovalent and divalent cations promoted dsDNA:dsDNA complex formation at a faster rate than did divalent cations alone. Once formed the complexes facilitated by both types of cations persisted for a longer time than did the complexes promoted by either monovalent cations or divalent cations separately. Maximum discrimination between perfectly matched and 1 bp mismatched dsDNA:dsDNA-F complexes was observed for a longer time interval in the presence of both monovalent and divalent cations. Therefore physiological concentrations of KCl, NaCl and $MgCl_2$ preferentially facilitated complex formation between fully matched homologous duplex strands, on the basis of homologous base pair recognition.

Example 10

Examples 3–6 demonstrated dsDNA:ssDNA complex formation in a sequence specific manner between dsDNA targets and ssDNA probes facilitated by DNA condensing agents such as monovalent or divalent cations. The next example will examine the rate of formation, stability and rate of disassociation of dsDNA:ssDNA complexes formed in the presence of the multivalent cation, spermidine (possessing a charge of +3), which is also capable of condensing DNA.

The hybridization reaction mixture (40 µl) contained the following: 0.2 pmoles of non-denatured target dsDNA, 2 pmoles of 5'-fluorescein labeled ssDNA probe, 10 mM Tris-HCl, pH 7.5, and 1 mM spermidine. The reaction mixtures were incubated at room temperature (21° C.) for various periods ranging from 1 minute to 2 hours. Following incubation, samples were placed into a quartz cuvette, irradiated once with an argon ion laser beam having a wavelength of 488 nm and monitored for fluorescent emission. The intensity of fluorescence was plotted as a function of time for each sample analyzed.

The control ssDNA-F Probe No. 5 exhibited a progressive reduction in fluorescence with increased incubation time in the presence of 1 mM spermidine (FIG. 10). This cationic quench was not as pronounced as that observed when the same probe was incubated in the presence of 10 mM $MgCl_2$ and 10 mM $MnCl_2$, especially within the first 5 minutes of incubation (FIG. 6A).

Perfectly complementary dsDNA:ssDNA-F complex formation between the dsDNA target (SEQ ID NO:6) and the ssDNA-F Probe No. 5 was indicated after just 15 and 30 minutes of incubation in the presence of 1 mM spermidine, generating a 11% and 20% decrease in fluorescence, respectively, compared to that achieved by the cationically quenched Probe No. 5 alone (FIG. 10). After 45 minutes of incubation in the presence of 1 mM spermidine, minimal complex formation was being signaled (FIG. 10).

The inclusion of 1 mM spermidine was highly unfavourable for dsDNA:ssDNA-F complex formation that contained a 1 bp T-G mismatch (SEQ ID NO:7+Probe No. 5), as evidenced by an increased fluorescence of 11% and 7% compared to that observed by the cationically quenched Probe No. 5 after 15 minutes and 30 minutes of incubation, respectively (FIG. 10). Minimal complex formation involving incompletely complementary sequences appeared only after 75 minutes of incubation in the presence of 1 mM spermidine and disappeared by 120 minutes.

The addition of the DNA condensing agent, spermidine, facilitated rapid dsDNA:ssDNA complex formation between perfectly matched sequences under non-denaturing conditions, to allow differentiation between perfectly complementary sequences and those containing a 1 bp mutation.

Example 11

Many different agents besides cations are capable of condensing dsDNA. Example 11 demonstrates the rate of formation, stability and rate of disassociation of dsDNA:ssDNA complexes formed in the presence of ethanol, another type of DNA condensing agent.

The hybridization reaction mixture (40 µl) contained the following: 0.2 pmoles of non-denatured target dsDNA, 2 pmoles of 5'-fluorescein labeled ssDNA probe, 10 mM Tris-HCl, pH 7.5, and 10% ethanol. The reaction mixtures were incubated at room temperature (21° C.) for various periods ranging from 1 minute to 90 minutes. Following incubation, samples were placed into a quartz cuvette, irradiated once with an argon ion laser beam having a wavelength of 488 nm and monitored for fluorescent emission. The intensity of fluorescence was plotted as a function of time for each sample analyzed.

Unlike divalent or multivalent cations, the addition of 10% ethanol did not result in a quench in fluorescence emitted by the control ssDNA-F Probe No. 5, but actually caused a slight increase in fluorescence of the probe over time (FIG. 11).

The presence of 10% ethanol preferentially promoted perfectly complementary dsDNA:ssDNA-F complex formation between the wild-type dsDNA target (SEQ ID NO:6) and ssDNA-F Probe No. 5 following a 15 minute to 60 minute incubation (FIG. 11). By contrast, formation of the 1 bp T-G mismatched dsDNA:ssDNA-F complex (SEQ ID NO:7+Probe No. 5) was very inefficient during this incubation time in the presence of 10% ethanol. The fluorescent intensities produced by the perfectly matched complexes and 1 bp mismatched complexes were 11% and 2% lower, respectively after 15 minutes, 12% and 1% lower, respectively after 30 minutes, 25% and 2% lower, respectively after 45 minutes, and 13% and 7% lower, respectively after 60 minutes, than that emitted by the Probe No. 5 control (FIG. 11). No significant dsDNA:ssDNA-F complex formation was observed after a 75 minute incubation in the presence of 10% ethanol.

The addition of low concentrations of ethanol, facilitated DNA complex formation between non-denatured dsDNA targets and fluorescently-labeled ssDNA probes, to allow discrimination between perfectly complementary sequences and those containing a 1 bp mutation.

Example 12

Example 12 demonstrates that the assay of the invention can discriminate between perfectly complementary dsDNA:ssDNA complexes and dsDNA:ssDNA complexes containing every type of 1 bp mismatch possible, when the cationic DNA intercalator YOYO-1 is present.

Complementary sense and antisense 15-mer ssDNA probes were synthesized on a DNA synthesizer, purified by HPLC, and dissolved in ddH$_2$O at a concentration of 1 pmole/μl. Probe No. 1 was a 15-mer ssDNA probe designed to be completely complementary to a 15 nucleotide segment of the sense strand of the 50-mer wild-type target DNA (SEQ ID NO:1), overlapping amino acid positions 505 to 510 [Nature 380, 207 (1996)]. The chirality of the probe was opposite or antiparallel to that of the sense strand in the target. Mutant probes (Probe No. 8 to Probe No. 16) were identical in sequence to Probe No. 1 except for a 1 base mutation (underlined).

```
Sequence for Probe No. 1 was:
5'-CAC CAA AGA TGA TAT-3'

Sequence for Probe No. 8 was:
5'-CAC CAA AGA AGA TAT-3'

Sequence for Probe No. 9 was:
5'-CAC GAA AGA TGA TAT-3'

Sequence for Probe No. 10 was:
5'-CAC CAA ACA TGA TAT-3'

Sequence for Probe No. 11 was:
5'-CAC CAT AGA TGA TAT-3'

Sequence for Probe No. 12 was:
5'-CAC CAG AGA TGA TAT-3'

Sequence for Probe No. 13 was:
5'-CAC CAC AGA TGA TAT-3'

Sequence for Probe No. 14 was:
5'-CAC CAA AGA CGA TAT-3'

Sequence for Probe No. 15 was:
5'-CAC CAA AAA TGA TAT-3'

Sequence for Probe No. 16 was:
5'-CAC AAA AGA TGA TAT-3'
```

Probe No. 17 was a 15-mer ssDNA probe designed to be completely complementary to a 15 nucleotide segment of the antisense strand of the 50-mer wild-type target DNA (SEQ ID NO:1), overlapping amino acid positions 505 to 510 [Nature 380, 207 (1996)]. The chirality of the probe was opposite or antiparallel to that of the antisense strand in the target. Mutant probes (Probe No. 18 to Probe No. 26) were identical in sequence to Probe No. 17 except for a 1 base mutation (underlined).

```
Sequence for Probe No. 17 was:
5'-ATA TCA TCT TTG GTG-3'

Sequence for Probe No. 18 was:
5'-ATA TCT TCT TTG GTG-3'

Sequence for Probe No. 19 was:
5'-ATA TCA TCT TTC GTG-3'

Sequence for Probe No. 20 was:
5'-ATA TCA TGT TTG GTG-3'

Sequence for Probe No. 21 was:
5'-ATA TCA TCT ATG GTG-3'

Sequence for Probe No. 22 was:
5'-ATA TCA TCT CTG GTG-3'

Sequence for Probe No. 23 was:
5'-ATA TCA TCT GTG GTG-3'

Sequence for Probe No. 24 was:
5'-ATA TCG TCT TTG GTG-3'

Sequence for Probe No. 25 was:
5'-ATA TCA TTT TTG GTG-3'

Sequence for Probe No. 26 was:
5'-ATA TCA TCT TTT GTG-3'
```

The hybridization reaction mixture (40 μl) contained the following: 2 pmoles of target dsDNA, 2 pmoles of ssDNA probe, 0.5×TBE and 500 nM of the DNA intercalator YOYO-1. The reaction mixtures were incubated at room temperature (21° C.) for 5 minutes, without prior denaturation of dsDNA targets. Samples were placed into a quartz cuvette, irradiated with an argon ion laser beam having a wavelength of 488 nm and monitored for fluorescent emission. The intensity of fluorescent emission was plotted as a function of wavelength for each sample analyzed.

The 50-mer wild-type non-denatured dsDNA target (SEQ ID NO:1) was reacted with the 15-mer wild-type antisense ssDNA Probe No. 1 and various 15-mer 1 base mutated antisense ssDNA probes (Probe No. 8 to Probe No. 16), that would generate every type of 1 bp mismatch possible. As expected, the highest fluorescent emission intensities were generated by the dsDNA:ssDNA complexes consisting of perfectly complementary sequences (SEQ ID NO:1+Probe No. 1) (FIGS. 12A and 12B). DsDNA:ssDNA complexes that resulted in a 1 bp A-A mismatch (SEQ ID NO:1+Probe No. 8), a 1 bp G-G mismatch (SEQ ID NO:1+Probe No. 9), a 1 bp C-C mismatch (SEQ ID NO:1+Probe No. 10), a 1 bp T-T mismatch (SEQ ID NO:1+Probe No. 11), a 1 bp T-G mismatch (SEQ ID NO:1+Probe No. 12), a 1 bp T-C mismatch (SEQ ID NO:1+Probe No. 13), a 1 bp A-C mismatch (SEQ ID NO:1+Probe No. 14), a 1 bp C-A mismatch (SEQ ID NO:1+Probe No. 15), and a 1 bp G-A mismatch (SEQ ID NO:1+Probe No. 16) produced fluorescent emission intensities that were 63%, 66%, 50%, 47%, 49%, 79%, 57%, 51% and 71% lower, respectively, than that emitted by the perfectly matched dsDNA:ssDNA complexes (FIGS. 12A and 12B).

The triple strand assay was also evaluated by reacting the 50-mer wild-type non-denatured dsDNA target (SEQ ID NO:1) with the 15-mer wild-type sense ssDNA Probe No. 17 and various 15-mer 1 base mutated sense ssDNA probes (Probe No. 18 to Probe No. 26), that would generate every type of 1 bp mismatch possible. The perfectly complementary dsDNA:ssDNA triple strand complexes (SEQ ID NO:1+Probe No. 17) containing a sense strand probe (FIGS. 12C and 12D) formed with similar efficacy as the perfectly complementary triple strand complexes (SEQ ID NO:1–Probe No. 1) containing an antisense strand probe (FIGS. 12A and 12B). DsDNA:ssDNA complexes that resulted in a 1 bp T-T mismatch (SEQ ID NO:1+Probe No. 18), a 1 bp C-C mismatch (SEQ ID NO:1+Probe No. 19), a 1 bp G-G mismatch (SEQ ID NO:1+Probe No. 20), a 1 bp A-A mismatch (SEQ ID NO:1+Probe No. 21), a 1 bp C-A mismatch (SEQ ID NO:1+Probe No. 22), a 1 bp G-A mismatch (SEQ ID NO:1+Probe No. 23), a 1 bp G-T mismatch (SEQ ID NO:1+Probe No. 24), a 1 bp T-G mismatch (SEQ ID NO:1+Probe No. 25), and a 1 bp T-C mismatch (SEQ ID NO:1+Probe No. 26) produced fluorescent emission intensities that were 63%, 67%, 76%, 59%, 54%, 57%, 59%, 56% and 82% lower, respectively, than that emitted by the perfectly matched dsDNA:ssDNA complexes (FIGS. 12C and 12D).

The variability in the fluorescent emission intensities observed between the various 1 bp mismatches depended more on the particular base pair mismatch than the change in percent GC content of the mutant triple strand sequences (FIG. 12). The results of FIG. 12 confirmed the reliability of the triple strand assay to identify all possible 1 bp mismatches with great accuracy when antisense or sense ssDNA probes were reacted with non-denatured dsDNA targets in the presence of the DNA decondensing agent YOYO-1.

While the invention has been described in detail and with reference to specific examples thereof, it will be apparent to one skilled in the art that various changes and modifications can be made therein without departing from the spirit and scope thereof.

What is claimed is:

1. A method of creating a nucleic acid multiplex, said method comprising the steps of:

1) creating a mixture comprising water, a Watson-Crick duplex, a sufficient number of single-stranded mixed base sequence molecules to form the multiplex including the Watson-Crick duplex, and an accelerator agent that increases a rate or amount of multiplex formation, said multiplex being a triplex or quadruplex; and 2) incubating said mixture to allow the multiplex to form, each strand of said multiplex related to all other strands of the multiplex by adherence to Watson-Crick base-pairing rules or homologous binding base-pairing rules;

provided that, within the multiplex, the Watson-Crick duplex added in step (1) is heteropolymeric with a G-C content between 10% and 90% and a combined frequency therein of purine-pyrimidine dimers and pyrimidine-purine dimers exceeds 25%.

2. A method of claim 1 wherein the multiplex created is a triplex, in step (1) the sufficient number of single-stranded molecules is 1, and in step (2) the triplex is formed.

3. A method of claim 1 wherein the duplex substantially retains its double-helical structure and the single-stranded molecule resides in a groove of that double-helical structure.

4. A method of claim 1 wherein the single-stranded molecule is related to one strand of the duplex by Watson-Crick base-pairing rules and to the second strand of the duplex by homologous binding base-pairing rules.

5. A method of claim 4 wherein the duplex substantially retains its double-helical structure and the single-stranded molecule resides in a groove of that double-helical structure.

6. A method of claim 1 wherein steps (1) and (2) are performed with at least one of the nucleic acid strands and the duplexes not in a cell.

7. A method of claim 1 wherein step (2) is performed without assistance of a protein.

8. A method of claim 1 wherein in step (1), the water is added so that it accounts, on a volume basis, for at least 50 percent of a final volume of the mixture.

9. A method of claim 1 wherein in step (1), the water is added so that it accounts, on a volume basis, for at least 80 percent of a final volume of the mixture.

10. A method of claim 1 wherein in step (1), the water is added so that it accounts, on a volume basis, for all of the liquid added to the mixture.

11. A method of claim 1 wherein step (2) is performed at a temperature or temperatures above a freezing temperature of the mixture and at not more than 85° C.

12. A method of claim 11 wherein the temperature or temperatures is/are 5° C. to 30° C.

13. A method of claim 12 wherein the temperature or temperatures is/are 15° C. to 25° C.

14. A method of claim 1 wherein in step (1), a cation is added as the accelerator agent.

15. A method of claim 14 wherein said cation is Na$^+$ provided at a concentration of 50 mM to 125 mM.

16. A method of claim 14 wherein said cation is selected from the group consisting of Mn$^{+2}$ provided at a concentration of 10 mM to 45 mM, Mg$^{+2}$ provided at a concentration of 10 mM to 45 mM, and Ni$^{+2}$ provided at a concentration of 20 mM.

17. A method of claim 1 wherein in step (1) an intercalator is added as an accelerator agent.

18. A method of claim 17 wherein the intercalator is a fluorescent intercalator.

19. A method of claim 18 wherein the fluorescent intercalator is selected from the group consisting of YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, cyanine monomers, ethidium bromide, ethidium homodimer-1, ethidium homodimer-2, ethidium derivatives, acridine, acridine orange, acridine derivatives, ethidium-acridine heterodimer, ethidium monoazide, propidium iodide, SYTO dyes, SYBR Green 1, SYBR dyes, Pico Green, SYTOX dyes, and 7-aminoactinomycin D.

20. The method of claim 1 wherein the accelerator agent is a non-intercalating fluorophore.

21. A method of claim 20 wherein the non-intercalating fluorophore is selected from the group consisting of biotin, rhodamine, Alexa dyes, BODIPY dyes, biotin conjugates, thiol-reactive probes, fluorescein and derivatives including but not limited to the caged probes, Oregon Green, Rhodamine Green, QSY dyes.

22. A method of claim 1 wherein in step (1) the accelerator agent is an intercalator that binds to at least one of the minor groove and the major groove of the Watson-Crick duplex.

23. The method of claim 1 wherein in step (1) the accelerator agent at 25° C. is a liquid.

24. The method of claim 23 wherein in step (1) the accelerator agent is an organic liquid soluble in water.

25. The method of claim 1 wherein in step (1) an accelerator agent that is a condensation agent as regards the Watson-Crick duplex is added.

26. The method of claim 1 wherein in step (1) an accelerator agent that is a decondensation agent as regards the Watson-Crick duplex is added.

27. A method of claim 1 wherein the multiplex created is a quadruplex, in step (1) the Watson-Crick duplex is a first Watson-Crick duplex, and in step (1) the sufficient number of single-stranded molecules is 2, those single-stranded molecules are in a second Watson-Crick duplex, and in step (2) the quadruplex is formed from said first and second duplexes.

* * * * *